(12) United States Patent
Ansai et al.

(10) Patent No.: US 7,316,884 B2
(45) Date of Patent: Jan. 8, 2008

(54) 5-METHYLENE-1,3-DIOXOLAN-4-ONE DERIVATIVES, PROCESS FOR THEIR PRODUCTION, POLYMERS OF THE DERIVATIVES, RESIST COMPOSITIONS, AND PATTERN FORMATION PROCESS

(75) Inventors: Ryuichi Ansai, Kanagawa (JP); Yoshihiro Kamon, Hiroshima (JP); Tadayuki Fujiwara, Kanagawa (JP); Hideaki Kuwano, Kanagawa (JP); Atsushi Ootake, Kanagawa (JP); Hikaru Momose, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 139 days.

(21) Appl. No.: 10/492,207

(22) PCT Filed: Oct. 22, 2002

(86) PCT No.: PCT/JP02/10938

§ 371 (c)(1),
(2), (4) Date: Apr. 22, 2004

(87) PCT Pub. No.: WO03/035637

PCT Pub. Date: May 1, 2003

(65) Prior Publication Data

US 2004/0248031 A1   Dec. 9, 2004

(30) Foreign Application Priority Data

Oct. 23, 2001 (JP) ............................. 2001-324824
Jan. 15, 2002 (JP) ............................. 2002-006354
May 31, 2002 (JP) ............................. 2002-159847
Aug. 1, 2002 (JP) ............................. 2002-225066

(51) Int. Cl.
G03C 1/73 (2006.01)
G03F 7/20 (2006.01)
G03F 7/30 (2006.01)
C08F 220/10 (2006.01)
C08F 224/00 (2006.01)
C07D 317/34 (2006.01)
C07D 317/72 (2006.01)

(52) U.S. Cl. .................. 430/270.1; 430/325; 430/326; 430/330; 430/942; 430/905; 430/910; 526/266; 526/270; 549/263; 549/264; 549/295; 549/296; 549/323; 549/324; 549/326

(58) Field of Classification Search ................. 526/266, 526/268, 270; 430/910, 270.1, 325, 326, 430/914, 945
See application file for complete search history.

(56) References Cited

U.S. PATENT DOCUMENTS 6,146,811 A * 11/2000 Kim et al. ............... 430/270.1
2003/0054285 A1* 3/2003 Lee et al. ............... 430/270.1

FOREIGN PATENT DOCUMENTS

| EP | 0 640 579 | * | 3/1995 |
| JP | 58-176618 | * | 10/1983 |
| JP | 3-37214 | * | 2/1991 |
| JP | 4-39665 |  | 2/1992 |
| JP | 7-070106 |  | 3/1995 |

(Continued)

OTHER PUBLICATIONS

English Abstract for JP 3-37214, provided by JPO.*
Liu et al (Chem. Abstract 2001:832018 for "Preparation and Characterization of Novel Polymers Having Pendant Ketal Moieties for Positive Photoresists", Macromolecular Chemistry and Physics, 202(15), p. 2986-2991.*
Likhterov et al (Chem. Abstract 1986:186333 for "Synthesis and Properties of 5-methylene-1,3-dioxolan-4-ones", Khimiya Geterotsiklicheskikh Soedinenii (40), p. 1316-18.*

(Continued)

Primary Examiner—Sin Lee
(74) Attorney, Agent, or Firm—Oblon, Spivak, McClelland, Maier & Neustadt, P.C.

(57) ABSTRACT

A 5-methylene-1,3-dioxolan-4-one derivative and a monomer and copolymer thereof and a resist composition containing the polymer or copolymer where the 5-methylene-1,3-dioxolan-4-one derivative is of formula (1):

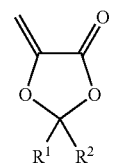

(1)

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

44 Claims, 6 Drawing Sheets

FOREIGN PATENT DOCUMENTS

| | | |
|---|---|---|
| JP | 9-073173 | 3/1997 |
| JP | 9-090637 | 4/1997 |
| JP | 10-153864 | 6/1998 |
| JP | 10-207069 | 8/1998 |
| JP | 10-274852 | 10/1998 |
| JP | 10-316609 | 12/1998 |
| JP | 10-319595 | 12/1998 |
| JP | 2001-089511 | 4/2001 |
| JP | 2002-082441 | 3/2002 |
| SU | 606313 | 2/1984 |

OTHER PUBLICATIONS

Kim et al ("Chemically amplifed resists based on acrylate polymers containing ketal groups in the side chains", Proceedings of SPIE, vol. 3678, p. 625-632 (1999)) .*

Chem. Abstract 1984:56891—English abstract for JP 58-176618 (Tanaka et al.).*

William R. Roush, et al., J. Org. Chem. vol. 57, pp. 3380-3387 1992.

William J. Bailey, et al., "Free radical ring-opening polymerizationof cyclic acrylates", AM. Chemical Socieyt, Div. Polym. Chemical, vol. 28, No. 1, pp. 154-155 1987.

Tetrahedron Letter, vol. 30, No. 52, pp. 7304-7309 1989.

Toyoharu Miyagawa, et al. Macromol. Chem. Phys. vol. 202, No. 9, pp. 1602-1605 2001.

Pinzhen Feng, Chinese Journal of Polymer Science, vol. 10, No. 4, pp. 350-355 1992.

Satoshi Takechi, et al., Journal of Photopolymer Science and Technology, vol. 9, No. 3, pp. 474-487 1996.

* cited by examiner ic device, a miniaturization technique has been quickly progressed to realize high-density and high-accumulation of a device against the backdrop of the advancement in a lithographic technique. As such a microfabrication technique, the conversion of an exposure source into the light source with
5-METHYLENE-1,3-DIOXOLAN-4-ONE DERIVATIVES, PROCESS FOR THEIR PRODUCTION, POLYMERS OF THE DERIVATIVES, RESIST COMPOSITIONS, AND PATTERN FORMATION PROCESS

TECHNICAL FIELD

The present invention relates to a 5-methylene-1,3-dioxolan-4-one derivative having, at position 2, a bridged cyclic hydrocarbon group or alkyl group substituted with a bridged cyclic hydrocarbon group, which is useful as a raw material monomer for a component resin of a coating material, an adhesive, an agglutinant, a resin for ink, a resist or the like, and a production method thereof. Moreover, the present invention relates to a polymer obtained by polymerizing the 5-methylene-1,3-dioxolan-4-one derivative, which is useful for a resist or the like. In particular, it relates to a polymer for a resist, which is suitable for microfabrication using an excimer laser or electron beam, a resist composition comprising the polymer, and a pattern formation method.

BACKGROUND ART

Various compounds and production methods thereof have previously been known regarding a 5-methylene-1,3-dioxolan-4-one derivative represented by the following general formula (A):

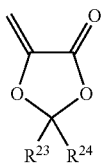

(A)

wherein each of $R^{23}$ and $R^{24}$ represents a hydrogen atom, an alkyl group, an aryl group which may be optionally substituted, or a cyclohexyl group; or $R^{23}$ and $R^{24}$ may form a phenyl group or a cyclic structure of $(CH_2)_m$ together with the carbon atom to which they are bound, wherein the substituent on the aryl group is a linear or branched alkyl group containing 1 to 12 carbon atoms or a halogen atom, and m is an integer of 2 or greater.

For example, J. Organic Chemical, 57(12), 3380 (1992) and Tetrahedron Lett., 30(52), 7305 (1989) describe a method of producing the 5-methylene-1,3-dioxolan-4-one derivative via a 5-(phenylthio)methyl-1,3-dioxolan-4-one derivative obtained by reacting a compound wherein, in the above formula (A), $R^{23}$ represents a hydrogen atom and $R^{24}$ represents a t-butyl group or a cyclohexyl group, and β-(thiophenoxy)methyllactate, with a ketone or an aldehyde. However, the method of producing the above derivative of interest via the 5-(phenylthio)methyl-1,3-dioxolan-4-one derivative has very complicated steps in which the 5-(phenylthio)methyl-1,3-dioxolan-4-one derivative is oxidized at −78° C. using 3-chloroperbenzoic acid followed by a treatment with triethyl phosphate at 210° C.

Japanese Patent Laid-Open No. 7-70106 discloses a compound wherein, in the above formula (A), $R^{23}$ represents a hydrogen atom and $R^{24}$ represents a substituted or unsubstituted alkyl group or a substituted or unsubstituted aryl group (more specifically, 2-tert-butyl-5-methylene-1,3-dioxolan-4-one). In addition, the above published application also discloses a method of producing the compound by reacting a 5-halogeno-5-methyl-1,3-dioxolane-4-one derivative such as 2-tert-butyl-5-bromo-5-methyl-1,3-dioxolan-4-one with a tertiary amine such as trioctylamine or tributylamine in a solvent such as carbon tetrachloride or cyclohexane under reflux, and carrying out a dehydrohalogenation reaction.

Japanese Patent Laid-Open No. 10-316609 discloses a compound wherein, in the above formula (A), each of $R^{23}$ and $R^{24}$ represents an alkyl group (more specifically, 2-tertbutyl-2-methyl-5-methylene-1,3-dioxolan-4-one, etc.). Moreover, the above published application also discloses a method of producing the compound, which comprises: reacting 2,2-disubstituted-5-methyl-1,3-dioxolan-4-one such as 2-tert-butyl-2,5-dimethyl-1,3-dioxolan-4-one, etc., which is synthesized from ketones and lactic acid, with a halogenating agent such as N-bromosuccinimide in a solvent such as cyclohexane under reflux, so as to obtain 2,2-disubstituted-5-halogeno-5-methyl-1,3-dioxolan-4-one; reacting the obtained compound with a tertiary amine such as trioctylamine or triethylamine in a solvent such as cyclohexane under reflux and carrying out a dehydrohalogenation reaction.

Furthermore, USSR Patent No. 606,313 describes a compound wherein, in the above formula (A), each of $R^{23}$ and $R^{24}$ represents a hydrogen atom or an aryl group, or $R^{23}$ and $R^{24}$ form a cyclic structure $(CH_2)_m$ (wherein m represents an integer of 2 or greater). Polym. Prepr. (Am. Chemical Society, Div. Polym. Chemical), 28(1), 154 (1987) describes a compound wherein, in the above formula (A), each of $R^{23}$ and $R^{24}$ represents a methyl group. Japanese Patent Laid-Open No. 3-37214 discloses a compound wherein, in the above formula (A), each of $R^{23}$ and $R^{24}$ represents a hydrogen atom, a phenyl group having an alkyl group containing 1 to 12 carbon atoms or a halogen atom as a substituent, or an alkyl group containing 1 to 12 carbon atoms. Still further, all of the above USSR Patent No. 606,313, Polym. Prepr. (Am. Chemical Society, Div. Polym. Chemical), 28(1), 154 (1987), and Japanese Patent Laid-Open No. 3-37214 describe a production method comprising reacting β-halolactic acid with a ketone or an aldehyde to synthesize a 5-halomethyl-1,3-dioxolan-4-one derivative, and subjecting it to a dehydrohalogenation reaction with a base such as amine.

However, a 5-methylene-1,3-dioxolan-4-one derivative having a bridged cyclic hydrocarbon structure as a substituent and a production method thereof have not been reported so far.

Moreover, several polymers obtained by polymerizing monomers having a 5-methylene-1,3-dioxolan-4-one structure have been known as a water-soluble polymer, a biodegradable polymer, or the like. For example, T. Endo et al., Macromol. Chem. Phys., 202, 1602 (2001) describes a copolymer of 2,2-dimethyl-5-methylene-1,3-dioxolan-4-one and methyl methacrylate. Chin. J. Polym. Sci., 10, 350 (1992) describes a polymer of 2-phenyl-5-methylene-1,3-dioxolan-4-one.

However, a polymer of 5-methylene-1,3-dioxolan-4-one derivatives having a substituent with a bridged cyclic hydrocarbon structure has not been reported so far.

By the way, recently, in the field of microfabrication for production of a semiconductor device or a liquid crystal device, a miniaturization technique has been quickly progressed to realize high-density and high-accumulation of a device against the backdrop of the advancement in a lithographic technique. As such a microfabrication technique, the conversion of an exposure source into the light source with a shorter wavelength has generally been used. Specifically, the exposure source has been changed from the previous ultraviolet ray, as represented by a g-ray (wavelength: 438 nm) or an i-ray (wavelength: 365 nm) to a far ultraviolet ray.

Presently, a KrF excimer laser (wavelength: 248 nm) lithographic technique has been introduced in the market, and an ArF excimer laser (wavelength: 193 nm) lithographic technique, which is directed towards the conversion of an exposure source into the source with a further shorter wavelength, is being introduced in the market. Moreover, an $F_2$ excimer laser (wavelength: 157 nm) lithographic technique is studied as a technique for the next generation. Furthermore, an electron beam lithographic technique, which is a somewhat different type from the above techniques, is also intensively studied.

As a resist with high sensitivity for such a light source with a short wavelength or an electron beam, a "chemically amplified resist" has been proposed by International Business Machine (IBM) Corporation, and at present, the improvement and development of this chemically amplified resist have been advanced vigorously.

By the way, in the conversion of the light source into the one with a shorter wavelength, a resin used for the resist is also forced to change its structure. For example, in the KrF excimer laser lithography, polyhydroxystyrene having high transparency to the light with a wavelength of 248 nm, a compound wherein the hydroxyl group thereof protected with an acid-dissociating solubility-inhibiting group, or the like are used. However, in the ArF excimer laser lithography, often the above resins cannot be used because they do not always have sufficient transparency to the light with a wavelength of 193 nm.

Accordingly, an acrylic resin or a cycloolefin resin that are transparent to the light with a wavelength of 193 nm attract attention as a resist resin used in the ArF excimer laser lithography. Such an acrylic resin is disclosed in published applications such as Japanese Patent Laid-Open Nos. 4-39665, 10-207069 and 9-090637, and such a cycloolefin resin is disclosed in published applications such as Japanese Patent Laid-Open No. 10-153864.

In particular, a copolymer of 2-methyl-2-adamantyl methacrylate draws the attention as a resist resin used in the ArF excimer laser lithography. This copolymer is described in S. Takechi et al., Journal of Photopolymer Science and Technology, Vol. 9, No. 3, 475-487 (1996) and Japanese Patent Laid-Open No. 9-73173. With regard to this copolymer, it has been reported that 2-methyl-2-adamantyl is cleaved by the action of an acid so that it acts as a positive type, and that the copolymer provides high dry etching resistance, high sensitivity and high resolution. However, such a copolymer having an alicyclic skeleton generally tends to have high hydrophobicity, and it does not have sufficient wettability to a developing solution in some cases.

Consequently, in order to decrease the hydrophobicity, several ideas have been proposed, which involve the copolymerization of a methacrylic acid derivative having a lactone structure or the introduction of a hydrophilic group such as a hydroxyl group into the alicyclic structure. For example, Japanese Patent Laid-Open Nos. 10-319595, 10-274852 and the like disclose a copolymer of a (meth) acrylic ester having an adamantane skeleton in an ester portion thereof and a (meth)acrylic ester having a lactone skeleton in an ester portion thereof. In addition, Japanese Patent Laid-Open No. 2002-82441 discloses a cycloolefin or acrylic copolymer containing a lactone structure.

However, in many cases, these acrylic resins or cycloolefin resins do not have sufficient solubility in a solvent when a resist solution is prepared. Accordingly, there may be a case where a long time is required for dissolution of the resin, or the number of the steps of the production method is increased by the generation of an insoluble matter, so that it might affect the preparation of the resist solution. Moreover, there may also be a case where these acrylic resins or cycloolefin resins do not have sufficient heat resistance. Furthermore, when these acrylic resins or cycloolefin resins are used as a resist resin, roughness of a sidewall of a resist pattern formed by patterning with an excimer laser and the subsequent development procedure, that is, line edge roughness might be generated, and consequently, a circuit width might become uneven or the circuit might be broken down, and the use of these acrylic resins or cycloolefin resins as a resist resin may bring about the possibility of the decrease in yield during the production process of a semiconductor.

DISCLOSURE OF THE INVENTION

It is an object of the present invention to provide a novel monomer from which a homopolymer and a copolymer being excellent in light transparency and heat stability are obtained, and a production method thereof. It is another object of the present invention to provide a polymer which is excellent in light transparency and heat stability; a polymer which is excellent in solubility in an organic solvent and has little line edge roughness without damaging the resist performance such as sensitivity, resolution or dry etching resistance; a resist composition suitable for use in deep ultraviolet excimer laser lithography, electron beam lithography and other lithographies; and a method of forming a pattern using the resist composition.

The present invention relates to a 5-methylene-1,3-dioxolan-4-one derivative represented by the following formula (1):

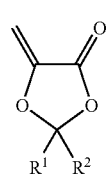

(1)

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

Further, the present invention relates to a 5-halo-5-methyl-1,3-dioxolan-4-one derivative represented by the following formula (2):

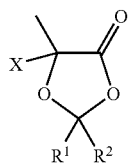

(2)

wherein X represents a chlorine atom or a bromine atom; $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

Furthermore, the present invention relates to a method of producing the 5-halo-5-methyl-1,3-dioxolan-4-one derivative represented by the above formula (2), which comprises the step of:

reacting a 5-methyl-1,3-dioxolan-4-one derivative represented by the following formula (3) with a halogenating agent at a reaction temperature within a range of 50° C. to 65° C.:

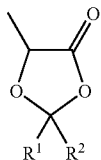

(3)

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

Moreover, the present invention relates to a method of producing the 5-methylene-1,3-dioxolan-4-one derivative represented by the above formula (1), which comprises the step of:

reacting the 5-halo-5-methyl-1,3-dioxolan-4-one derivative represented by the above formula (2) with an amide compound represented by the following formula (5) to carry out a dehydrohalogenation reaction:

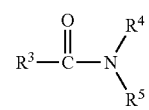

(5)

wherein each of $R^3$, $R^4$ and $R^5$ independently represents a hydrogen atom, or a linear or branched alkyl group containing 1 to 4 carbon atoms.

Further, the present invention relates to a method of producing the 5-methylene-1,3-dioxolan-4-one derivative represented by the above formula (1), which comprises the step of:

reacting a 5-halomethyl-1,3-dioxolan-4-one derivative represented by the following formula (4) with an amide compound represented by the following formula (5) to carry out a dehydrohalogenation reaction:

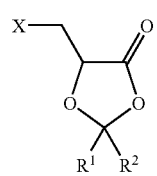

(4)

wherein X represents a chlorine atom or a bromine atom; $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms; and

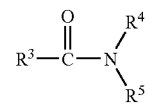

(5)

wherein each of $R^3$, $R^4$ and $R^5$ independently represents a hydrogen atom, or a linear or branched alkyl group containing 1 to 4 carbon atoms.

Furthermore, the present invention relates to a polymer obtained by (co)polymerizing a monomer composition comprising a monomer represented by the above formula (1).

Moreover, the present invention relates to a polymer comprising at least one of constitutional units represented by the following formula (6):

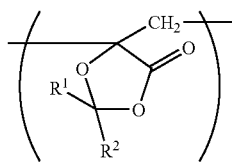

(6)

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

Further, the present invention relates to a polymer comprising at least one of constitutional units represented by the following formula (7) and at least one of constitutional units represented by the following formula (8), (9) or (10):

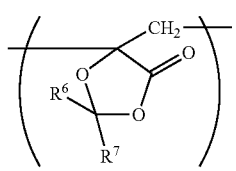

(7)

wherein each of $R^6$ and $R^7$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^6$ and $R^7$ represent a cyclic hydrocarbon group containing 4 to 16 carbon atoms together with the carbon atom to which they are bound, provided that the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms;

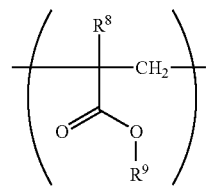

(8)

wherein $R^8$ represents a hydrogen atom or a methyl group, and $R^9$ represents a linear or branched alkyl group containing 1 to 6 carbon atoms, a cyclic hydrocarbon group containing 4 to 8 carbon atoms, or a bridged cyclic hydrocarbon group containing 4 to 16 carbon atoms, provided that the alkyl group, the cyclic hydrocarbon group and the bridged cyclic hydrocarbon group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms;

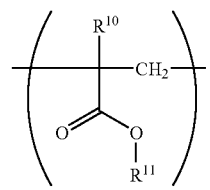

(9)

wherein $R^{10}$ represents a hydrogen atom or a methyl group, and $R^{11}$ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group, provided that the alkyl group, the cyclic hydrocarbon group, the bridged cyclic hydrocarbon group and the hydrophilic functional group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms; and

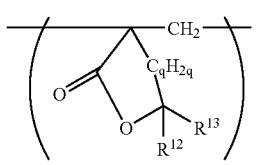

(10)

wherein each of $R^{12}$ and $R^{13}$ independently represents a hydrogen atom, a methyl group or an ethyl group, and q represents an integer of 1 to 4.

It is to be noted that, in this polymer, the constitutional units (7), (8), (9) and (10) are not necessarily of the same type, but two or more types may be mixed therein. Moreover, in this polymer, each constitutional unit can have any given sequence. Accordingly, this polymer may be a random copolymer, an alternating copolymer, or a block copolymer.

Further, the present invention relates to the above polymer wherein the constitutional unit represented by the above formula (7) is the constitutional unit represented by the above formula (6).

Furthermore, the present invention relates to a polymer comprising at least one of constitutional units represented by the following formula (11):

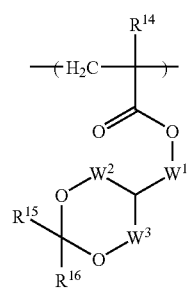

(11)

wherein $W^1$ represents a direct bond or a methylene chain containing 1 to 6 carbon atoms [—$(CH_2)_k$— (wherein k represents an integer of 0 to 6)], $W^2$ represents a direct bond or a methylene chain containing 1 to 3 carbon atoms [—$(CH_2)_l$— (wherein l represents an integer of 0 to 3)], $W^3$ represents a methylene chain containing 1 to 3 carbon atoms [—$(CH_2)_m$— (wherein m represents an integer of 1 to 3)], $R^{14}$ represents a hydrogen atom or a methyl group, $R^{15}$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent, $R^{16}$ represents a hydrogen atom, or a linear or branched alkyl group containing 1 to 6 carbon atoms; or $R^{15}$ and $R^{16}$ represent a bridged cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, the methylene chain containing 1 to 3 carbon atoms may have a carbonyl group therein, and the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

Moreover, the present invention relates to a polymer comprising at least one of constitutional units represented by the following formula (12):

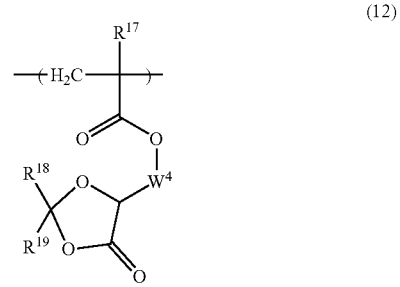

(12)

wherein $W^4$ represents a direct bond or a methylene chain containing 1 to 6 carbon atoms [—$(CH_2)_n$— (wherein n represents an integer of 0 to 6)], $R^{17}$ represents a hydrogen atom or a methyl group, each of $R^{18}$ and $R^{19}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{18}$ and $R^{19}$ represent a cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, and the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

Further, the present invention relates to a polymer comprising at least one of constitutional units represented by the following formula (13) and at least one of constitutional units represented by the above formula (8), (9) or (10):

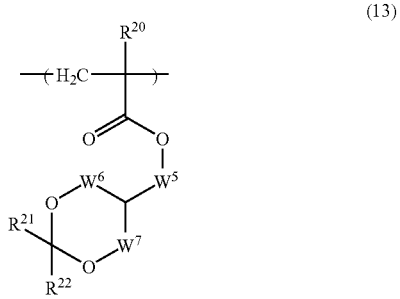

(13)

wherein $W^5$ represents a direct bond or a methylene chain containing 1 to 6 carbon atoms [—$(CH_2)_x$— (wherein x represents an integer of 0 to 6)], $W^6$ represents a direct bond or a methylene chain containing 1 to 3 carbon atoms [—$(CH_2)_y$— (wherein y represents an integer of 0 to 3)], $W^7$ represents a methylene chain containing 1 to 3 carbon atoms [—$(CH_2)_z$— (wherein z represents an integer of 1 to 3)], $R^{20}$ represents a hydrogen atom or a methyl group, each of $R^{21}$ and $R^{22}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{21}$ and $R^{22}$ represent a cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, the methylene chain containing 1 to 3 carbon atoms may have a carbonyl group therein, and the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

It is to be noted that, in this polymer, the constitutional units (13), (8), (9) and (10) are not necessarily of the same type, but two or more types may be mixed therein. Moreover, in this polymer, each constitutional unit can have any given sequence. Accordingly, this polymer may be a random copolymer, an alternating copolymer, or a block copolymer.

Further, the present invention relates to the above polymer wherein the constitutional unit represented by the above formula (13) is the constitutional unit represented by the above formula (11) or (12).

Furthermore, the present invention relates to the above polymer wherein its mass-average molecular weight is within a range of 1,000 to 100,000.

Moreover, the present invention relates to a polymer mixture comprising at least one polymer described above, and at least one polymer comprising at least one of constitutional units represented by the above formula (8), (9) or (10).

Further, the present invention relates to a resist composition, which comprises at least one polymer comprising at least one of constitutional units represented by the above formula (7).

Furthermore, the present invention relates to a resist composition, which comprises at least one polymer comprising at least one of constitutional units represented by the above formula (13).

Moreover, the present invention relates to a resist composition, which comprises at least one polymer described above or the above polymer mixture.

Further, the present invention relates to a resist composition, which comprises at least one polymer described above or the above polymer mixture, and a photoacid generator.

Furthermore, the present invention relates to a method of forming a pattern, which comprises the steps of:

coating the above resist composition onto a substrate to be processed;

exposing the substrate to a light with a wavelength of 250 nm or shorter or an electron beam; and development.

Moreover, the present invention relates to a method of forming a pattern, which comprises the steps of:

coating the above resist composition onto a substrate to be processed;

exposing the substrate to a light with a wavelength of 250 nm or shorter or an electron beam; and developing it with a developing solution after subjecting it to a heat treatment, if necessary.

The term "(co)polymerization" is used herein to mean either homopolymerization or copolymerization, as it is commonly used.

BEST MODE FOR CARRYING OUT THE INVENTION

Figure 1:
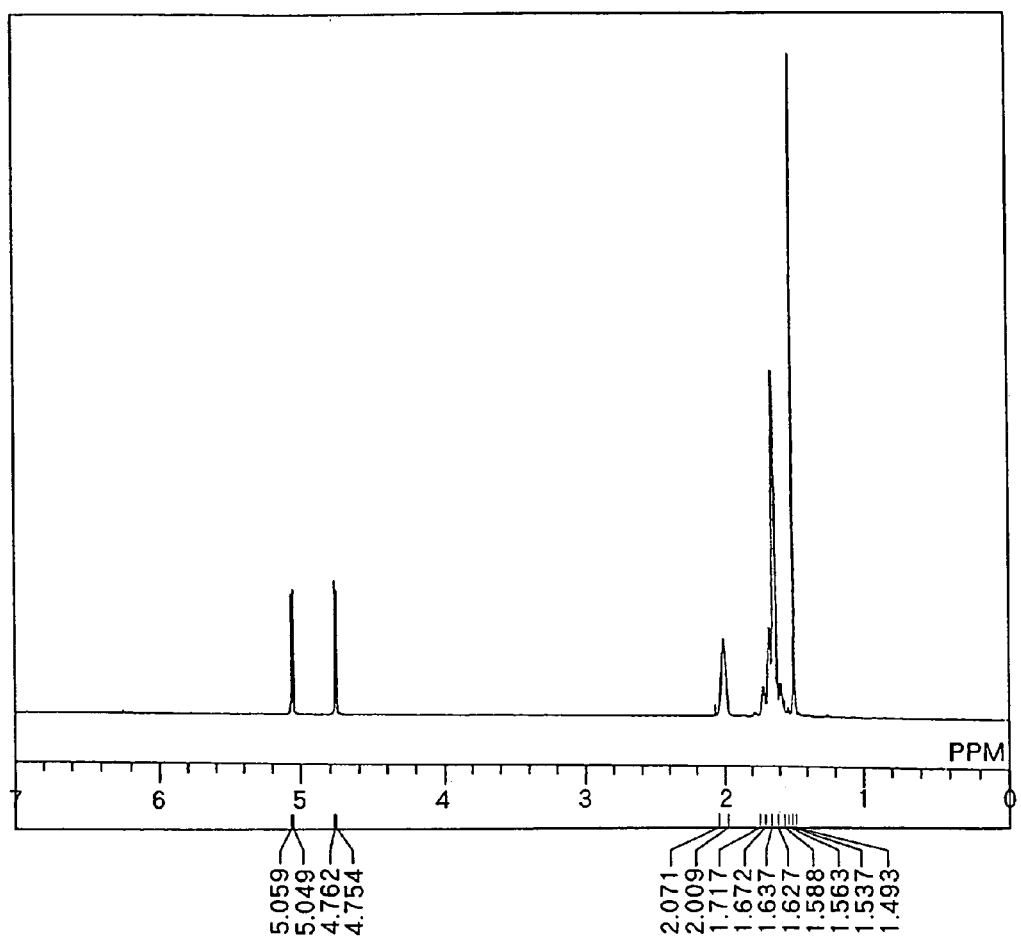
FIG. 1 is a $^1$H-NMR spectrum of the compound represented by a formula (19), which was obtained in Example 1.

The compound of the present invention comprising a 5-methylene-1,3-dioxolan-4-one structure is a 5-methylene-1,3-dioxolan-4-one derivative represented by the above formula (1). The 5-methylene-1,3-dioxolan-4-one derivative of the present invention is a novel compound having, at position 2, a substituent having a bridged cyclic hydrocarbon structure. This derivative is particularly useful in that a homopolymer or a copolymer obtained by (co)polymerization of this monomer is excellent in light transparency and heat stability. Moreover, the 5-methylene-1,3-dioxolan-4-one derivative of the present invention is excellent in stability, moderate polarity and solubility in various solvents, and exhibits acid decomposition properties. Its polymer can also be expected to be excellent in stability, moderate polarity and solubility in various solvents, and to exhibit acid decomposition properties. Accordingly, the 5-methylene-1,3-dioxolan-4-one derivative of the present invention can be widely used as a raw material monomer for a component resin of a coating material, an adhesive, an agglutinant, a resin for ink, a resist, or the like.

Such a 5-methylene-1,3-dioxolan-4-one derivative of the present invention can be easily produced with a high yield and a high purity by reacting the 5-halo-5-methyl-1,3-dioxolan-4-one derivative represented by the above formula (2), which can be obtained by reacting the 5-methyl-1,3-dioxolan-4-one derivative represented by the above formula (3) with a halogenating agent at a reaction temperature within a range of 50° C. to 65° C., or the 5-halomethyl-1,3-dioxolan-4-one derivative represented by the above formula (4), with the amide compound represented by the above formula (5) to carry out a dehydrohalogenation reaction.

Moreover, the first polymer of the invention is obtained by (co)polymerizing a monomer composition comprising the monomer represented by the above formula (1), and comprises a monomer unit wherein the unsaturated bond of the monomer represented by the above formula (1) is open-chained (transfer of electrons), that is, the constitutional unit represented by the above formula (6). The monomer represented by the above formula (1) may be a single type or a mixture of two or more types.

Furthermore, the second polymer of the invention comprises at least one of constitutional units represented by the above formula (7) and at least one of constitutional units represented by the above formula (8), (9) or (10). The constitutional units (7), (8), (9) and (10) are not necessarily of the same type, but two or more types may be mixed therein. The constitutional unit represented by the above formula (7) is preferably the constitutional unit represented by the above formula (6).

Still further, the third polymer of the invention comprises at least one of constitutional units represented by the above formula (11). The constitutional unit (11) is not necessarily of the same type, but two or more types may be mixed therein.

Still further, the fourth polymer of the invention comprises at least one of constitutional units represented by the above formula (12). The constitutional unit (12) is not necessarily of the same type, but two or more types may be mixed therein.

Still further, the fifth polymer of the invention comprises at least one of constitutional units represented by the above formula (13) and at least one of constitutional units represented by the above formula (8), (9) or (10). The constitutional units (13), (8), (9) and (10) are not necessarily of the same type, but two or more types may be mixed therein. The constitutional unit represented by the above formula (13) is preferably the constitutional unit represented by the above formula (11) or (12).

In all of the above first to fifth polymers of the invention, each constitutional unit can have any given sequence. Accordingly, these polymers may be a random copolymer, an alternating copolymer, or a block copolymer.

The polymer of the present invention is excellent in solubility in an organic solvent (resist solvent) and heat resistance, and has little line edge roughness, while maintaining its resist performance such as sensitivity, resolution and dry etching resistance. The polymer of the present invention is particularly preferable as a resist resin used in deep ultraviolet excimer laser lithography, electron beam lithography, and other lithographies.

Hereinafter, the present invention will be described in detail.

1. 5-methylene-1,3-dioxolan-4-one derivative of the Present Invention

First, a 5-methylene-1,3-dioxolan-4-one derivative represented by the following formula (1) will be explained:

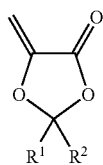

(1)

In formula (1), $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the bridged cyclic hydrocarbon group have two or more substituents, the substituents may be of either a single type, or two or more types.

Examples of a substituent on the linear or branched alkyl group containing 1 to 6 carbon atoms that is the substituent on the alkyl group and the bridged cyclic hydrocarbon group may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

The bridged cyclic hydrocarbon group is a group having a structure represented by the following formula (15) or (16) including adamantane and norbornane as typical examples:

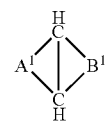

(15)

wherein each of $A^1$ and $B^1$ represents a linear or branched alkylene group, and $A^1$ and $B^1$ may be identical or may be different; or

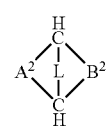

(16)

wherein each of $A^2$, $B^2$ and L represents a linear or branched alkylene group, and $A^2$, $B^2$ and L may be identical or may be different.

Examples of $R^1$ in the above formula (1) may include bridged cyclic hydrocarbon groups such as a 2-norbornyl group, 1-adamantyl group, 1-adamantanemethyl group, 1-adamantaneethyl group, 2-adamantyl group, 2-adamantanemethyl group, 2-adamantaneethyl group or 2-adamantanonyl group. Moreover, $R^1$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Of these, in terms of having excellent dry etching resistance when the polymer is used for a resist composition, a 2-norbornyl group, a 1-adamantyl group, a 1-adamantanemethyl group, a 1-adamantaneethyl group, a 2-adamantyl group, a 2-adamantanemethyl group and a 2-adamantaneethyl group are preferable as $R^1$. In terms of the light transparency and heat stability such as a glass transition temperature (Tg) of the (co)polymer to be obtained, a 1-adamantyl group and a 2-norbornyl group are more preferable as $R^1$.

Examples of $R^2$ in the above formula (1) may include a hydrogen atom, a methyl group, an ethyl group, a propyl group, an isopropyl group, a butyl group, and a tert-butyl group. Moreover, $R^2$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Of these, a methyl group and an ethyl group are preferable as $R^2$, in terms of having excellent coatability when the polymer is used for a resist composition.

Further, $R^1$ and $R^2$ in the above formula (1) may form a bridged cyclic hydrocarbon structure containing 4 to 16 carbon atoms, together with the carbon atom to which they are bound. Examples of such a derivative represented by the above formula (1) may include spiro[norbornan-2,2'-(5'-methylene-1',3'-dioxolan-4'-one) and spiro[adamantan-2,2'-(5'-methylene-1',3'-dioxolan-4'-one). Furthermore, examples of such a derivative may also include those wherein the bridged cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Preferred examples of the 5-methylene-1,3-dioxolan-4-one derivative represented by the above formula (1) may include 5-methylene-2-(1-adamantyl)-2-methyl-1,3-dioxolan-4-one, 5-methylene-2-(2-adamantyl)-2-methyl-1,3-dioxolan-4-one, 5-methylene-2-methyl-2-(2-norbornyl)-1,3-dioxolan-4-one, 5-methylene-2-(1-adamantanemethyl)-2-methyl-1,3-dioxolan-4-one, 5-methylene-2-(2-adamantanemethyl)-2-methyl-1,3-dioxolan-4-one, 5-methylene-2-(1-adamantaneethyl)-2-methyl-1,3-dioxolan-4-one, 5-methylene-2-(2-adamantaneethyl)-2-methyl-1,3-dioxolan-4-one, 5-methylene-2-(1-adamantyl)-2-ethyl-1,3-dioxolan-4-one, 5-methylene-2-(2-adamantyl)-2-ethyl-1,3-dioxolan-4-one, 5-methylene-2-ethyl-2-(2-norbornyl)-1,3-dioxolan-4-one, 5-methylene-2-(1-adamantanemethyl)-2-ethyl-1,3-dioxolan-4-one, 5-methylene-2-(2-adamantanemethyl)-2-ethyl-1,3-dioxolan-4-one, 5-methylene-2-(1-adamantaneethyl)-2-ethyl-1,3-dioxolan-4-one, 5-methylene-2-(2-adamantaneethyl)-2-ethyl-1,3-dioxolan-4-one, and the like.

As stated above, in the above compounds, an alkyl group and/or a bridged cyclic hydrocarbon group may be substituted with a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, a carboxy group esterified with an alcohol containing 1 to 6 carbon atoms, or the like. The number of substituents may be either one, or two or more. When the above compound has two or more substituents, the substituents may be of either a single type, or two or more types.

Of these, a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms are preferable as a substituent, in terms of having excellent light transparency when the polymer is used for a resist composition. Moreover, in terms of having excellent dry etching resistance when the polymer is used for a resist composition, a methyl group and an ethyl group are more preferable as a substituent. And, in terms of having excellent adhesion of the polymer to a substrate when the polymer is used for a resist composition, a hydroxyl group, a hydroxymethyl group, and a hydroxyethyl group are more preferable as a substituent.

2. 5-halo-5-methyl-1,3-dioxolan-4-one derivative of the Present Invention

Next, a 5-halo-5-methyl-1,3-dioxolan-4-one derivative represented by the following formula (2) will be explained, which will be an intermediate when the 5-methylene-1,3-dioxolan-4-one derivative represented by the above formula (1) is produced:

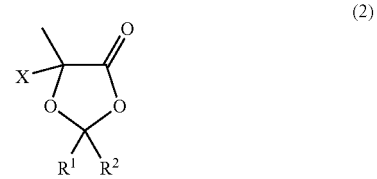

In formula (2), X represents a chlorine atom or a bromine atom; $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the bridged cyclic hydrocarbon group have two or more substituents, the substituents may be of either a single type, or two or more types.

$R^1$ and $R^2$ in the formula (2) correspond to $R^1$ and $R^2$ in the formula (1), respectively. Accordingly, the $R^1$ and $R^2$ in the formula (2) are the same as the $R^1$ and $R^2$ in the formula (1), and preferred examples of $R^1$ and $R^2$ in the formula (2) are also the same as the preferred examples of $R^1$ and $R^2$ in the formula (1).

Moreover, a bromine atom is preferable as X in the above formula (2) because when the derivative is converted into the 5-methylene-1,3-dioxolan-4-one derivative represented by the above formula (1), the reaction more smoothly progresses.

3. Production method of the 5-halo-5-methyl-1,3-dioxolan-4-one derivative of the Present Invention Next, a method of producing the 5-halo-5-methyl-1,3-dioxolan-4-one derivative represented by the above formula (2) of the present invention will be explained.

The 5-halo-5-methyl-1,3-dioxolan-4-one derivative represented by the above formula (2) can be produced by reacting a 5-methyl-1,3-dioxolan-4-one derivative represented by the following formula (3) as a raw material with a halogenating agent, so that the position 5 of the above derivative is halogenated:

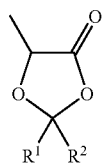

(3)

In formula (3), $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the bridged cyclic hydrocarbon group have two or more substituents, the substituents may be of either a single type, or two or more types.

$R^1$ and $R^2$ in the formula (3) correspond to $R^1$ and $R^2$ in the formula (2), respectively. Accordingly, the $R^1$ and $R^2$ in the formula (3) are the same as the $R^1$ and $R^2$ in the formula (2), and preferred examples of $R^1$ and $R^2$ in the formula (3) are also the same as the preferred examples of $R^1$ and $R^2$ in the formula (2). That is to say, the $R^1$ and $R^2$ in the formula (3) are the same as the $R^1$ and $R^2$ in the formula (1), and preferred examples of $R^1$ and $R^2$ in the formula (3) are also the same as the preferred examples of $R^1$ and $R^2$ in the formula (1).

I. Production Method of the Derivative Represented by the Above Formula (3), Which is a raw Material The 5-methyl-1,3-dioxolan-4-one derivative represented by the above formula (3) that is a raw material can be synthesized from the ketone or aldehyde represented by the following formula (17) by a known method:

(17)

wherein $R^1$ and $R^2$ correspond to $R^1$ and $R^2$ in the formula (3), respectively.

That is to say, in the above formula (17), $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

The 5-methyl-1,3-dioxolan-4-one derivative represented by the above formula (3) can be synthesized, for example, by reacting the compound represented by the above formula (17) with a lactic acid or an ester thereof, the reaction being accompanied with dehydration or dealcoholization. This addition reaction is preferably carried out at a reaction temperature within a range of 20° C. to a reflux temperature under conditions in which either the compound represented by the above formula (17), or a lactic acid or an ester thereof is in an excessive amount. The addition reaction can sufficiently progress with acidity of lactic acid, but an acid catalyst such as a Lewis acid may be used. Moreover, the addition reaction may be carried out with no solvents, or it may be carried out in a two-phase system containing an organic solvent and a lactic acid, using a nonpolar organic solvent. The addition reaction can be carried out in either a homogeneous system, or a heterogeneous system.

Furthermore, the 5-methyl-1,3-dioxolan-4-one derivative represented by the above formula (3) can also be synthesized by reacting the compound represented by the above formula (17) with a orthoformic acid trimethyl ester to obtain a dimethoxy form or an enol ether form, and then conducting a reaction of the obtained compound with a lactic acid, the reaction being accompanied with demethanolation. The reaction between the dimethoxy form and the lactic acid is preferably carried out at a reaction temperature within a range of 20° C. to a reflux temperature under conditions in which either the dimethoxy form or the enol ether form, or the lactic acid is in an excessive amount. This reaction can sufficiently progress with acidity of lactic acid, but an acid catalyst such as a Lewis acid is preferably used. Moreover, this reaction may be carried out with no solvents, or it may be carried out in a two-phase system containing an organic solvent and a lactic acid, using a nonpolar organic solvent. The reaction can be carried out in either a homogeneous system, or a heterogeneous system.

Examples of a pattern of the reaction may include a closed system in which the reaction is carried out under reduced pressure, under ordinary pressure or under increased pressure, using a well-closed container; and a reflux system in which the reaction is carried out at a boiling point or lower and a volatilized raw material, product and solvent are refluxed with a condenser. These reactions are preferably carried out using a Dienstark or a decanter to remove the generated water or alcohol to the outside of the system.

Moreover, an optically active lactic acid can also be used in the reaction to form the derivative represented by the above formula (3). In this case, the obtained derivative represented by the above formula (3) has optical activity that is derived from the raw material.

II. Production Method of the Derivative Represented by the Above Formula (2)

As stated above, the 5-halo-5-methyl-1,3-dioxolan-4-one derivative represented by the above formula (2) can be produced by reacting the 5-methyl-1,3-dioxolnae-4-one derivative represented by the above formula (3) with a halogenating agent at a reaction temperature within a range of 50° C. to 65° C.

Examples of a halogenating agent used in the above reaction may include N-chlorosuccinimide, 1,3-dichloro-5,5-dimethylhydantoin, bromotrichloromethane, N-bromosuccinimide, 1,3-dibromo-5,5-dimethylhydantoin, and bromine. Such a halogenating agent may be used singly or in combination of two or more types. Of these, in terms of reactivity and selectivity of a position to be halogenated, N-bromosuccinimide is particularly preferably used.

In terms of yield, the use amount of a halogenating agent is preferably 0.1 mole or more, more preferably 0.5 mole or more, and particularly preferably 1 mole or more based on 1 mole of the derivative represented by the formula (3). In addition, in terms of prevention of a decomposition reaction, the use amount of a halogenating agent is preferably 10 mole or less, more preferably 2 mole or less, and particularly preferably 1.5 mole or less based on 1 mole of the derivative represented by the formula (3).

A radical generator such as azobisisobutyronitrile may be used in the conventional halogenation reaction. However, in the halogenation reaction of the present invention, the reaction sufficiently progresses without using such a radical generator. In the present invention, in the case of using a radical generator, the use amount of the radical generator is usually 0.1 mole or less based on 1 mole of the derivative represented by the formula (3). However, so as to reduce impurities passed into the next step, it is preferably 0.01 mole or less based on 1 mole of the derivative represented by the formula (3).

An organic solvent is preferably used in the present halogenation reaction. Any organic solvent can be used as long as it is used in a halogenation reaction. Examples of an organic solvent used herein may include pentane, hexane, heptane, cyclopentane, cyclohexane, diethyl ether, diisopropyl ether, methyl-tert-butyl ether, tetrahydrofuran, carbon tetrachloride, chloroform, and methylene chloride. Such an organic solvent may be used singly or in combination of two or more types. Of these, in terms of smooth progression of the reaction, hexane, heptane, cyclohexane, carbon tetrachloride or the like are preferably used.

In terms of smooth progression of the reaction and suppression of generation of by-products, the use amount of an organic solvent is preferably 0.1 time by mass or more, more preferably 0.5 time by mass or more, and particularly preferably 1 time by mass or more based on the derivative represented by the formula (3). In addition, in terms of reaction rate and the amount of the waste solvent, the use amount of an organic solvent is preferably 100 times by mass or less, more preferably 50 times by mass or less, and particularly preferably 20 times by mass or less based on the derivative represented by the formula (3).

Water may be contained in such an organic solvent, however, in terms of prevention of a decomposition reaction and a side reaction, it is more preferable that water is contained in the organic solvent in a small amount.

The reaction temperature is generally set within a range of 50° C. to 65° C. In terms of reaction rate, the reaction temperature is preferably 55° C. or higher. In addition, in terms of prevention of a decomposition reaction, the reaction temperature is preferably 60° C. or lower.

Conventionally, when a halogenation reaction using a halogenating agent progresses radically, the reaction is generally carried out around 80° C. at which a radical is likely to generate. At such a temperature, however, the decomposition reaction of a raw material and a halide progresses significantly, resulting in a significant decrease in the yield of the derivative represented by the above formula (2). This decomposition reaction particularly progresses significantly, when a substituent bound to position 2 has a bridged cyclic hydrocarbon structure. The inventors have found that the halogenation reaction of the present invention progresses even if the reaction temperature is set to 65° C. or lower at which the reaction is not conventionally carried out, and that the decomposition reaction of a raw material and a halide only slightly progresses at this temperature.

Examples of a pattern of the halogenation reaction may include a closed system in which the reaction is carried out under reduced pressure, under ordinary pressure or under increased pressure, using a well-closed container; and a reflux system in which the reaction is carried out at a boiling point or lower and a volatilized raw material, product and solvent are refluxed with a condenser.

The reaction time may be determined, taking into consideration the reaction temperature or the like. Generally, the reaction time is preferably about 1 to 48 hours.

In the present invention, a halogenation reaction is carried out as described above, so as to produce the derivative represented by the above formula (2). In the present reaction, the product of interest can be obtained at a good yield while sufficiently preventing a side reaction. Accordingly, the obtained derivative represented by the above formula (2) can be directly used in the following dehydrohalogenation reaction. Otherwise, an unreacted halide (e.g., N-bromosuccinimide) and a by-product (e.g., succinimide) are removed from the reaction solution by filtration, and the residue may be used in the dehydrohalogenation reaction. If necessary, removal of a solvent or exchange of a solvent may be carried out. Moreover, the obtained derivative represented by the above formula (2) may be purified by a known method such as washing with an alkaline aqueous solution, extraction with an organic solvent/water system, solvent fractionation, column chromatography, or vacuum distillation.

Where $R^1$ differs from $R^2$ in the derivative represented by the above formula (2), the carbon atom at position 2 becomes an asymmetric carbon, and optical isomers exist. These optical isomers can be isolated by a known optical resolution method such as preferential crystallization method or the use of an optical resolution column. These optically active substances may be either an (R)-form or a (S)-form, or may be a mixture of the (R)-form and the (S)-form, and all of these substances can be used in the following dehydrohalogenation reaction.

4. Production method of the 5-methylene-1,3-dioxolan-4-one derivative of the Present Invention Next, a method of producing the 5-methylene-1,3-dioxolan-4-one derivative represented by the above formula (1) of the present invention will be explained.

The 5-methylene-1,3-dioxolan-4-one derivative represented by the above formula (1) can be produced by reacting the 5-halo-5-methyl-1,3-dioxolan-4-one derivative represented by the above formula (2) or a 5-halomethyl-1,3-dioxolan-4-one derivative represented by the following formula (4) with an amide compound represented by the following formula (5) so as to carry out a dehydrohalogenation reaction:

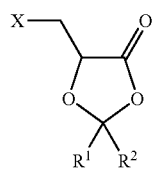

(4)

wherein X represents a chlorine atom or a bromine atom; $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms; and

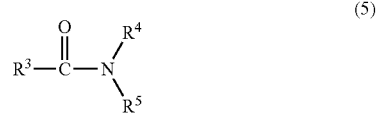

(5)

wherein each of $R^3$, $R^4$ and $R^5$ independently represents a hydrogen atom, or a linear or branched alkyl group containing 1 to 4 carbon atoms.

I. 5-halomethyl-1,3-dioxolan-4-one derivative Represented by the Above Formula (4)

In the above formula (4), X represents a chlorine atom or a bromine atom; $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the bridged cyclic hydrocarbon group have two or more substituents, the substituents may be of either a single type, or two or more types.

$R^1$ and $R^2$ in the formula (4) correspond to $R^1$ and $R^2$ in the formula (1), respectively. Accordingly, the $R^1$ and $R^2$ in the formula (4) are the same as the $R^1$ and $R^2$ in the formula (1), and preferred examples of $R^1$ and $R^2$ in the formula (4) are also the same as the preferred examples of $R^1$ and $R^2$ in the formula (1).

Moreover, a bromine atom is preferable as X in the above formula (4) because when the derivative is converted into the 5-methylene-1,3-dioxolan-4-one derivative represented by the above formula (1), the reaction more smoothly progresses.

The 5-halomethyl-1,3-dioxolan-4-one derivative represented by the above formula (4) can be synthesized from the ketone or aldehyde represented by the following formula (17) by a known method:

(17)

wherein $R^1$ and $R^2$ correspond to $R^1$ and $R^2$ in the formula (4), respectively.

That is to say, in the above formula (17), $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

The 5-halomethyl-1,3-dioxolan-4-one derivative represented by the above formula (4) can be synthesized, for example, by reacting the compound represented by the above formula (17) with β-halolactic acid such as β-bromolactic acid or β-chlorolactic acid, or an ester thereof. This reaction is preferably carried out at a reaction temperature within a range of 20° C. to a reflux temperature under conditions in which either the compound represented by the above formula (17), or a β-halolactic acid or an ester thereof is in an excessive amount. This reaction is preferably carried out using an acid catalyst such as a Lewis acid. When β-halolactic acid is used, however, the reaction can sufficiently progress with its acidity. Moreover, the reaction may be carried out with no solvents, or it may be carried out using a nonpolar organic solvent. The reaction can be carried out in either a homogeneous system, or a heterogeneous system.

Furthermore, the 5-halomethyl-1,3-dioxolan-4-one derivative represented by the above formula (4) can also be synthesized by reacting the compound represented by the above formula (17) with a orthoformic acid trimethyl ester to obtain a dimethoxy form or an enol ether form, and then reacting the obtained compound with a β-halolactic acid. The reaction between the dimethoxy form and the β-halolactic acid is preferably carried out at a reaction temperature within a range of 20° C. to a reflux temperature under conditions in which either the dimethoxy form or the enol ether form, or the β-halolactic acid is in an excessive amount. This reaction is preferably carried out using an acid catalyst such as a Lewis acid. When β-halolactic acid is used, however, the reaction can sufficiently progress with its acidity. Moreover, this reaction may be carried out with no solvents, or it may be carried out using a nonpolar organic solvent. The reaction can be carried out in either a homogeneous system, or a heterogeneous system.

Examples of a pattern of the reaction may include a closed system in which the reaction is carried out under reduced pressure, under ordinary pressure or under increased pressure, using a well-closed container; and a reflux system in which the reaction is carried out at a boiling point or lower and a volatilized raw material, product and solvent are refluxed with a condenser. These reactions are preferably carried out using a Dienstark or a decanter to remove the generated water or alcohol to the outside of the system.

Moreover, an optically active β-halolactic acid, ketone or aldehyde can also be used in the reaction to form the derivative represented by the above formula (4). In this case, the obtained derivative represented by the above formula (4) has optical activity that is derived from the raw material.

Furthermore, a racemic mixture may also be used. In this case, the obtained derivative represented by the above formula (4) becomes a racemic mixture.

Where $R^1$ differs from $R^2$ in the derivative represented by the above formula (4), the carbon atom at position 2 becomes an asymmetric carbon, and optical isomers exist. These optical isomers can be isolated by a known optical resolution method such as the preferential crystallization method or the use of an optical resolution column. These optically active substances may be either an (R)-form or a (S)-form, or may be a mixture of the (R)-form and the (S)-form, and all of these substances can be used.

II. Production method of the 5-methylene-1,3-dioxolane-4-one derivative of the Present Invention As stated above, the 5-methylene-1,3-dioxolan-4-one derivative represented by the above formula (1) can be produced by reacting the 5-halo-5-methyl-1,3-dioxolnae-4-one derivative represented by the above formula (2) or the 5-halomethyl-1,3-dioxolan-4-one derivative represented by the above formula (4) with the amide compound represented by the above formula (5) so as to carry out a dehydrohalogenation reaction.

Conventionally, a base has been used in such a dehydrohalogenation reaction. Representative examples of such a base may include: alkali metal hydroxides such as lithium hydroxide, sodium hydroxide or potassium hydroxide; alkali metal alkoxides such as sodium methoxide, sodium ethoxide, sodium-tert-butoxide or potassium-tert-butoxide; alkali metal carboxylates such as sodium acetate; and amines such as trimethylamine, triethylamine, trioctylamine, pyridine, collidine, 1,5-diazabicyclo[4.3.0]-5-nonene, 1,8-diazabicyclo[5.4.0]-7-undecene or 1,4-diazabicyclo[2.2.2]octane. However, when the dehydrohalogenation reaction of the derivative represented by the above formula (2) or the derivative represented by the above formula (4) is conducted using these bases, a decomposition reaction progresses, and thus, little derivative represented by the above formula (1) of interest can be obtained. Moreover, when these bases are used, there may be problems in that the reaction solution becomes brown or in that crystallization of the derivative represented by the above formula (1) of interest is significantly inhibited, thereby making purification after the reaction difficult.

In the present invention, the dehydrohalogenation reaction of the derivative represented by the above formula (2) or the derivative represented by the above formula (4) is carried out using the amide compound represented by the above formula (5) as a base, so as to overcome the above problems. The amide compound represented by the above formula (5) has an extremely low basicity, and therefor it is not generally used as a dehydrohalogenating reagent. However, in the present invention, the dehydrohalogenation reaction progresses extremely efficiently with the amide compound.

Moreover, when the above base which is conventionally used and the amide compound represented by the above formula (5) are used in combination, there are some cases where the decomposition caused by the above base which is conventionally used can be prevented. However, there may still be problems in that the reaction solution becomes brown or in that crystallization of the derivative represented by the above formula (1) of interest is significantly inhibited, thereby making purification after the reaction difficult.

A method of producing the 5-methylene-1,3-dioxolan-4-one derivative represented by the above formula (1) of the present invention will be explained. In the present invention, an amide compound represented by the following formula (5) is used as a base:

(5)

In formula (5), each of $R^3$, $R^4$ and $R^5$ independently represents a hydrogen atom, or a linear or branched alkyl group containing 1 to 4 carbon atoms. $R^3$, $R^4$ and $R^5$ may be identical or may be different. Examples of $R^5$, $R^6$ and $R^7$ in the formula (5) may include a hydrogen atom, a methyl group, an ethyl group, a propyl group, an isopropyl group, a butyl group, a tert-butyl group, and a 2-ethylhexyl group.

In terms of smooth progression of the reaction, N-methylformamide, N-ethylformamide, N,N-dimethylformamide, N,N-diethylformamide and the like are preferable as the amide compound represented by the above formula (5). In terms of yield after purification, N,N-dimethylformamide is more preferable. The amide compound represented by the formula (5) may be used singly or in combination of two or more types.

In terms of yield, the use amount of the amide compound represented by the above formula (5) is preferably-0.1 mole or more, more preferably 0.5 mole or more, particularly preferably 1 mole or more, and still more preferably 5 mole or more based on 1 mole of the derivative represented by the formula (2) or (4). In addition, in terms of disposal of the waste liquid after the reaction, the use amount of the amide compound represented by the above formula (5) is preferably 100 mole or less, more preferably 50 mole or less, and particularly preferably 30 mole or less based on 1 mole of the derivative represented by the formula (2) or (4).

In the dehydrohalogenation reaction of the present invention, an organic solvent can be used, also. Examples of an organic solvent used herein may include hydrocarbon solvent such as pentane, hexane, heptane, octane, isooctane, cyclopentane, cyclohexane, benzene, and toluene; alcohol solvent such as methanol, ethanol, n-propylalcohol, isopropylalcohol, n-butylalcohol, sec-butylalcohol, tert-butylalcohol, isobutylalcohol, n-amylalcohol, isoamylalcohol, n-hexylalcohol, n-heptylalcohol, n-octylalcohol, n-nonylalcohol, n-decylalcohol, laurylalcohol, cetylalcohol, stearylalcohol, benzylalcohol, triphenylcarbinol, ethyleneglycol, 1,2-propanediol, 1,3-propanediol, 1,4-butanediol, cresol, phenol, and xylenol; ether solvent such as diethylene glycol dimethyl ether, diethylene glycol diethyl ether, triethylene glycol dimethyl ether, triethylene glycol diethyl ether, tetrahydrofuran, diethyl ether, diisopropyl ether, and methyl-tert-butyl ether; and chlorine-containing solvent such as carbon tetrachloride, chloroform, and methylene chloride. Such an organic solvent may be used singly or in combination of two or more types.

Of these, a solvent having low polarity and low mutual solubility with the amide compound represented by the above formula (5), such as pentane, hexane, heptane, octane, isooctane, cyclopentane, cyclohexane, benzene, toluene, diethyl ether, diisopropyl ether or methyl-tert-butyl ether, is preferably used. When only a little derivative represented by the above formula (1) is dissolved in the amide compound represented by the above formula (5), the major part of the derivative represented by the above formula (1) exists in a solvent having low polarity. So, in this case, a product of interest can be efficiently recovered by separating the liquid after the completion of the reaction.

In terms of reaction rate and the amount of the waste solvent, the use amount of an organic solvent is preferably 100 times by mass or less, more preferably 50 times by mass or less, and particularly preferably 20 times by mass or less based on the derivative represented by the formula (2) or (4).

Alternatively, it may also be possible to carry out the dehydrohalogenation reaction without using a solvent and then to extract the derivative represented by the above formula (1) of interest with a solvent having low polarity. A small amount of the amide compound represented by the above formula (5) is contained in such a solvent having low polarity. However, the amide compound can be easily removed by washing with water.

Otherwise, it may also be possible to carry out the reaction without using a solvent, and then to add the reaction solution to a large amount of water, so that the derivative represented by the above formula (1) of interest is deposited.

In general, the reaction temperature is preferably set within the range of –30° C. to 120° C. In terms of reaction rate, the reaction temperature is more preferably 0° C. or higher, and particularly preferably 10° C. or higher. Moreover, in terms of prevention of a decomposition reaction, the reaction temperature is more preferably 60° C. or lower, and particularly preferably 40° C. or lower.

Conventionally, since a dehydrohalogenation reaction causes heat generation, a base is added thereto while cooling. However, when the amide compound represented by the above formula (5) is used as a base in the present invention, only a little heat is generated, and almost no decomposition reaction progresses even at a high temperature. Accordingly, it is not necessary to cool in the present invention.

Examples of a pattern of the dehydrohalogenation reaction may include a closed system in which the reaction is carried out under reduced pressure, under ordinary pressure or under increased pressure, using a well-closed container; and a reflux system in which the reaction is carried out at a boiling point or lower and a volatilized raw material, product and solvent are refluxed with a condenser.

The reaction time may be determined, taking into consideration the reaction temperature or the like. Generally, the reaction time is preferably about 1 to 48 hours.

In the present invention, when a dehydrohalogenation reaction is carried out, a polymerization inhibitor may be added to the reaction solution, if necessary.

The polymerization inhibitor is not particularly limited, and examples of it may include a quinone-based polymerization inhibitor such as hydroquinone, methoxyhydroquinone, benzoquinone, and p-tert-butylcatechol; an alkylphenol-based polymerization inhibitor such as 2,6-di-tert-butylphenol, 2,4-di-tert-butylphenol, 2-tert-butyl-4,6-dimethylphenol, 2,6-di-tert-butyl-4-methylphenol, and 2,4,6-tri-tert-butylphenol; an amine-based polymerization inhibitor such as alkylated diphenylamine, N,N'-diphenyl-p-phenylenediamine, and phenothiazine; and a copper dithiocarbamate-based polymerization inhibitor such as copper dimethyldithiocarbamate, copper diethyldithiocarbamate, and copper dibutyldithiocarbamate. The polymerization inhibitor may be used singly or in combination of two or more types.

The additive amount of a polymerization inhibitor is preferably 5% or less by mass, more preferably 1% or less by mass, and particularly preferably 0.1% or less by mass based on the mass of the derivative represented by the formula (2) or (4).

In the present invention, a dehydrohalogenation reaction is carried out as described above, so as to produce the derivative represented by the above formula (1). In the present reaction, the product of interest can be obtained at a good yield while sufficiently preventing a side reaction. Accordingly, the derivative represented by the above formula (1) can be obtained at a high purity by a simple operation. The purification methods may include a known method such as recrystallization, washing with water or an organic solvent, solvent fractionation, column chromatography, distillation or short-path distillation.

Where $R^1$ differs from $R^2$ in the derivative represented by the above formula (1), the carbon atom at position 2 becomes an asymmetric carbon, and optical isomers exist. These optical isomers can be isolated by a known optical resolution method such as preferential crystallization method or the use of an optical resolution column. These optically active substances may be either an (R)-form or a (S)-form, or may be a mixture of the (R)-form and the (S)-form, and all of these substances can be used as raw material monomers for a component resin of a coating material, an adhesive, an agglutinant, a resin for ink, a resist or the like.

5. The First and Second Polymers of the Present Invention

Next, the first and second polymers of the present invention will be explained. The first and second polymers of the present invention are preferably used, for example, for a resist composition, and particularly for a chemically amplified resist composition.

I. The First Polymer of the Present Invention

The first polymer of the present invention is obtained by (co)polymerizing a monomer composition comprising the monomer represented by the above formula (1), and it comprises at least one of constitutional units represented by the formula (6) indicated below. The proportion of the constitutional unit represented by the following formula (6) in the polymer is preferably 5 mol % or more.

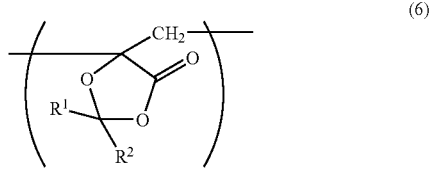

(6)

In formula (6), $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound.

Herein, the alkyl group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the bridged cyclic hydrocarbon group have two or more substituents, the substituents may be of either a single type, or two or more types.

$R^1$ and $R^2$ in the formula (6) correspond to $R^1$ and $R^2$ in the formula (1), respectively. Accordingly, the $R^1$ and $R^2$ in the formula (6) are the same as the $R^1$ and $R^2$ in the formula (1), and preferred examples of $R^1$ and $R^2$ in the formula (6) are also the same as the preferred examples of $R^1$ and $R^2$ in the formula (1).

The first polymer of the present invention may be a homopolymer consisting of one type of the monomer represented by the above formula (1), a copolymer consisting of two or more types of the monomer represented by the above formula (1), or a copolymer consisting of at least one type of the monomer represented by the above formula (1) and at least one type of monomers other than the monomer represented by the above formula (1). When the first polymer of the present invention is a copolymer, each constitutional unit can have any given sequence. Accordingly, this polymer may be a random copolymer, an alternating copolymer, or a block copolymer.

In the present invention, at least one type of the monomer represented by the above formula (1) may be copolymerized with at least one type of known monomers other than the above monomer. Examples of a monomer capable of being copolymerized may include those that are conventionally known as a positive resist, a negative resist, an anti-reflection coat material or an insulating film-forming material. For example, the monomer capable of being copolymerized may include a known monomer such as an acrylic acid derivative and a methacrylic acid derivative, which have a dry etching resistance-improving group or a soluble group involving acid dissociation, a carboxylic acid (including a derivative thereof) having an ethylene double bond causing alkali solubility, and known monomers used in the production of an acrylic resin.

Examples of an acrylic acid derivative may include acryl ester in which the hydroxyl group of the carboxy group is protected with an acid-dissociating substituent, such as tert-butyl acrylate, tetrahydropyranyl acrylate, tetrahydrofuranyl acrylate, 1-methylcyclohexyl acrylate, 1-methyladamantyl acrylate, ethoxyethyl acrylate, ethoxypropyl acrylate, and the ester of acrylic acid and 2-hydroxy-3-pinanone; or acryl ester in which the hydroxyl group of the carboxy group is protected with an non-acid-dissociating substituent, such as adamantyl acrylate, cyclohexyl acrylate, naphthyl acrylate, benzyl acrylate, 3-oxocyclohexyl acrylate, bicyclo[2.2.1]heptyl acrylate, tricyclodecanyl acrylate, the ester of acrylic acid and terpineol, and the ester of acrylic acid and 3-bromoacetone.

Examples of a methacrylic acid derivative may include methacrylic acid derivatives corresponding to the above listed acrylic acid derivatives.

In addition, examples of a carboxylic acid having an ethylene double bond may include acrylic acid; methacrylic acid; maleic acid; fumaric acid; norbornene or a norbornene derivative having an alkyl group, an alkyloxy group, a hydroxyl group, a hydroxyalkyl group, a carboxy group, an alkyloxycarbonyl group, or the like as a substituent; a vinyl ether derivative such as ethyl vinyl ether, cyclohexyl vinyl ether, and hydroxyethyl vinyl ether; a styrene derivative such as styrene, p-hydroxystyrene, p-methoxystyrene, and p-tert-butoxystyrene; and maleic anhydride.

Examples of a known monomer used in the production of an acrylic resin may include acrylic acid; methacrylic acid; or an acrylic acid derivative or an methacrylic acid derivative in which the hydrogen atom of these carboxylic acids is substituted with a group such as a methyl group, an ethyl group, a n-propyl group, an isopropyl group, a n-butyl group, a tert-butyl group, a n-hexyl group, an octyl group, a 2-ethylhexyl group, a lauryl group, a 2-hydroxyethyl group, a 2-hydroxypropyl group, a cyclopentyl group, a cyclohexyl group, a 2-hydroxyethyl group, a norbornyl group, a tricyclodecanyl group, an adamantyl group, a 2-methyl-2-adamantyl group, a tetrahydropyranyl group, a tetrahydrofuranyl group, or the like.

The first polymer of the present invention is preferably used as a material for a resist composition, and particularly as a material for a chemically amplified resist composition. Hereinafter, a case where the first polymer of the present invention is a resin used for a chemically amplified resist composition will be explained.

The resin for a chemically amplified resist composition is required to have both a property for becoming soluble in an alkaline aqueous solution by an acid so as to realize high sensitivity and a structure having high carbon density so as to realize high dry etching resistance. The first polymer of the present invention is excellent in solubility in an organic solvent and heat resistance, and has little line edge roughness. When a structure having a property for becoming soluble in an alkaline aqueous solution by the action of an acid, or a structure having high dry etching resistance is introduced into such a polymer, an excellent resin for a chemically amplified resist composition can be obtained.

Examples of the structure having a functional group that is easily eliminated by the action of an acid may include a structure in which a hydroxy group or a carboxy group is protected with an acyl group such as an acetyl group, a tert-butyl group, a tetrahydropyranyl group, a 2-methyl-2-adamantyl group or other groups is.

Examples of the structure having high carbon density may include an isobornyl group, an adamantly group, a 2-methyl-adamantyl group, a 3-hydroxy-1-adamantyl group, a tricyclodecanyl group, and dicyclopentadienyl group.

In order to introduce the structure having a functional group that is easily eliminated by the action of an acid or the structure having high carbon density into the polymer, the monomer of the present invention may be copolymerized with a monomer having such a structure.

As a monomer having such a structure, for example, the one that is known as a raw material monomer for a resin for a chemically amplified resist composition can be used. A raw material monomer used for the polymer of the present invention is arbitrarily selected depending on light source used in lithography.

For example, when a KrF excimer laser or an electron beam is used as a light source, considering its high etching resistance, a polymer obtained by copolymerizing the monomer of the present invention with p-hydroxystyrene or a derivative thereof is preferably used. In this case, the proportion of the constitutional unit derived from the monomer of the present invention in the polymer is preferably 5% or more and is preferably 60% or less.

When an ArF excimer laser is used as a light source, a polymer obtained by copolymerizing the monomer of the present invention with a monomer having a cyclic hydrocarbon group is preferably used. Copolymerization with a monomer having a cyclic hydrocarbon group enables high etching resistance.

Among them, a polymer obtained by copolymerizing the monomer of the present invention, a monomer having a cyclic hydrocarbon group, a monomer having a hydrophilic functional group and/or a monomer having a lactone structure is preferable.

It is known that an acrylic copolymer obtained by copolymerizing a monomer having a cyclic hydrocarbon group and a monomer having a hydrophilic functional group, or an acrylic copolymer obtained by copolymerizing a monomer having a cyclic hydrocarbon group and a monomer having a lactone structure, is preferable as a resin for the ArF excimer laser lithography. Introduction of the monomer unit of the present invention into these polymers enables improvement of solubility in an organic solvent and heat resistance without impairing the resist performance such as high sensitivity, high resolution or high dry etching resistance, thereby providing an excellent resist pattern with only a little line edge roughness.

A monomer unit having a cyclic hydrocarbon group imparts high dry etching resistance to a polymer comprising the same. In particular, a monomer unit having a protecting group that is eliminated by an acid (a cyclic hydrocarbon group may also be a protecting group by itself) imparts also high sensitivity to the polymer comprising the same in photolithography using an ArF excimer laser with a wavelength of 193 nm. The monomer units having a cyclic hydrocarbon group may be of either a single type, or two or more types, if necessary.

Preferred examples of the monomer unit having a cyclic hydrocarbon group may include cyclohexyl (meth)acrylate, isobornyl (meth)acrylate, adamantyl (meth)acrylate, tricyclodecanyl (meth)acrylate, dicyclopentyl (meth)acrylate, and derivatives having a substituent such as an alkyl group, a hydroxy group or a carboxy group on the cyclic hydrocarbon group of these monomers.

Specific examples of such a monomer unit may include 1-isobornyl (meth)acrylate, 2-(meth)acryloyloxy-2-methyladamantane, 2-(meth)acryloyloxy-2-ethyladamantane, 1-(meth)acryloyloxy-3-hydroxyadamantane, cyclohexyl (meth)acrylate, adamantyl (meth)acrylate, tricyclodecanyl (meth)acrylate, and dicyclopentyl (meth)acrylate.

A monomer unit having a hydrophilic functional group imparts adhesion to a substrate to a polymer comprising the same. In particular, a monomer unit having a protecting group that is eliminated by an acid imparts also high sensitivity to the polymer comprising the same in photolithography using an ArF excimer laser with a wavelength of 193 nm. Examples of a hydrophilic functional group may include a terminal hydroxy group, an alkyl-substituted ether group, a 6-valerolactonyl group, and a γ-butyrolactonyl group. It should be noted that some of the above listed hydrophilic functional groups are generally included in hydrophobic groups. However, since even such functional groups have hydrophilicity that is needed in the present invention, they are herein defined as a hydrophilic functional group. The monomer units having a hydrophilic functional group may be of either a single type, or two or more types, if necessary.

Preferred examples of the monomer unit having a hydrophilic functional group may include (meth)acrylate having a terminal hydroxy group, (meth)acrylate having an alkyl-substituted ether group, (meth)acrylate having a δ-valerolactonyl group, (meth)acrylate having a γ-butyrolactonyl group, and derivatives having a substituent such as an alkyl group, a hydroxy group or a carboxy group on the hydrophilic functional group of these monomers.

Specific examples of such a monomer unit may include 2-hydroxyethyl (meth)acrylate, 2-hydroxypropyl (meth)acrylate, 4-hydroxybutyl (meth)acrylate, 2-methoxyethyl (meth)acrylate, 2-ethoxyethyl (meth)acrylate, β-(meth)acryloyloxy-β-methyl-δ-valerolactone, β-(meth)acryloyloxy-γbutyrolactone, β-(meth)acryloyloxy-β-methyl-γ-butyrolactone, α-(meth)acryloyloxy-γ-butyrolactone, 2-(1-(meth)acryloyloxy)ethyl-4-butanolide, pantolactone (meth)acrylate, and a mixture of 8-methacryloyloxy-3-oxatricyclo[5.2.1.0$^{2,6}$]decan-2-one and 9-methacryloyloxy-3-oxatricyclo[5.2.1.0$^{2,6}$]decan-2-one.

A monomer unit having a lactone structure imparts high dry etching resistance and adhesion to a substrate to a polymer comprising the same. The monomer units having a lactone structure may be of either a single type, or two or more types, if necessary.

Preferred examples of the monomer unit having a lactone structure may include 4-8 membered α-methylenelactone, and derivatives having a substituent such as an alkyl group, a hydroxy group or a carboxy group on a carbon of the lactone ring of these monomers. In particular, α-methylene-γ-butyrolactone, and the derivative having a substituent such as an alkyl group, a hydroxy group or a carboxy group on the carbon of the γ position are preferable.

Specific examples of such a monomer unit may include 2-methylene-4-butanolide, 4-methyl-2-methylene-4-butanolide, 4-ethyl-2-methylene-4-butanolide, and 4,4-dimethyl-2-methylene-4-butanolide.

Among them, as a resin for a chemically amplified resist composition, a polymer comprising at least one of constitutional units represented by the formula (6) and at least one of constitutional units represented by the formula (8), (9) or (10) is preferable. Such a polymer comprising at least one of constitutional units represented by the formula (6) and at least one of constitutional units represented by the formula (8), (9) or (10) will be described in the section 11. The second polymer of the present invention.

The mass-average molecular weight of the first polymer of the present invention is not particularly limited. However, when the polymer is used as a resin for a resist composition, the mass-average molecular weight of the first polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

II. The Second Polymer of the Present Invention

The second polymer of the present invention comprises at least one of constitutional units represented by the following formula (7) and at least one of constitutional units represented by the following formula (8), (9) or (10):

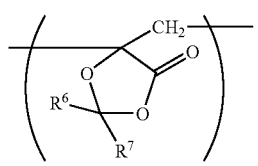

(7)

In formula (7), each of $R^6$ and $R^7$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^6$ and $R^7$ represent a cyclic hydrocarbon group containing 4 to 16 carbon atoms together with the carbon atom to which they are bound. $R^6$ and $R^7$ may be identical or may be different.

Herein, the alkyl group and the cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon-atoms, an alkoxy group containing 1 to 6 carbon atoms, and a carboxy group esterified with an alcohol containing 1 to 6 carbon atoms. When the alkyl group and the cyclic hydrocarbon group have two or more substituents, the substituents may be of either a single type, or two or more types.

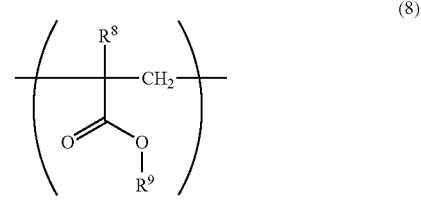

(8)

In formula (8), $R^8$ represents a hydrogen atom or a methyl group, and $R^9$ represents a linear or branched alkyl group containing 1 to 6 carbon atoms, a cyclic hydrocarbon group containing 4 to 8 carbon atoms, or a bridged cyclic hydrocarbon group containing 4 to 16 carbon atoms.

Herein, the alkyl group, the cyclic hydrocarbon group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms. When the alkyl group, the cyclic hydrocarbon group and the bridged cyclic hydrocarbon group have two or more substituents, the substituents may be of either a single type, or two or more types.

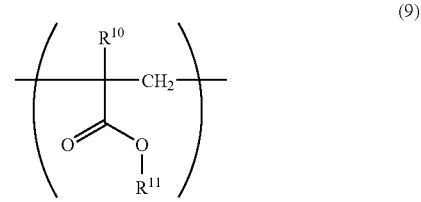

(9)

In formula (9), $R^{10}$ represents a hydrogen atom or a methyl group, and $R^{11}$ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group.

Herein, the alkyl group, the cyclic hydrocarbon group, the bridged cyclic hydrocarbon group and the hydrophilic functional group may be unsubstituted, or may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms. When the alkyl group, the cyclic hydrocarbon group, the bridged cyclic hydrocarbon group and the hydrophilic functional group have two or more substituents, the substituents may be of either a single type, or two or more types.

Examples of a hydrophilic functional group in the formula (9) may include groups with high polarity, such as a hydroxyl group, a carboxy group or an amino group; linear or branched alkyl groups having a structure such as ketone, acid anhydride, ester, ether, lactone, imide or amide; and cyclic compounds. Compounds having a hydrophilic functional group may include monocyclic saturated hydrocarbon groups containing 4 to 8 carbon atoms or a bridged cyclic hydrocarbon groups containing 4 to 16 carbon atoms, a portion of the skeleton of which is substituted with a structure such as ketone, acid anhydride, ester, ether, lactone, imide or amide. Some of the above listed hydrophilic functional groups are generally included in hydrophobic groups. However, since even such functional groups have hydrophilicity that is needed for a resist composition of the present invention, they are herein defined as a hydrophilic functional group.

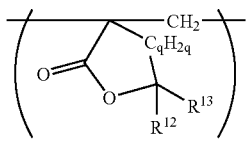

(10)

In formula (10), each of $R^{12}$ and $R^{13}$ independently represents a hydrogen atom, a methyl group or an ethyl group, and q represents an integer of 1 to 4. $R^{12}$ and $R^{13}$ may be identical or may be different.

Herein, $C_qH_{2q}$ represents a methylene chain containing 1 to 4 carbon atoms [—$(CH_2)_q$— (wherein q represents an integer of 1 to 4)].

In the second polymer of the present invention, the constitutional units (7), (8), (9) and (10) are not necessarily of the same type, but two or more types may be mixed therein as long as they are represented by the above general formulas. Moreover, in this polymer, each constitutional unit can have any given sequence. Accordingly, this polymer may be a random copolymer, an alternating copolymer, or a block copolymer.

Examples of a substituent on the linear or branched alkyl group containing 1 to 6 carbon atoms that is the substituent on the alkyl group, the cyclic hydrocarbon group, the bridged cyclic hydrocarbon group and the hydrophilic functional group, may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

Examples of $R^6$ and $R^7$ in the above formula (7) may include a hydrogen atom, a methyl group, an ethyl group, a propyl group, an isopropyl group, a butyl group, a tert-butyl group, a cyclopentyl group, a cyclohexyl group, a cycloheptyl group, a 2-norbornyl group, a 1-adamantyl group, a 1-adamantanemethyl group, a 1-adamantaneethyl group, a 2-adamantyl group, a 2-adamantanemethyl group, a 2-adamantaneethyl group and a 2-adamantanonyl group. Moreover, $R^6$ and $R^7$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Moreover, $R^6$ and $R^7$ in the above formula (7) may form a cyclic hydrocarbon structure containing 4 to 16 carbon atoms, together with the carbon atom to which they are bound. Examples of such a cyclic hydrocarbon structure may include an adamantylidene group, a norbornylidene group, and a cyclohexylidene group. Furthermore, examples of such a cyclic hydrocarbon structure may also include those wherein the cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the structure has two or more substituents, the substituents may be of either a single type, or two or more types.

As the constitutional unit represented by the above formula (7), a constitutional unit wherein $R^6$ represents a hydrogen atom, a methyl group or an ethyl group and $R^7$ represents a cyclopentyl group, a cyclohexyl group or a cycloheptyl group, and a constitutional unit wherein $R^6$ and $R^7$ form a cyclic hydrocarbon group containing 5 to 8 carbon atoms together with the carbon atom to which they are bound, are preferable. Among them, the constitutional unit represented by the above formula (6) is particularly preferable.

The constitutional unit represented by the above formula (8) is obtained by copolymerizing a monomer such as cyclohexyl (meth)acrylate, 1-isobornyl (meth)acrylate, adamantyl (meth)acrylate, tricyclodecanyl (meth)acrylate, dicyclopentyl (meth)acrylate, 2-(meth)acryloyloxy-2-methyladamantane, 2-(meth)acryloyloxy-2-ethyladamantane, or derivatives having a substituent such as an alkyl group, a hydroxy group or a carboxy group on the cyclic hydrocarbon group of these monomers.

In terms of sensitivity and resolution when the polymer is used as a resist composition material, a constitutional unit derived from 2-(meth)acryloyloxy-2-methyladamantane, and a constitutional unit derived from 2-(meth)acryloyloxy-2-ethyladamantane are preferable, as the constitutional unit represented by the above formula (8).

The constitutional unit represented by the above formula (9) is obtained by copolymerizing a monomer having a hydrophilic functional group, such as (meth)acrylate having a terminal hydroxy group, (meth)acrylate having an alkyl-substituted ether group, (meth)acrylate having a δ-valerolactonyl group, or (meth)acrylate having a γ-butyrolactonyl group; derivatives having a substituent such as an alkyl group, a hydroxy group or a carboxy group on the hydrophilic functional group of these monomers; or a monomer having a hydrophilic functional group such as a hydroxy group or a carboxy group on the cyclic hydrocarbon group of a monomer such as cyclohexyl (meth)acrylate, 1-isobornyl (meth)acrylate, adamantyl (meth)acrylate, tricyclodecanyl (meth)acrylate, dicyclopentyl (meth)acrylate, 2-(meth)acryloyloxy-2-methyladamantane or 2-(meth)acryloyloxy-2-ethyladamantane. Specific examples of such a monomer may include 2-hydroxyethyl (meth)acrylate, 2-hydroxypropyl (meth)acrylate, 4-hydroxybutyl (meth)acrylate, 2-methoxyethyl (meth)acrylate, 2-ethoxyethyl (meth)acrylate, 1-methacryloyloxy-3-hydroxyadamantane, β-(meth)acryloyloxy-β-methyl-β-valerolactone, β-(meth)acryloyloxy-γ-butyrolactone, β-(meth)acryloyloxy-β-methyl-γ-butyrolactone, α-(meth)acryloyloxy-γ-butyrolactone, 2-(1-(meth)acryloyloxy)ethyl-4-butanolide, pantolactone (meth)acrylate, 8-methacryloyloxy-3-oxatricyclo[5.2.1.0$^{2,6}$]decan-2-one, and 9-methacryloyloxy-3-oxatricyclo[5.2.1.0$^{2,6}$]decan-2-one.

In terms of adhesion to a substrate when the polymer is used as a resist composition material, a constitutional unit derived from 1-methacryloyloxy-3-hydroxyadamantane, a constitutional unit derived from 8-methacryloyloxy-3-oxatricyclo[5.2.1.0$^{2,6}$]decan-2-one, and a constitutional unit derived from 9-methacryloyloxy-3-oxatricyclo[5.2.1.0$^2$-6] decan-2-one are preferable, as the constitutional unit represented by the above formula (9).

The constitutional unit represented by the above formula (10) is obtained by copolymerizing a monomer such as 4-8 membered α-methylenelactone, or derivatives having a substituent such as an alkyl group, a hydroxy group or a carboxy group on a carbon of the lactone ring of these monomers.

In terms of sensitivity and resolution when the polymer is used as a resist composition material, a constitutional unit derived from α-methylene-γ-butyrolactone, and a constitutional unit derived from its derivatives having a substituent such as a methyl group or an ethyl group on the carbon of the γ position, for example, α-methyleney-butyrolactone, α-methylene-γ-methyl-γ-butyrolactone, α-methylene-γ-ethyl-γ-butyrolactone, and 4,4-dimethyl-2-methylene-4-butanolide, are preferable, as the constitutional unit represented by the above formula (10).

In order to improve solubility of the polymer in an organic solvent and heat resistance and to reduce line edge roughness, the proportion of the constitutional unit represented by the above formula (7) is preferably 5 mol % or more in the polymer. Moreover, in order not to reduce sensitivity and resolution, the proportion of the constitutional unit represented by the above formula (7) is preferably 50 mol % or less in the polymer.

In order to improve sensitivity and resolution, the proportion of the constitutional unit represented by the above formula (8) is preferably 30 mol % or more in the polymer. Moreover, in order not to reduce solubility of the polymer in an organic solvent, the proportion of the constitutional unit represented by the above formula (8) is preferably 70 mol % or less in the polymer.

In order not to reduce dry etching resistance, the proportion of the constitutional unit represented by the above formula (9) is preferably 70 mol % or less in the polymer.

In order not to reduce sensitivity and resolution, the proportion of the constitutional unit represented by the above formula (10) is preferably 60 mol % or less in the polymer.

The second polymer of the present invention is preferably used as a material for a resist composition, and particularly as a material for a chemically amplified resist composition. The second polymer of the present invention is particularly excellent in sensitivity, resolution, and the like.

Moreover, the second polymer of the present invention may comprise at least one type of constitutional units derived from known monomers other than the constitutional units represented by the above formulas (7) to (10). Specific examples of a monomer capable of being copolymerized or a constitutional unit may be the same as those described in the first polymer of the present invention.

The mass-average molecular weight of the second polymer of the present invention is not particularly limited. However, when the polymer is used as a resin for a resist composition, the mass-average molecular weight of the second polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

5. The Third, Fourth and Fifth Polymers of the Present Invention

Next, the third, fourth and fifth polymers of the present invention will be explained. The third, fourth and fifth polymers of the present invention are preferably used, for example, for a resist composition, and particularly for a chemically amplified resist composition.

I. The Third Polymer of the Present Invention

The third polymer of the present invention comprises at least one of constitutional units represented by the formula (11) indicated below. The proportion of the constitutional unit represented by the following formula (11) in the polymer is preferably 5 mol % or more.

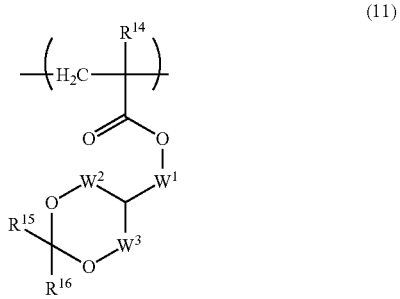

(11)

In formula (11), $W^1$ represents a direct bond or a methylene chain containing 1 to 6 carbon atoms [—$(CH_2)_k$— (wherein k represents an integer of 0 to 6)], $W^2$ represents a direct bond or a methylene chain containing 1 to 3 carbon atoms [—$(CH_2)_l$— (wherein l represents an integer of 0 to 3)], $W^3$ represents a methylene chain containing 1 to 3 carbon atoms [—$(CH_2)_m$— (wherein m represents an integer of 1 to 3)], $R^{14}$ represents a hydrogen atom or a methyl group, $R^{15}$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent, $R^{16}$ represents a hydrogen atom, or a linear or branched alkyl group containing 1 to 6 carbon atoms; or $R^{15}$ and $R^{16}$ represent a bridged cyclic hydrocarbon group containing 4 to 16 carbon atoms together with the carbon atom to which they are bound.

Herein, the methylene chain containing 1 to 6 carbon atoms may have, as a substituent, an alkyl group containing 1 to 3 carbon atoms which may be optionally substituted, and may optionally have at least one ether bond therein. The methylene chain containing 1 to 3 carbon atoms may have a carbonyl group therein. Further, the alkyl group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the bridged cyclic hydrocarbon group have two or more substituents, the substituents may be of either a single type, or two or more types.

Examples of a substituent on the linear or branched alkyl group containing 1 to 6 carbon atoms that is the substituent on the alkyl group and the bridged cyclic hydrocarbon group may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

Herein, the bridged cyclic hydrocarbon group is a group having a structure represented by the following formula (15) or (16) including adamantane and norbornane as typical examples:

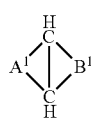

(15)

wherein each of $A^1$ and $B^1$ represents a linear or branched alkylene group, and $A^1$ and $B^1$ may be identical or may be different; or

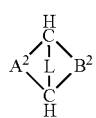

(16)

wherein each of $A^2$, $B^2$ and L represents a linear or branched alkylene group, and $A^2$, $B^2$ and L may be identical or may be different.

Examples of $W^1$ in the above formula (11) may include a direct bond (which means that the oxygen atom and the carbon atom that are adjacent to $W^1$ are directly bound to each other), $CH_2$, $CH_2CH_2$, $CH_2CH_2CH_2$, $CH(CH_3)CH_2$, $CH_2O$, $CH_2CH_2O$, $CH_2CH(CH_3)O$, $CH(CH_3)CH_2O$, $CH_2CH_2OCH_2CH_2O$, $CH_2CH(CH_3)OCH_2CH(CH_3)O$, and $CH(CH_3)CH_2OCH(CH_3)CH_2O$.

Of these, in terms of storage stability of the polymer, a direct bond, $CH_2$, $CH_2CH_2O$ and $CH_2CH(CH_3)O$ are preferable as $W^1$.

Examples of $W^2$ in the above formula (11) may include a direct bond (which means that the oxygen atom and the carbon atom that are adjacent to $W^2$ are directly bound to each other), $CH_2$, $C(O)$, $CH_2CH_2$, $CH_2C(O)$, $CH_2CH_2CH_2$, and $CH_2C(O)CH_2$.

Of these, in terms of storage stability of the polymer, a direct bond, $CH_2$, $C(O)$ and $CH_2C(O)$ are preferable as $W^2$.

Examples of $W^3$ in the above formula (11) may include $CH_2$, $C(O)$, $CH_2CH_2$, $CH_2C(O)$, $CH_2CH_2CH_2$, and $CH_2C(O)CH_2$.

Of these, in terms of storage stability of the polymer, $CH_2$, $C(O)$ and $CH_2C(O)$ are preferable as $W^3$.

Examples of $R^{15}$ in the above formula (11) may include bridged cyclic hydrocarbon groups such as a 2-norbornyl group, a 1-adamantyl group, a 1-adamantanemethyl group, a 1-adamantaneethyl group, a 2-adamantyl group, a 2-adamantanemethyl group, a 2-adamantaneethyl group or a 2-adamantanonyl group. Moreover, examples of $R^{15}$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Of these, in terms of having excellent dry etching resistance when the polymer is used for a resist composition, a 2-norbornyl group, a 1-adamantyl group, a 1-adamantanemethyl group, a 1-adamantaneethyl group, a 2-adamantyl group, a 2-adamantanemethyl group and a 2-adamantaneethyl group are preferable as $R^{15}$. In terms of the light transparency and heat stability such as Tg of the (co)polymer to be obtained, a 1-adamantyl group and a 2-norbornyl group are more preferable as $R^{15}$.

Examples of $R^{16}$ in the above formula (11) may include a hydrogen atom, a methyl group, an ethyl group, a propyl group, an isopropyl group, a butyl group and a tert-butyl group. Moreover, examples of $R^{16}$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Of these, a methyl group and an ethyl group are preferable as $R^6$, in terms of having excellent coatability when the polymer is used for a resist composition.

Further, $R^{15}$ and $R^{16}$ in the above formula (11) may form a bridged cyclic hydrocarbon structure containing 4 to 16 carbon atoms, together with the carbon atom to which they are bound. Examples of such a bridged cyclic hydrocarbon structure may include an adamantylidene group and a norbornylidene group. Furthermore, examples of such a bridged cyclic hydrocarbon structure may also include those wherein the bridged cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above structure has two or more substituents, the substituents may be of either a single type, or two or more types.

As stated above, in the above compounds, an alkyl group and/or a bridged cyclic hydrocarbon group may be substituted with a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, a carboxy group esterified with an alcohol containing 1 to 6 carbon atoms, or the like. The number of substituents may be either one, or two or more. When the above compound has two or more substituents, the substituents may be of either a single type, or two or more types.

Of these, a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms are preferable as a substituent, in terms of having excellent light transparency when the polymer is used for a resist composition. Moreover, in terms of having excellent dry etching resistance when the polymer is used for a resist composition, a methyl group and an ethyl group are more preferable as a substituent. And, in terms of having excellent adhesion of the polymer to a substrate when the polymer is used for a resist composition, a hydroxyl group, a hydroxymethyl group, and a hydroxyethyl group are more preferable as a substituent.

The third polymer of the present invention comprising at least one of constitutional units represented by the above formula (11) is obtained by (co)polymerizing a monomer composition comprising a monomer represented by the following formula (I):

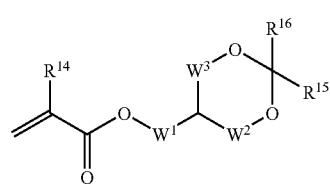
(I)

$W^1$, $W^2$, $W^3$, $R^{14}$, $R^{15}$ and $R^{16}$ in the formula (1) correspond to $W^1$, $W^2$, $W^3$, $R^{14}$, $R^{15}$ and $R^{16}$ in the formula (11), respectively.

Examples of the monomer represented by the above formula (1) may include monomers represented by the formulas (I-1) to (I-45) indicated below. In the formulas (I-1) to (I-45), $R^{14}$ is the same as in the above formula (11), and it represents a hydrogen atom or a methyl group.

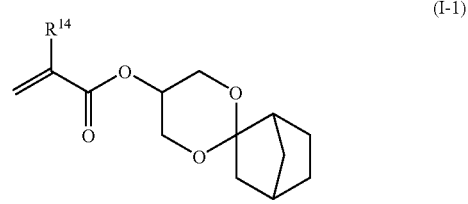
(I-1)

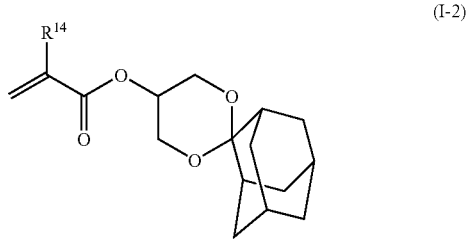
(I-2)

(I-3)

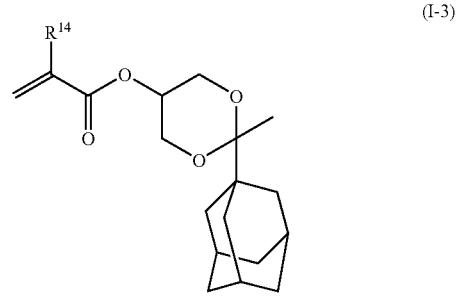
(I-4)

(I-5)

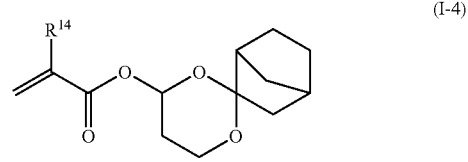
(I-6)

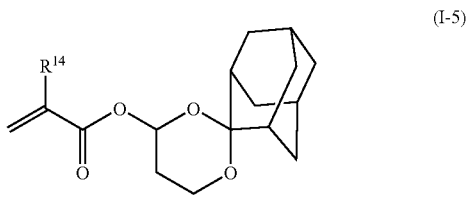
(I-7)

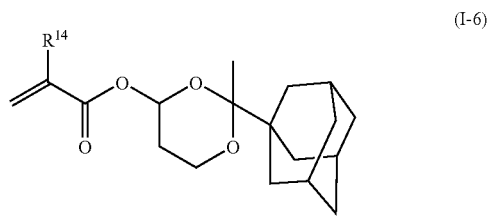

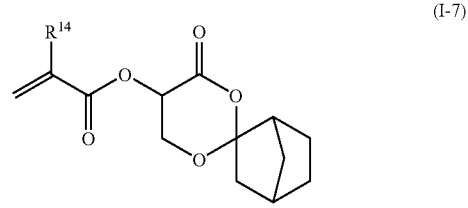

-continued
(I-8)
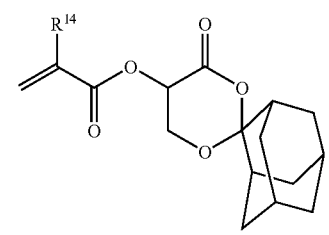
(I-9)
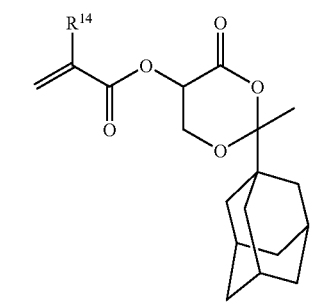
(I-10)
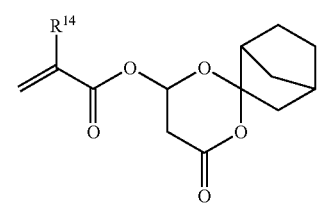
(I-11)
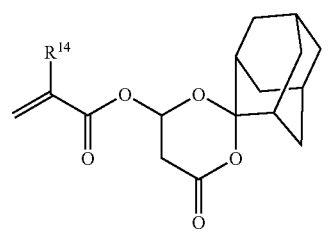
(I-12)
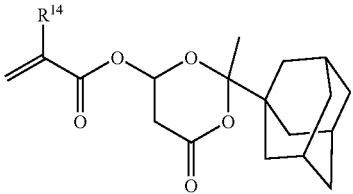
(I-13)
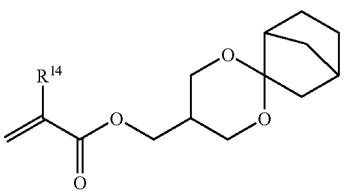
(I-14)
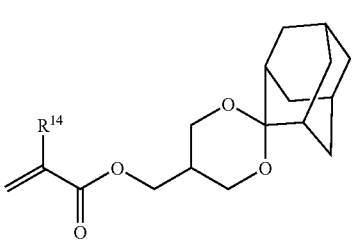
-continued
(I-15)
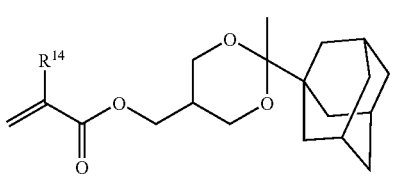
(I-16)
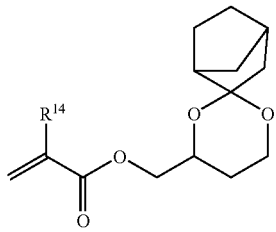
(I-17)
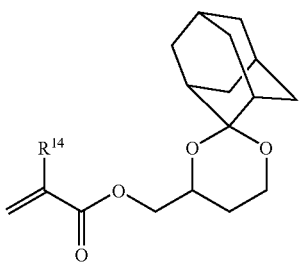
(I-18)
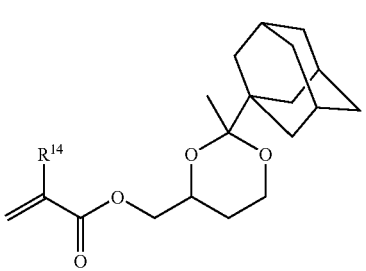
(I-19)
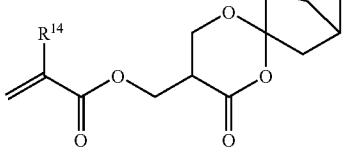
(I-20)
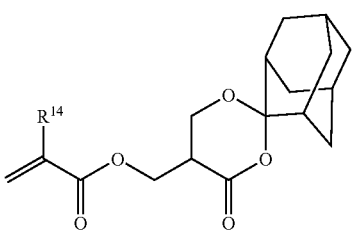
(I-21)
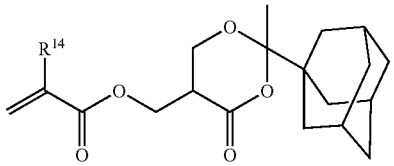

(I-22)
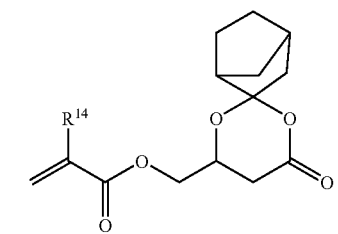
(I-23)
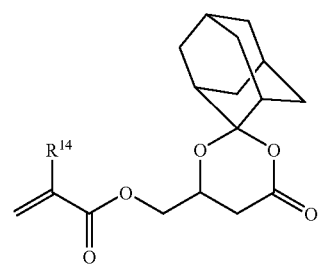
(I-24)
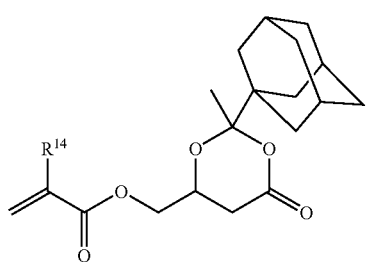
(I-25)
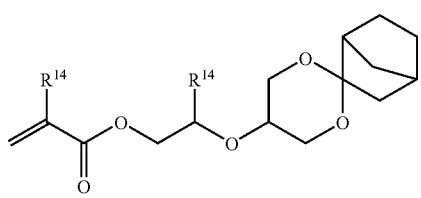
(I-26)
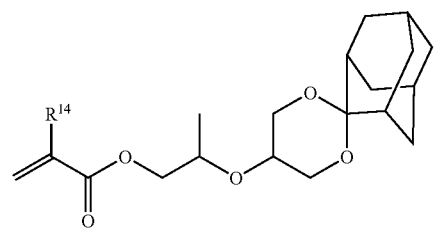
(I-27)
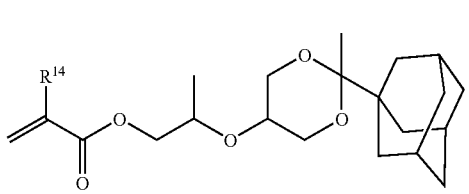
(I-28)
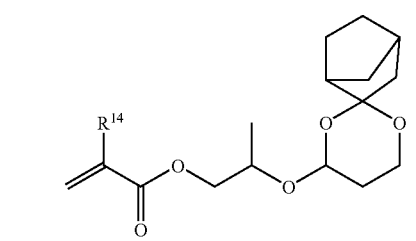
(I-29)
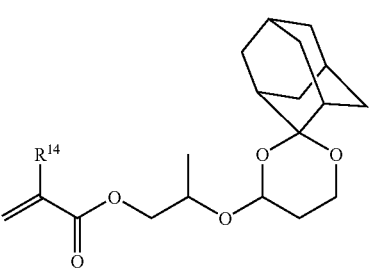
(I-30)
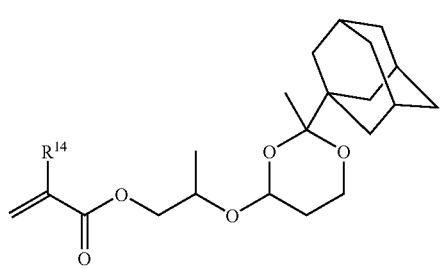
(I-31)
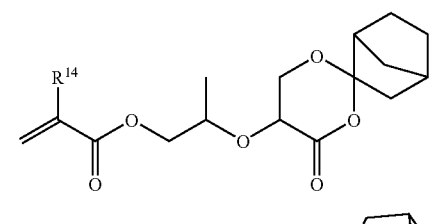
(I-32)
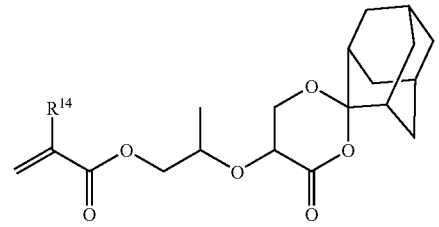
(I-33)
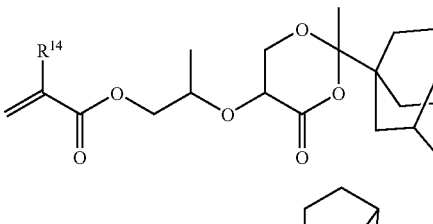
(I-34)
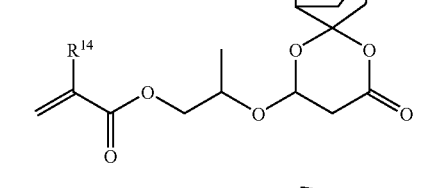
(I-35)
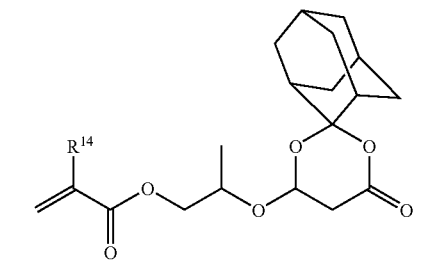

-continued
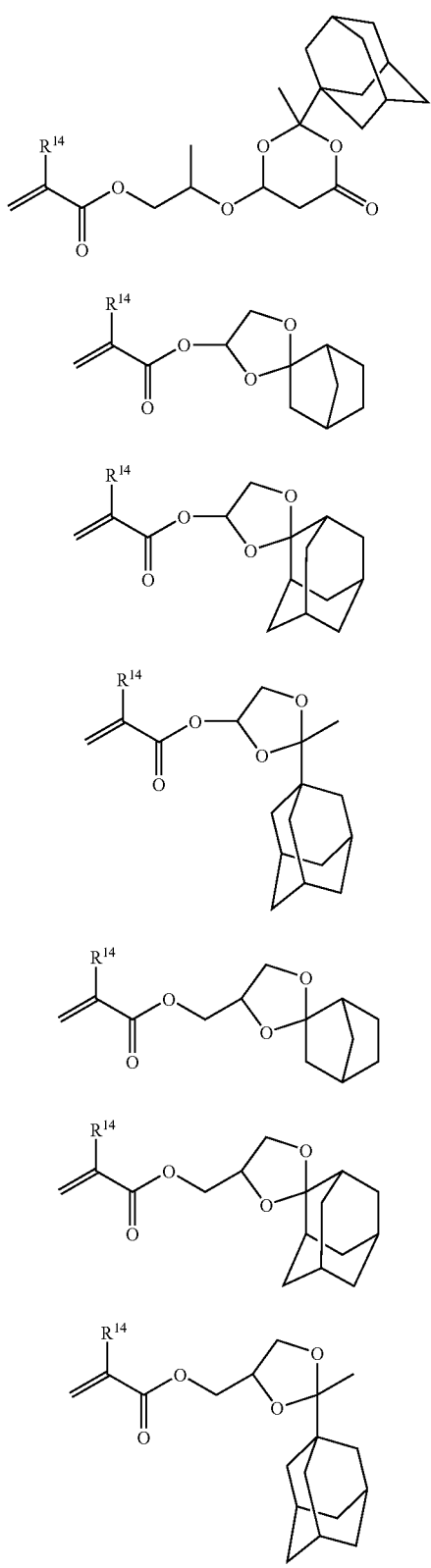
(I-36)
(I-37)
(I-38)
(I-39)
(I-40)
(I-41)
(I-42)
-continued
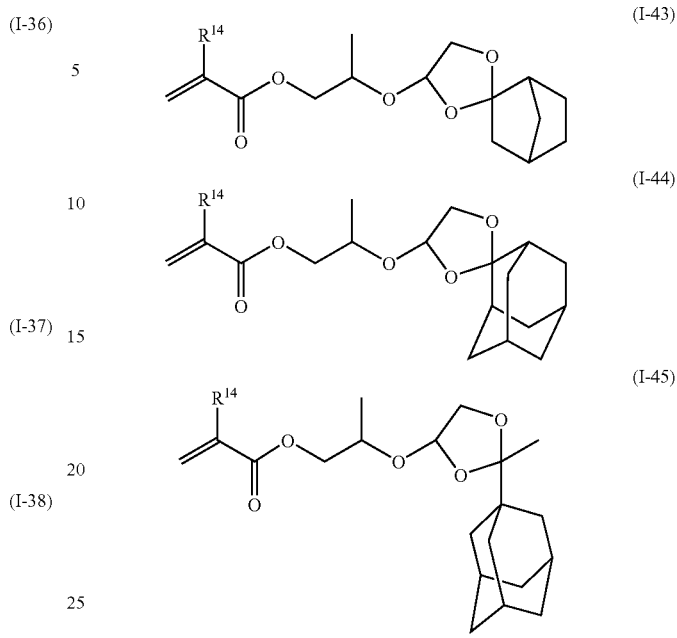
(I-43)
(I-44)
(I-45)
Among the monomers represented by the above formula (1), those represented by the above formulas (I-37) to (I-45) are preferable in terms of storage stability of the polymer.
The monomer represented by the above formula (I) can be produced, for example, by following the process (Scheme 1) indicated below.
(Scheme 1)
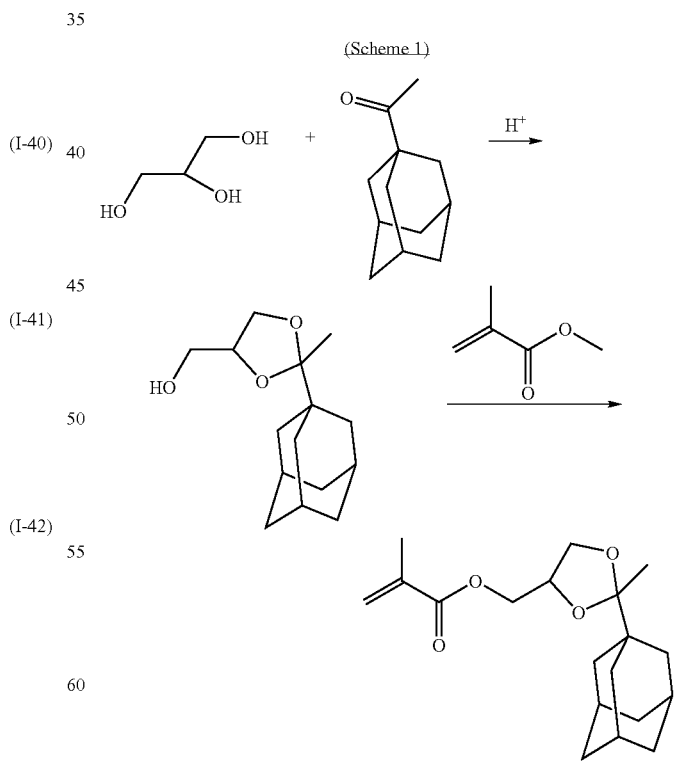

A raw material ketone such as 2-adamantanone, 1-adamantyl methyl ketone, norcampher and derivatives thereof are commercially available, or they can be synthesized by a known production method, and all of them can be used.

A method of synthesizing a cyclic acetal from a ketone and a diol or a hydroxycarboxylic acid under acid conditions is widely known. A low polar solvent such as toluene, cyclohexane or hexane is preferably used as a reaction solvent. Moreover, in advance of the reaction, water contained in the reaction system is preferably removed so as to increase yield.

The esterification reaction of the alcohol can be carried out under common esterification conditions. Examples of a reactant may include a (meth)acrylic halide, a (meth)acrylic anhydride, a (meth)acrylic ester and (meth)acrylic acid. Moreover, a catalyst used in esterification, such as an acid, a base, a Lewis acid or an enzyme, may be used.

In some cases, the product of this reaction may comprise several constitutional isomers, geometric isomers or optical isomers. In the present invention, both a mixture consisting of such isomers and a product containing an intermediate can be used. If necessary, the obtained reaction product may be purified by a known method such as distillation, short-path distillation, recrystallization or column chromatography.

The third polymer of the present invention may be a homopolymer consisting of one type of the monomer represented by the above formula (I), a copolymer consisting of two or more types of the monomer represented by the above formula (I), or a copolymer consisting of at least one type of the monomer represented by the above formula (I) and at least one type of monomers other than the monomer represented by the above formula (I). When the third polymer of the present invention is a copolymer, each constitutional unit can have any given sequence. Accordingly, this polymer may be a random copolymer, an alternating copolymer, or a block copolymer.

In the present invention, at least one type of the monomer represented by the above formula (I) may be copolymerized with at least one type of known monomers other than the above monomer. Examples of a monomer capable of being copolymerized may include those that are conventionally known as a positive resist, a negative resist, an anti-reflection coat material or an insulating film-forming material. For example, the monomer capable of being copolymerized may include a known monomer such as an acrylic acid derivative and a methacrylic acid derivative, which have a dry etching resistance-improving group or a soluble group involving acid dissociation, a carboxylic acid (including a derivative thereof) having an ethylene double bond causing alkali solubility, and known monomers used in the production of an acrylic resin. Specific examples of a monomer capable of being copolymerized may be the same as those described in the first polymer of the present invention.

The third polymer of the present invention is preferably used as a material for a resist composition, and particularly as a material for a chemically amplified resist composition. Hereinafter, a case where the third polymer of the present invention is a resin used for a chemically amplified resist composition will be explained.

As described in the first polymer of the present invention, the resin for a chemically amplified resist composition is required to have both a property for becoming soluble in an alkaline aqueous solution by an acid so as to realize high sensitivity and a structure having high carbon density so as to realize high dry etching resistance. The third polymer of the present invention is excellent in solubility in an organic solvent and heat resistance, and has little line edge roughness. When a structure having a property for becoming soluble in an alkaline aqueous solution by the action of an acid, or a structure having high dry etching resistance is introduced into such a polymer, an excellent resin for a chemically amplified resist composition can be obtained.

Examples of the structure having a functional group that is easily eliminated by the action of an acid and the structure having high carbon density may be the same as those described in the first polymer of the present invention.

In order to introduce the structure having a functional group that is easily eliminated by the action of an acid or the structure having high carbon density into the polymer, the monomer of the present invention may be copolymerized with a monomer having such a structure.

As a monomer having such a structure, for example, the one that is known as a raw material monomer for a resin for a chemically amplified resist composition can be used. A raw material monomer used for the polymer of the present invention is arbitrarily selected depending on light source used in lithography.

For example, when a KrF excimer laser or an electron beam is used as a light source, considering its high etching resistance, a polymer obtained by copolymerizing the monomer of the present invention with p-hydroxystyrene or a derivative thereof is preferably used. In this case, the proportion of the constitutional unit derived from the monomer of the present invention in the polymer is preferably 5% or more and is preferably 60% or less.

When an ArF excimer laser is used as a light source, a polymer obtained by copolymerizing the monomer of the present invention with a monomer having a cyclic hydrocarbon group is preferably used. Copolymerization with a monomer having a cyclic hydrocarbon group enables high etching resistance.

Among them, a polymer obtained by copolymerizing the monomer of the present invention, a monomer having a cyclic hydrocarbon group, a monomer having a hydrophilic functional group and/or a monomer having a lactone structure is preferable.

As described in the first polymer of the present invention, it is known that an acrylic copolymer obtained by copolymerizing a monomer having a cyclic hydrocarbon group and a monomer having a hydrophilic functional group, or an acrylic copolymer obtained by copolymerizing a monomer having a cyclic hydrocarbon group and a monomer having a lactone structure, is preferable as a resin for the ArF excimer laser lithography. Introduction of the monomer unit of the present invention into these polymers enables improvement of solubility in an organic solvent and heat resistance without impairing the resist performance such as high sensitivity, high resolution or high dry etching resistance, thereby providing an excellent resist pattern with only a little line edge roughness.

A monomer unit having a cyclic hydrocarbon group imparts high dry etching resistance to a polymer comprising the same. In particular, a monomer unit having a protecting group that is eliminated by an acid (a cyclic hydrocarbon group may also be a protecting group by itself) imparts also high sensitivity to the polymer comprising the same in photolithography using an ArF excimer laser with a wavelength of 193 nm. The monomer units having a cyclic hydrocarbon group may be of either a single type, or two or more types, if necessary.

Examples of the monomer unit having a cyclic hydrocarbon group may be the same as those described in the first polymer of the present invention, preferred examples being also the same.

A monomer unit having a hydrophilic functional group imparts adhesion to a substrate to a polymer comprising the same. In particular, a monomer unit having a protecting group that is eliminated by an acid imparts also high sensitivity to the polymer comprising the same in photolithography using an ArF excimer laser with a wavelength of 193 nm. Examples of a hydrophilic functional group may include a terminal hydroxy group, an alkyl-substituted ether group, δ-valerolactonyl group, and a γ-butyrolactonyl group. It should be noted that some of the above listed hydrophilic functional groups are generally included in hydrophobic groups. However, since even such functional groups have hydrophilicity that is needed in the present invention, they are herein defined as a hydrophilic functional group. The monomer units having a hydrophilic functional group may be of either a single type, or two or more types, if necessary.

Examples of the monomer unit having a hydrophilic functional group may be the same as those described in the first polymer of the present invention, preferred examples being also the same.

A monomer unit having a lactone structure imparts high dry etching resistance and adhesion to a substrate to a polymer comprising the same.

The monomer units having a lactone structure may be of either a single type, or two or more types, if necessary.

Examples of the monomer unit having a lactone structure may be the same as those described in the first polymer of the present invention, preferred examples being also the same.

Among them, as a resin for a chemically amplified resist composition, a polymer comprising at least one of constitutional units represented by the formula (11) and at least one of constitutional units represented by the formula (8), (9) or (10) is preferable. Such a polymer comprising at least one of constitutional units represented by the formula (11) and at least one of constitutional units represented by the formula (8), (9) or (10) will be described in the section III. The fifth polymer of the present invention.

The mass-average molecular weight of the third polymer of the present invention is not particularly limited. However, when the polymer is used as a resin for a resist composition, the mass-average molecular weight of the third polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

II. The fourth Polymer of the Present Invention

The fourth polymer of the present invention comprises at least one of constitutional units represented by the formula (12) indicated below. The proportion of the constitutional unit represented by the following formula (12) in the polymer is preferably 5 mol % or more.

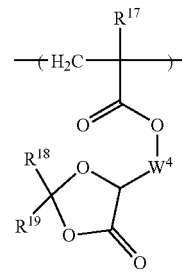

(12)

In formula (12), $W^4$ represents a direct bond or a methylene chain containing 1 to 6 carbon atoms [—$(CH_2)_n$— (wherein n represents an integer of 0 to 6)], $R^{17}$ represents a hydrogen atom or a methyl group, each of $R^{18}$ and $R^{19}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{18}$ and $R^{19}$ represent a cyclic hydrocarbon group containing 4 to 16 carbon atoms together with the carbon atom to which they are bound. $R^{18}$ and $R^{19}$ may be identical or may be different.

Herein, the methylene chain containing 1 to 6 carbon atoms may have, as a substituent, an alkyl group containing 1 to 3 carbon atoms which may be optionally substituted, and may optionally have at least one ether bond therein. Further, the alkyl group and the cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the cyclic hydrocarbon group have two or more substituents, the substituents may be of either a single type, or two or more types.

Examples of a substituent on the linear or branched alkyl group containing 1 to 6 carbon atoms that is the substituent on the alkyl group and the cyclic hydrocarbon group may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

Examples of $W^4$ in the above formula (12) may include a direct bond (which means that the oxygen atom and the carbon atom that are adjacent to $W^4$ are directly bound to each other), $CH_2$, $CH_2CH_2$, $CH_2CH_2CH_2$, $CH(CH_3)CH_2$, $CH_2O$, $CH_2CH_2O$, $CH_2CH(CH_3)O$, $CH(CH_3)CH_2O$, $CH_2CH_2OCH_2CH_2O$, $CH_2CH(CH_3)OCH_2CH(CH_3)O$, and $CH(CH_3)CH_2OCH(CH_3)CH_2O$.

Of these, in terms of storage stability of the polymer, a direct bond, $CH_2$, $CH_2CH_2O$ and $CH_2CH(CH_3)O$ are preferable as $W^4$.

Examples of $R^{18}$ and $R^{19}$ in the above formula (12) may include a hydrogen atom, a methyl group, an ethyl group, a propyl group, an isopropyl group, a butyl group, a tert-butyl group, a cyclopentyl group, a cyclohexyl group, a cycloheptyl group, a 2-norbornyl group, a 1-adamantyl group, a 1-adamantanemethyl group, a 1-adamantaneethyl group, a 2-adamantyl group, a 2-adamantanemethyl group, a 2-adamantaneethyl group and a 2-adamantanonyl group. Moreover, examples of $R^{18}$ and $R^{19}$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Further, $R^{18}$ and $R^{19}$ in the above formula (12) may form a cyclic hydrocarbon structure containing 4 to 16 carbon atoms, together with the carbon atom to which they are bound. Examples of such a cyclic hydrocarbon structure may include an adamantylidene group and a norbornylidene group. Furthermore, examples of such a cyclic hydrocarbon structure may also include those wherein the cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above structure has two or more substituents, the substituents may be of either a single type, or two or more types.

In terms of having excellent dry etching resistance when the polymer is used for a resist composition, as the constitutional unit represented by the above formula (12), a constitutional unit wherein $R^{18}$ represents a bridged cyclic hydrocarbon group containing 4 to 16 carbon atoms, such as a 2-norbornyl group, a 1-adamantyl group, a 1-adamantanemethyl group, a 1-adamantaneethyl group, a 2-adamantyl group, a 2-adamantanemethyl group, a 2-adamantaneethyl group or a 2-adamantanonyl group, or a linear or branched alkyl group containing 1 to 6 carbon atoms having as a substituent the bridged cyclic hydrocarbon group containing 4 to 16 carbon atoms, and $R^{19}$ represents a hydrogen atom, or a linear or branched alkyl group containing 1 to 6 carbon atoms, is preferable. In particular, a constitutional unit wherein $R^{18}$ represents a 2-norbornyl group or a 1-adamantyl group, and $R^{19}$ represents a methyl group or an ethyl group, is more preferable. Moreover, a constitutional unit wherein $R^{18}$ and $R^{19}$ form an adamantylidene group or a norbornylidene group together with the carbon atom to which they are bound, is also preferable.

Furthermore, as stated above, in the above compounds, an alkyl group and/or a cyclic hydrocarbon group may be substituted with a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, a carboxy group esterified with an alcohol containing 1 to 6 carbon atoms, or the like. The number of substituents may be either one, or two or more. When the above compound has two or more substituents, the substituents may be of either a single type, or two or more types.

Of these, a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms are preferable as a substituent, in terms of having excellent light transparency when the polymer is used for a resist composition. Moreover, in terms of having excellent dry etching resistance when the polymer is used for a resist composition, a methyl group and an ethyl group are more preferable as a substituent. And, in terms of having excellent adhesion of the polymer to a substrate when the polymer is used for a resist composition, a hydroxyl group, a hydroxymethyl group, and a hydroxyethyl group are more preferable as a substituent.

The fourth polymer of the present invention comprising at least one of constitutional units represented by the above formula (12) is obtained by (co)polymerizing a monomer composition comprising a monomer represented by the following formula (II):

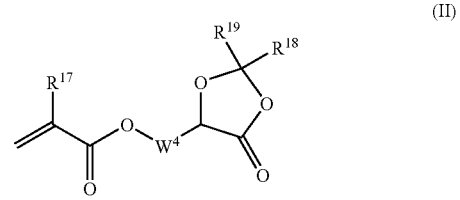

$W^4$, $R^{17}$, $R^{18}$ and $R^{19}$ in the formula (II) correspond to $W^4$, $R^{17}$, $R^{18}$ and $R^{19}$ in the formula (12), respectively.

Examples of the monomer represented by the above formula (11) may include monomers represented by the formulas (II-1) to (III-18) indicated below. In the formulas (II-1) to (II-18), $R^{17}$ is the same as in the above formula (II), and it represents a hydrogen atom or a methyl group.

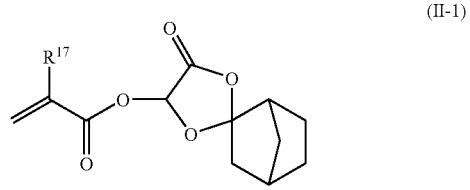

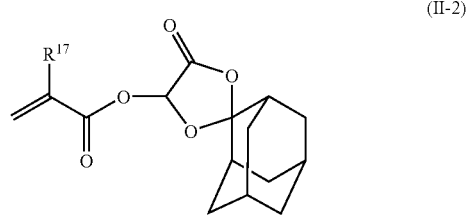

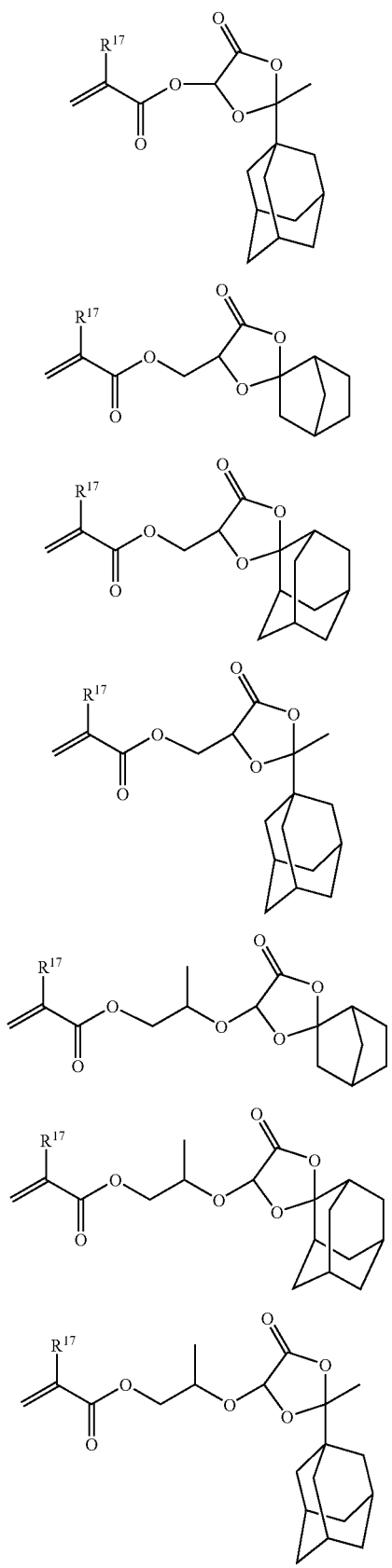
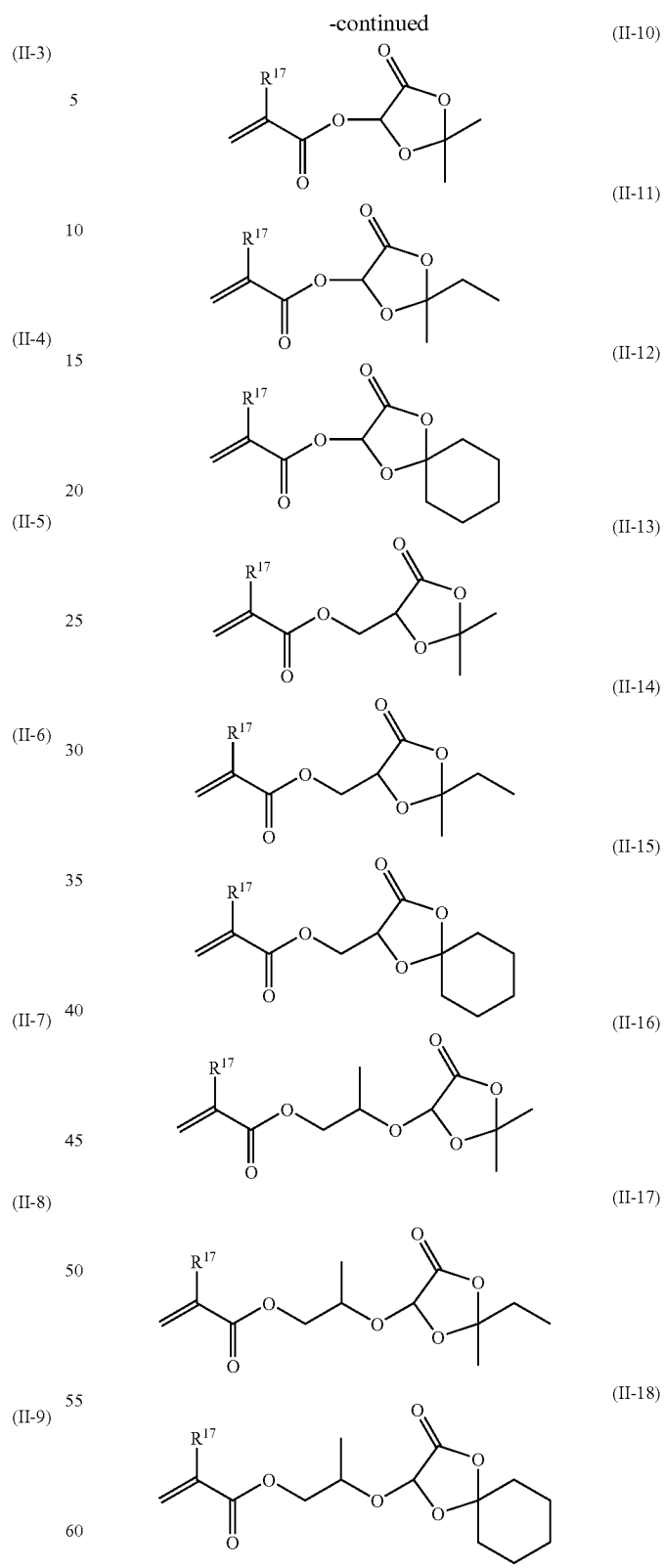
Among the monomers represented by the above formula (II), those represented by the above formulas (II-1) to (II-9) are preferable in terms of having excellent dry etching resistance when the polymer is used for a resist composition.

The monomer represented by the above formula (II) can be produced, for example, by following the process (Scheme 2) indicated below.

(Scheme 2)

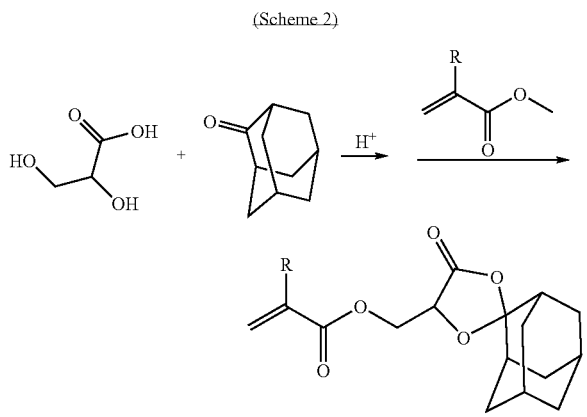

A raw material ketone such as 2-adamantanone, 1-adamantyl methyl ketone, norcamphor and derivatives thereof are commercially available, or they can be synthesized by a known production method, and all of them can be used.

A method of synthesizing a cyclic acetal from a ketone and a diol or a hydroxycarboxylic acid under acid conditions is widely known. A low polar solvent such as toluene, cyclohexane or hexane is preferably used as a reaction solvent. Moreover, in advance of the reaction, water contained in the reaction system is preferably removed so as to increase yield.

The esterification reaction of the alcohol can be carried out under common esterification conditions. Examples of a reactant may include a (meth)acrylic halide, a (meth)acrylic anhydride, a (meth)acrylic ester and (meth)acrylic acid. Moreover, a catalyst used in esterification, such as an acid, a base, a Lewis acid or an enzyme, may be used.

In some cases, the product of this reaction may comprise several constitutional isomers, geometric isomers or optical isomers. In the present invention, both a mixture consisting of such isomers and a product containing an intermediate can be used. If necessary, the obtained reaction product may be purified by a known method such as distillation, short-path distillation, recrystallization or column chromatography.

The fourth polymer of the present invention may be a homopolymer consisting of one type of the monomer represented by the above formula (II), a copolymer consisting of two or more types of the monomer represented by the above formula (II), or a copolymer consisting of at least one type of the monomer represented by the above formula (II) and at least one type of monomers other than the monomer represented by the above formula (II). When the fourth polymer of the present invention is a copolymer, each constitutional unit can have any given sequence. Accordingly, this polymer may be a random copolymer, an alternating copolymer, or a block copolymer.

In the present invention, at least one type of the monomer represented by the above formula (II) may be copolymerized with at least one type of known monomers other than the above monomer. Examples of a monomer capable of being copolymerized may include those that are conventionally known as a positive resist, a negative resist, an anti-reflection coat material or an insulating film-forming material. For example, the monomer capable of being copolymerized may include a known monomer such as an acrylic acid derivative and a methacrylic acid derivative, which have a dry etching resistance-improving group or a soluble group involving acid dissociation, a carboxylic acid (including a derivative thereof) having an ethylene double bond causing alkali solubility, and known monomers used in the production of an acrylic resin. Specific examples of a monomer capable of being copolymerized may be the same as those described in the first polymer of the present invention.

The fourth polymer of the present invention is preferably used as a material for a resist composition, and particularly as a material for a chemically amplified resist composition. Hereinafter, a case where the fourth polymer of the present invention is a resin used for a chemically amplified resist composition will be explained.

As described in the first polymer of the present invention, the resin for a chemically amplified resist composition is required to have both a property for becoming soluble in an alkaline aqueous solution by an acid so as to realize high sensitivity and a structure having high carbon density so as to realize high dry etching resistance. The fourth polymer of the present invention is excellent in solubility in an organic solvent and heat resistance, and has little line edge roughness. When a structure having a property for becoming soluble in an alkaline aqueous solution by the action of an acid, or a structure having high dry etching resistance is introduced into such a polymer, an excellent resin for a chemically amplified resist composition can be obtained.

Examples of the structure having a functional group that is easily eliminated by the action of an acid and the structure having high carbon density may be the same as those described in the first polymer of the present invention.

In order to introduce the structure having a functional group that is easily eliminated by the action of an acid or the structure having high carbon density into the polymer, the monomer of the present invention may be copolymerized with a monomer having such a structure.

As a monomer having such a structure, for example, the one that is known as a raw material monomer for a resin for a chemically amplified resist composition can be used. A raw material monomer used for the polymer of the present invention is arbitrarily selected depending on light source used in lithography.

For example, when a KrF excimer laser or an electron beam is used as a light source, considering its high etching resistance, a polymer obtained by copolymerizing the monomer of the present invention with p-hydroxystyrene or a derivative thereof is preferably used. In this case, the proportion of the constitutional unit derived from the monomer of the present invention in the polymer is preferably 5% or more and is preferably 60% or less.

When an ArF excimer laser is used as a light source, a polymer obtained by copolymerizing the monomer of the present invention with a monomer having a cyclic hydrocarbon group is preferably used. Copolymerization with a monomer having a cyclic hydrocarbon group enables high etching resistance.

Among them, a polymer obtained by copolymerizing the monomer of the present invention, a monomer having a cyclic hydrocarbon group, a monomer having a hydrophilic functional group and/or a monomer having a lactone structure is preferable.

As described in the first polymer of the present invention, it is known that an acrylic copolymer obtained by copolymerizing a monomer having a cyclic hydrocarbon group and a monomer having a hydrophilic functional group, or an acrylic copolymer obtained by copolymerizing a monomer having a cyclic hydrocarbon group and a monomer having a lactone structure, is preferable as a resin for the ArF excimer laser lithography. Introduction of the monomer unit of the present invention into these polymers enables improvement of solubility in an organic solvent and heat resistance without impairing the resist performance such as high sensitivity, high resolution or high dry etching resistance, thereby providing an excellent resist pattern with only a little line edge roughness.

A monomer unit having a cyclic hydrocarbon group imparts high dry etching resistance to a polymer comprising the same. In particular, a monomer unit having a protecting group that is eliminated by an acid (a cyclic hydrocarbon group may also be a protecting group by itself) imparts also high sensitivity to the polymer comprising the same in photolithography using an ArF excimer laser with a wavelength of 193 nm. The monomer units having a cyclic hydrocarbon group may be of either a single type, or two or more types, if necessary.

Examples of the monomer unit having a cyclic hydrocarbon group may be the same as those described in the first polymer of the present invention, preferred examples being also the same.

A monomer unit having a hydrophilic functional group imparts adhesion to a substrate to a polymer comprising the same. In particular, a monomer unit having a protecting group that is eliminated by an acid imparts also high sensitivity to the polymer comprising the same in photolithography using an ArF excimer laser with a wavelength of 193 nm. Examples of a hydrophilic functional group may include a terminal hydroxy group, an alkyl-substituted ether group, a δ-valerolactonyl group, and a γ-butyrolactonyl group. It should be noted that some of the above listed hydrophilic functional groups are generally included in hydrophobic groups. However, since even such functional groups have hydrophilicity that is needed in the present invention, they are herein defined as a hydrophilic functional group. The monomer units having a hydrophilic functional group may be of either a single type, or two or more types, if necessary.

Examples of the monomer unit having a hydrophilic functional group may be the same as those described in the first polymer of the present invention, preferred examples being also the same.

A monomer unit having a lactone structure imparts high dry etching resistance and adhesion to a substrate to a polymer comprising the same. The monomer units having a lactone structure may be of either a single type, or two or more types, if necessary.

Examples of the monomer unit having a lactone structure may be the same as those described in the first polymer of the present invention, preferred examples being also the same.

Among them, as a resin for a chemically amplified resist composition, a polymer comprising at least one of constitutional units represented by the formula (12) and at least one of constitutional units represented by the formula (8), (9) or (10) is preferable. Such a polymer comprising at least one of constitutional units represented by the formula (12) and at least one of constitutional units represented by the formula (8), (9) or (10) will be described in the section III. The fifth polymer of the present invention.

The mass-average molecular weight of the fourth polymer of the present invention is not particularly limited. However, when the polymer is used as a resin for a resist composition, the mass-average molecular weight of the fourth polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

III. The Fifth Polymer of the Present Invention

The fifth polymer of the present invention comprises at least one of constitutional units represented by the following formula (13) and at least one of constitutional units represented by the following formula (8), (9) or (10):

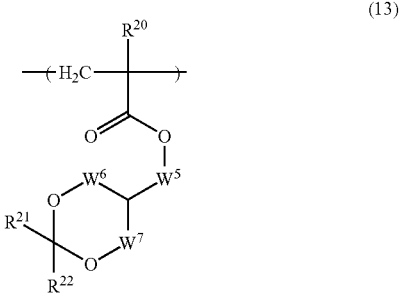

In formula (13), $W^5$ represents a direct bond or a methylene chain containing 1 to 6 carbon atoms [—$(CH_2)_x$— (wherein x represents an integer of 0 to 6)], $W^6$ represents a direct bond or a methylene chain containing 1 to 3 carbon atoms [—$(CH_2)_y$— (wherein y represents an integer of 0 to 3)], $W^7$ represents a methylene chain containing 1 to 3 carbon atoms [—$(CH_2)_z$— (wherein z represents an integer of 1 to 3)], $R^{20}$ represents a hydrogen atom or a methyl group, each of $R^{21}$ and $R^{22}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{21}$ and $R^{22}$ represent a cyclic hydrocarbon group containing 4 to 16 carbon atoms together with the carbon atom to which they are bound. $R^{21}$ and $R^{22}$ may be identical or may be different.

Herein, the methylene chain containing 1 to 6 carbon atoms may have, as a substituent, an alkyl group containing 1 to 3 carbon atoms which may be optionally substituted, and may optionally have at least one ether bond therein. The methylene chain containing 1 to 3 carbon atoms may have a carbonyl group therein. Further, the alkyl group and the cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the cyclic hydrocarbon group have two or more substituents, the substituents may be of either a single type, or two or more types.

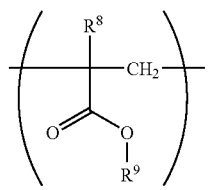
(8)

In formula (8), $R^8$ represents a hydrogen atom or a methyl group, and $R^9$ represents a linear or branched alkyl group containing 1 to 6 carbon atoms, a cyclic hydrocarbon group containing 4 to 8 carbon atoms, or a bridged cyclic hydrocarbon group containing 4 to 16 carbon atoms.

Herein, the alkyl group, the cyclic hydrocarbon group and the bridged cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms. When the alkyl group, the cyclic hydrocarbon group and the bridged cyclic hydrocarbon group have two or more substituents, the substituents may be of either a single type, or two or more types.

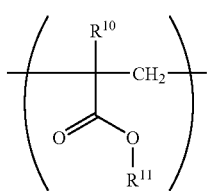
(9)

In formula (9), $R^{10}$ represents a hydrogen atom or a methyl group, and $R^{11}$ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group.

Herein, the alkyl group, the cyclic hydrocarbon group, the bridged cyclic hydrocarbon group and the hydrophilic functional group may be unsubstituted, or may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms. When the alkyl group, the cyclic hydrocarbon group, the bridged cyclic hydrocarbon group and the hydrophilic functional group have two or more substituents, the substituents may be of either a single type, or two or more types.

Examples of a hydrophilic functional group in the formula (9) may include groups with high polarity, such as a hydroxyl group, a carboxy group or an amino group; linear or branched alkyl groups having a structure such as ketone, acid anhydride, ester, ether, lactone, imide or amide; and cyclic compounds. Compounds having a hydrophilic functional group may include monocyclic saturated hydrocarbon groups containing 4 to 8 carbon atoms or a bridged cyclic hydrocarbon groups containing 4 to 16 carbon atoms, a portion of the skeleton of which is substituted with a structure such as ketone, acid anhydride, ester, ether, lactone, imide or amide. Some of the above listed hydrophilic functional groups are generally included in hydrophobic groups. However, since even such functional groups have hydrophilicity that is needed for a resist composition of the present invention, they are herein defined as a hydrophilic functional group.

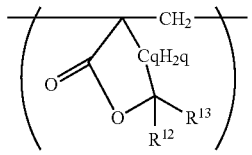
(10)

In formula (10), each of $R^{12}$ and $R^{13}$ independently represents a hydrogen atom, a methyl group or an ethyl group, and q represents an integer of 1 to 4. $R^{12}$ and $R^{13}$ may be identical or may be different.

Herein, $C_qH_{2q}$ represents a methylene chain containing 1 to 4 carbon atoms [—$(CH_2)_q$— (wherein q represents an integer of 1 to 4)].

In the fifth polymer of the present invention, the constitutional units (13), (8), (9) and (10) are not necessarily of the same type, but two or more types may be mixed therein as long as they are represented by the above general formulas. Moreover, in this polymer, each constitutional unit can have any given sequence. Accordingly, this polymer may be a random copolymer, an alternating copolymer, or a block copolymer.

Examples of a substituent on the linear or branched alkyl group containing 1 to 6 carbon atoms that is the substituent on the alkyl group, the cyclic hydrocarbon group, the bridged cyclic hydrocarbon group and the hydrophilic functional group, may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

Examples of $W^5$ in the above formula (13) may include a direct bond (which means that the oxygen atom and the carbon atom that are adjacent to $W^6$ are directly bound to each other), $CH_2$, $CH_2CH_2$, $CH_2CH_2CH_2$, $CH(CH_3)CH_2$, $CH_2O$, $CH_2CH_2O$, $CH_2CH(CH_3)O$, $CH(CH_3)CH_2O$, $CH_2CH_2OCH_2CH_2O$, $CH_2CH(CH_3)OCH_2CH(CH_3)O$, and $CH(CH_3)CH_2OCH(CH_3)CH_2O$.

Of these, in terms of storage stability of the polymer, a direct bond, $CH_2$, $CH_2CH_2O$ and $CH_2CH(CH_3)O$ are preferable as $W^5$.

Examples of $W^6$ in the above formula (13) may include a direct bond (which means that the oxygen atom and the carbon atom that are adjacent to $W^6$ are directly bound to each other), $CH_2$, $C(O)$, $CH_2CH_2$, $CH_2C(O)$, $CH_2CH_2CH_2$, and $CH_2C(O)CH_2$.

Of these, in terms of storage stability of the polymer, a direct bond, $CH_2$, $C(O)$ and $CH_2C(O)$ are preferable as $W^6$.

Examples of $W^7$ in the above formula (13) may include $CH_2$, $C(O)$, $CH_2CH_2$, $CH_2C(O)$, $CH_2CH_2CH_2$, and $CH_2C(O)CH_2$.

Of these, in terms of storage stability of the polymer, $CH_2$, $C(O)$ and $CH_2C(O)$ are preferable as $W^7$.

Examples of $R^{21}$ and $R^{22}$ in the above formula (13) may include a hydrogen atom, a methyl group, an ethyl group, a propyl group, an isopropyl group, a butyl group, a tert-butyl group, a cyclopentyl group, a cyclohexyl group, a cycloheptyl group, a 2-norbornyl group, a 1-adamantyl group, a 1-adamantanemethyl group, a 1-adamantaneethyl group, a 2-adamantyl group, a 2-adamantanemethyl group, a 2-adamantaneethyl group and a 2-adamantanonyl group. Moreover, examples of $R^{21}$ and $R^{22}$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Further, $R^{21}$ and $R^{22}$ in the above formula (13) may form a cyclic hydrocarbon structure containing 4 to 16 carbon atoms, together with the carbon atom to which they are bound. Examples of such a cyclic hydrocarbon structure may include an adamantylidene group, a norbornylidene group, and a cyclohexylidene group. Furthermore, examples of such a cyclic hydrocarbon structure may also include those wherein the cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above structure has two or more substituents, the substituents may be of either a single type, or two or more types.

As the constitutional unit represented by the above formula (13), a constitutional unit wherein $R^{21}$ represents a hydrogen atom, a methyl group or an ethyl group and $R^{22}$ represents a cyclopentyl group, a cyclohexyl group or a cycloheptyl group, and a constitutional unit wherein $R^{21}$ and $R^{22}$ form a cyclic hydrocarbon group containing 5 to 12 carbon atoms together with the carbon atom to which they are bound, are preferable. Among them, the constitutional unit represented by the above formula (11) and the constitutional unit represented by the above formula (12), are particularly preferable.

The constitutional unit represented by the above formula (8) is obtained by copolymerizing a monomer such as cyclohexyl (meth)acrylate, 1-isobornyl (meth)acrylate, adamantyl (meth)acrylate, tricyclodecanyl (meth)acrylate, dicyclopentyl (meth)acrylate, 2-(meth)acryloyloxy-2-methyladamantane, 2-(meth)acryloyloxy-2-ethyladamantane, or derivatives having a substituent such as an alkyl group, a hydroxy group or a carboxy group on the cyclic hydrocarbon group of these monomers.

In terms of sensitivity and resolution when the polymer is used as a resist composition material, a constitutional unit derived from 2-(meth)acryloyloxy-2-methyladamantane, and a constitutional unit derived from 2-(meth)acryloyloxy-2-ethyladamantane are preferable, as the constitutional unit represented by the above formula (8).

The constitutional unit represented by the above formula (9) is obtained by copolymerizing a monomer having a hydrophilic functional group, such as (meth)acrylate having a terminal hydroxy group, (meth)acrylate having an alkyl-substituted ether group, (meth)acrylate having a δ-valerolactonyl group, or (meth)acrylate having a γ-butyrolactonyl group; derivatives having a substituent such as an alkyl group, a hydroxy group or a carboxy group on the hydrophilic functional group of these monomers; or a monomer having a hydrophilic functional group such as a hydroxy group or a carboxy group on the cyclic hydrocarbon group of a monomer such as cyclohexyl (meth)acrylate, 1-isobornyl (meth)acrylate, adamantyl (meth)acrylate, tricyclodecanyl (meth)acrylate, dicyclopentyl (meth)acrylate, 2-(meth)acryloyloxy-2-methyladamantane or 2-(meth)acryloyloxy-2-ethyladamantane. Specific examples of such a monomer may include 2-hydroxyethyl (meth)acrylate, 2-hydroxypropyl (meth)acrylate, 4-hydroxybutyl (meth)acrylate, 2-methoxyethyl (meth)acrylate, 2-ethoxyethyl (meth)acrylate, 1-methacryloyloxy-3-hydroxyadamantane, β-(meth)acryloyloxy-β-methyl-δ-valerolactone, β-(meth)acryloyloxy-γ-butyrolactone, β-(meth)acryloyloxy-β-methyl-γ-butyrolactone, α-(meth)acryloyloxy-γ-butyrolactone, 2-(1-(meth)acryloyloxy)ethyl-4-butanolide, pantolactone (meth)acrylate, 8-methacryloyloxy-3-oxatricyclo[5.2.1.0$^{2,6}$]decan-2-one, and 9-methacryloyloxy-3-oxatricyclo[5.2.1.0$^{2,6}$]decan-2-one.

In terms of adhesion to a substrate when the polymer is used as a resist composition material, a constitutional unit derived from 1-methacryloyloxy-3-hydroxyadamantane, a constitutional unit derived from 8-methacryloyloxy-3-oxatricyclo[5.2.1.0$^{2,6}$]decan-2-one, and a constitutional unit derived from 9-methacryloyloxy-3-oxatricyclo[5.2.1.0$^{2,6}$]decan-2-one are preferable, as the constitutional unit represented by the above formula (9).

The constitutional unit represented by the above formula (10) is obtained by copolymerizing a monomer such as 4-8 membered α-methylenelactone, or derivatives having a substituent such as an alkyl group, a hydroxy group or a carboxy group on a carbon of the lactone ring of these monomers.

In terms of sensitivity and resolution when the polymer is used as a resist composition material, a constitutional unit derived from α-methylene-γ-butyrolactone, and a constitutional unit derived from its derivatives having a substituent such as a methyl group or an ethyl group on the carbon of the γ position, for example, α-methylene-γ-butyrolactone, α-methylene-γ-methyl-γ-butyrolactone, α-methyleneγ-ethyl-γ-butyrolactone, and 4,4-dimethyl-2-methylene-4-butanolide, are preferable, as the constitutional unit represented by the above formula (10).

In order to improve solubility of the polymer in an organic solvent and heat resistance and to reduce line edge roughness, the proportion of the constitutional unit represented by the above formula (13) is preferably 5 mol % or more in the polymer. Moreover, in order not to reduce sensitivity and resolution, the proportion of the constitutional unit represented by the above formula (13) is preferably 50 mol % or less in the polymer.

In order to improve sensitivity and resolution, the proportion of the constitutional unit represented by the above formula (8) is preferably 30 mol % or more in the polymer. Moreover, in order not to reduce solubility of the polymer in an organic solvent, the proportion of the constitutional unit represented by the above formula (8) is preferably 70 mol % or less in the polymer.

In order not to reduce dry etching resistance, the proportion of the constitutional unit represented by the above formula (9) is preferably 70 mol % or less in the polymer.

In order not to reduce sensitivity and resolution, the proportion of the constitutional unit represented by the above formula (10) is preferably 60 mol % or less in the polymer.

The fifth polymer of the present invention is preferably used as a material for a resist composition, and particularly as a material for a chemically amplified resist composition. The fifth polymer of the present invention is particularly excellent in sensitivity, resolution, and the like.

Moreover, the fifth polymer of the present invention may comprise at least one type of constitutional units derived from known monomers other than the constitutional units represented by the above formulas (13) and (8) to (10). Specific examples of a monomer capable of being copolymerized or a constitutional unit may be the same as those described in the first polymer of the present invention.

The mass-average molecular weight of the fifth polymer of the present invention is not particularly limited. However, when the polymer is used as a resin for a resist composition, the mass-average molecular weight of the fifth polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

6. Other Polymers for a Resist Used for the Resist Composition of the Present Invention As a polymer for a resist used for the resist composition of the present invention, a polymer comprising at least one of constitutional units represented by the above formula (7) other than the second polymer of the present invention (the sixth polymer), or a polymer comprising at least one of constitutional units represented by the above formula (13) other than the fifth polymer of the present invention (the seventh polymer), may also be used. The resist composition of the present invention containing at least one polymer comprising at least one of constitutional units represented by the above formula (7), and the resist composition of the present invention containing at least one polymer comprising at least one of constitutional units represented by the above formula (13), also have sufficient sensitivity, resolution and dry etching resistance, while having little line edge roughness.

I. The Sixth Polymer of the Present Invention

The sixth polymer of the present invention comprises at least one of constitutional units represented by the formula (7) indicated below. The sixth polymer of the present invention may be a homopolymer consisting of one type of the constitutional unit represented by the following formula (7), a copolymer consisting of two or more types of the constitutional unit represented by the following formula (7), or a copolymer consisting of at least one type of the constitutional unit represented by the following formula (7) and at least one type of constitutional unit other than the constitutional unit represented by the following formula (7). When the sixth polymer of the present invention is a copolymer, each constitutional unit can have any given sequence. Accordingly, this polymer may be a random copolymer, an alternating copolymer, or a block copolymer. The proportion of the constitutional unit represented by the following formula (7) in the polymer is preferably 5 mol % or more.

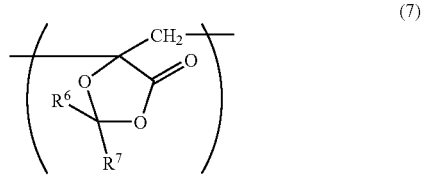

In formula (7), each of $R^6$ and $R^7$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^6$ and $R^7$ represent a cyclic hydrocarbon group containing 4 to 16 carbon atoms together with the carbon atom to which they are bound. $R^6$ and $R^7$ may be identical or may be different.

Herein, the alkyl group and the cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the cyclic hydrocarbon group have two or more substituents, the substituents may be of either a single type, or two or more types.

Examples of a substituent on the linear or branched alkyl group containing 1 to 6 carbon atoms that is the substituent on the alkyl group and the a cyclic hydrocarbon group may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

Examples of $R^6$ and $R^7$ in the above formula (7) may include a hydrogen atom, a methyl group, an ethyl group, a propyl group, an isopropyl group, a butyl group, a tert-butyl group, a cyclopentyl group, a cyclohexyl group, a cycloheptyl group, a 2-norbornyl group, a 1-adamantyl group, a 1-adamantanemethyl group, a 1-adamantaneethyl group, a 2-adamantyl group, a 2-adamantanemethyl group, a 2-adamantaneethyl group and a 2-adamantanonyl group. Moreover, $R^6$ and $R^7$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Moreover, $R^6$ and $R^7$ in the above formula (7) may form a cyclic hydrocarbon structure containing 4 to 16 carbon atoms, together with the carbon atom to which they are bound. Examples of such a cyclic hydrocarbon structure may include an adamantylidene group, a norbornylidene group, and a cyclohexylidene group. Furthermore, examples of such a cyclic hydrocarbon structure may also include those wherein the cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the structure has two or more substituents, the substituents may be of either a single type, or two or more types.

As the constitutional unit represented by the above formula (7), a constitutional unit wherein $R^6$ represents a hydrogen atom, a methyl group or an ethyl group and $R^7$ represents a cyclopentyl group, a cyclohexyl group or a cycloheptyl group, and a constitutional unit wherein $R^6$ and $R^7$ form a cyclic hydrocarbon group containing 5 to 8 carbon atoms together with the carbon atom to which they are bound, are preferable.

The sixth polymer of the present invention may comprise at least one type of constitutional units other than the constitutional unit represented by the above formula (7). Examples of a monomer capable of being copolymerized in the sixth polymer of the present invention may include those that are conventionally known as a positive resist, a negative resist, an anti-reflection coat material or an insulating film-forming material. For example, the monomer capable of being copolymerized may include a known monomer such as an acrylic acid derivative and a methacrylic acid derivative, which have a dry etching resistance-improving group or a soluble group involving acid dissociation, a carboxylic acid (including a derivative thereof) having an ethylene double bond causing alkali solubility, and known monomers used in the production of an acrylic resin. Specific examples of a monomer capable of being copolymerized may be the same as those described in the first polymer of the present invention.

As described in the first polymer of the present invention, the resin for a chemically amplified resist composition is required to have both a property for becoming soluble in an alkaline aqueous solution by an acid so as to realize high sensitivity and a structure having high carbon density so as to realize high dry etching resistance. The sixth polymer of the present invention is excellent in solubility in an organic solvent and heat resistance, and has little line edge roughness. When a structure having a property for becoming soluble in an alkaline aqueous solution by the action of an acid, or a structure having high dry etching resistance is introduced into such a polymer, an excellent resin for a chemically amplified resist composition can be obtained.

Examples of the structure having a functional group that is easily eliminated by the action of an acid and the structure having high carbon density may be the same as those described in the first polymer of the present invention.

In order to introduce the structure having a functional group that is easily eliminated by the action of an acid or the structure having high carbon density into the polymer, the monomer of the present invention may be copolymerized with a monomer having such a structure.

As a monomer having such a structure, for example, the one that is known as a raw material monomer for a resin for a chemically amplified resist composition can be used. A raw material monomer used for the polymer of the present invention is arbitrarily selected depending on light source used in lithography.

For example, when a KrF excimer laser or an electron beam is used as a light source, considering its high etching resistance, a polymer obtained by copolymerizing the monomer of the present invention with p-hydroxystyrene or a derivative thereof is preferably used. In this case, the proportion of the constitutional unit derived from the monomer of the present invention in the polymer is preferably 5% or more and is preferably 60% or less.

When an ArF excimer laser is used as a light source, a polymer obtained by copolymerizing the monomer of the present invention with a monomer having a cyclic hydrocarbon group is preferably used. Copolymerization with a monomer having a cyclic hydrocarbon group enables high etching resistance.

Among them, a polymer obtained by copolymerizing the monomer of the present invention, a monomer having a cyclic hydrocarbon group, a monomer having a hydrophilic functional group and/or a monomer having a lactone structure is preferable.

As described in the first polymer of the present invention, it is known that an acrylic copolymer obtained by copolymerizing a monomer having a cyclic hydrocarbon group and a monomer having a hydrophilic functional group, or an acrylic copolymer obtained by copolymerizing a monomer having a cyclic hydrocarbon group and a monomer having a lactone structure, is preferable as a resin for the ArF excimer laser lithography. Introduction of the monomer unit of the present invention into these polymers enables improvement of solubility in an organic solvent and heat resistance without impairing the resist performance such as high sensitivity, high resolution or high dry etching resistance, thereby providing an excellent resist pattern with only a little line edge roughness.

A monomer unit having a cyclic hydrocarbon group imparts high dry etching resistance to a polymer comprising the same. In particular, a monomer unit having a protecting group that is eliminated by an acid (a cyclic hydrocarbon group may also be a protecting group by itself) imparts also high sensitivity to the polymer comprising the same in photolithography using an ArF excimer laser with a wavelength of 193 nm. The monomer units having a cyclic hydrocarbon group may be of either a single type, or two or more types, if necessary.

Examples of the monomer unit having a cyclic hydrocarbon group may be the same as those described in the first polymer of the present invention, preferred examples being also the same.

A monomer unit having a hydrophilic functional group imparts adhesion to a substrate to a polymer comprising the same. In particular, a monomer unit having a protecting group that is eliminated by an acid imparts also high sensitivity to the polymer comprising the same in photolithography using an ArF excimer laser with a wavelength of 193 nm. Examples of a hydrophilic functional group may include a terminal hydroxy group, an alkyl-substituted ether group, a δ-valerolactonyl group, and a γ-butyrolactonyl group. It should be noted that some of the above listed hydrophilic functional groups are generally included in hydrophobic groups. However, since even such functional groups have hydrophilicity that is needed in the present invention, they are herein defined as a hydrophilic functional group. The monomer units having a hydrophilic functional group may be of either a single type, or two or more types, if necessary.

Examples of the monomer unit having a hydrophilic functional group may be the same as those described in the first polymer of the present invention, preferred examples being also the same.

A monomer unit having a lactone structure imparts high dry etching resistance and adhesion to a substrate to a polymer comprising the same.

The monomer units having a lactone structure may be of either a single type, or two or more types, if necessary.

Examples of the monomer unit having a lactone structure may be the same as those described in the first polymer of the present invention, preferred examples being also the same.

The mass-average molecular weight of the sixth polymer of the present invention is not particularly limited. However, the mass-average molecular weight of the sixth polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

II. The Seventh Polymer of the Present Invention

The seventh polymer of the present invention comprises at least one of constitutional units represented by the formula (13) indicated below. The seventh polymer of the present invention may be a homopolymer consisting of one type of the constitutional unit represented by the following formula (13), a copolymer consisting of two or more types of the constitutional unit represented by the following formula (13), or a copolymer consisting of at least one type of the constitutional unit represented by the following formula (13) and at least one type of constitutional unit other than the constitutional unit represented by the following formula (13). When the seventh polymer of the present invention is a copolymer, each constitutional unit can have any given sequence. Accordingly, this polymer may be a random copolymer, an alternating copolymer, or a block copolymer. The proportion of the constitutional unit represented by the following formula (13) in the polymer is preferably 5 mol % or more.

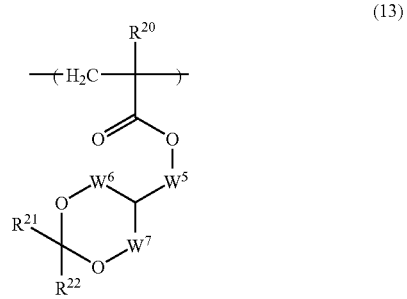

(13)

In formula (13), $W^5$ represents a direct bond or a methylene chain containing 1 to 6 carbon atoms [—$(CH_2)_x$— (wherein x represents an integer of 0 to 6)], $W^6$ represents a direct bond or a methylene chain containing 1 to 3 carbon atoms [—$(CH_2)_y$— (wherein y represents an integer of 0 to 3)], $W^7$ represents a methylene chain containing 1 to 3 carbon atoms [—$(CH_2)_z$— (wherein z represents an integer of 1 to 3)], $R^{20}$ represents a hydrogen atom or a methyl group, each of $R^{21}$ and $R^{22}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{21}$ and $R^{22}$ represent a cyclic hydrocarbon group containing 4 to 16 carbon atoms together with the carbon atom to which they are bound. $R^{21}$ and $R^{22}$ may be identical or may be different.

Herein, the methylene chain containing 1 to 6 carbon atoms may have, as a substituent, an alkyl group containing 1 to 3 carbon atoms which may be optionally substituted, and may optionally have at least one ether bond therein. The methylene chain containing 1 to 3 carbon atoms may have a carbonyl group therein. Further, the alkyl group and the cyclic hydrocarbon group may be unsubstituted, or may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms. When the alkyl group and the cyclic hydrocarbon group have two or more substituents, the substituents may be of either a single type, or two or more types.

Examples of a substituent on the linear or branched alkyl group containing 1 to 6 carbon atoms that is the substituent on the alkyl group and the cyclic hydrocarbon group may include a hydroxy group, a carboxy group, an acyl group containing 1 to 6 carbon atoms, and an amino group. The number of substituents may be either one, or two or more. When the above group has two or more substituents, the substituents may be of either a single type, or two or more types.

Examples of $W^5$ in the above formula (13) may include a direct bond (which means that the oxygen atom and the carbon atom that are adjacent to $W^5$ are directly bound to each other), $CH_2$, $CH_2CH_2$, $CH_2CH_2CH_2$, $CH(CH_3)CH_2$, $CH_2O$, $CH_2CH_2O$, $CH_2CH(CH_3)O$, $CH(CH_3)CH_2O$, —$CH_2CH_2OCH_2CH_2O$, $CH_2CH(CH_3)OCH_2CH(CH_3)O$, and $CH(CH_3)CH_2OCH(CH_3)CH_2O$.

Of these, in terms of storage stability of the polymer, a direct bond, $CH_2$, $CH_2CH_2O$ and $CH_2CH(CH_3)O$ are preferable as $W^5$.

Examples of $W^6$ in the above formula (13) may include a direct bond (which means that the oxygen atom and the carbon atom that are adjacent to $W^6$ are directly bound to each other), $CH_2$, $C(O)$, $CH_2CH_2$, $CH_2C(O)$, $CH_2CH_2CH_2$, and $CH_2C(O)CH_2$.

Of these, in terms of storage stability of the polymer, a direct bond, $CH_2$, $C(O)$ and $CH_2C(O)$ are preferable as $W^6$.

Examples of $W^7$ in the above formula (13) may include $CH_2$, $C(O)$, $CH_2CH_2$, $CH_2C(O)$, $CH_2CH_2CH_2$, and $CH_2C(O)CH_2$.

Of these, in terms of storage stability of the polymer, $CH_2$, $C(O)$ and $CH_2C(O)$ are preferable as $W^7$.

Examples of $R^{21}$ and $R^{22}$ in the above formula (13) may include a hydrogen atom, a methyl group, an ethyl group, a propyl group, an isopropyl group, a butyl group, a tert-butyl group, a cyclopentyl group, a cyclohexyl group, a cycloheptyl group, a 2-norbornyl group, a 1-adamantyl group, a 1-adamantanemethyl group, a 1-adamantaneethyl group, a 2-adamantyl group, a 2-adamantanemethyl group, a 2-adamantaneethyl group and a 2-adamantanonyl group. Moreover, examples of $R^{21}$ and $R^{22}$ may include a structure wherein these groups are substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above group has two or more substituents, the substituents may be of either a single type, or two or more types.

Further, $R^{21}$ and $R^{22}$ in the above formula (13) may form a cyclic hydrocarbon structure containing 4 to 16 carbon atoms, together with the carbon atom to which they are bound. Examples of such a cyclic hydrocarbon structure may include an adamantylidene group, a norbornylidene group, and a cyclohexylidene group. Furthermore, examples of such a cyclic hydrocarbon structure may also include those wherein the cyclic hydrocarbon structure containing 4 to 16 carbon atoms is substituted with at least one substituent selected from a group consisting of a linear or branched alkyl group containing 1 to 6 carbon atoms which may be optionally substituted (e.g., a hydroxy group, a carboxy group, a carboxy group esterified with an alcohol containing 1 to 6 carbon atoms, an acyl group containing 1 to 6 carbon atoms, an amino group, and the like), a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, or the like. The number of substituents may be either one, or two or more. When the above structure has two or more substituents, the substituents may be of either a single type, or two or more types.

As the constitutional unit represented by the above formula (13), a constitutional unit wherein $R^{21}$ represents a hydrogen atom, a methyl group or an ethyl group and $R^{22}$ represents a cyclopentyl group, a cyclohexyl group or a cycloheptyl group, and a constitutional unit wherein $R^{21}$ and $R^{22}$ form a cyclic hydrocarbon group containing 5 to 12 carbon atoms together with the carbon atom to which they are bound, are preferable.

The seventh polymer of the present invention may comprise at least one type of constitutional units other than the constitutional unit represented by the above formula (13). Examples of a monomer capable of being copolymerized in the seventh polymer of the present invention may include those that are conventionally known as a positive resist, a negative resist, an anti-reflection coat material or an insulating film-forming material. For example, the monomer capable of being copolymerized may include a known monomer such as an acrylic acid derivative and a methacrylic acid derivative, which have a dry etching resistance-improving group or a soluble group involving acid dissociation, a carboxylic acid (including a derivative thereof) having an ethylene double bond causing alkali solubility, and known monomers used in the production of an acrylic resin. Specific examples of a monomer capable of being copolymerized may be the same as those described in the first polymer of the present invention.

As described in the first polymer of the present invention, the resin for a chemically amplified resist composition is required to have both a property for becoming soluble in an alkaline aqueous solution by an acid so as to realize high sensitivity and a structure having high carbon density so as to realize high dry etching resistance. The seventh polymer of the present invention is excellent in solubility in an organic solvent and heat resistance, and has little line edge roughness. When a structure having a property for becoming soluble in an alkaline aqueous solution by the action of an acid, or a structure having high dry etching resistance is introduced into such a polymer, an excellent resin for a chemically amplified resist composition can be obtained.

Examples of the structure having a functional group that is easily eliminated by the action of an acid and the structure having high carbon density may be the same as those described in the first polymer of the present invention.

In order to introduce the structure having a functional group that is easily eliminated by the action of an acid or the structure having high carbon density into the polymer, the monomer of the present invention may be copolymerized with a monomer having such a structure.

As a monomer having such a structure, for example, the one that is known as a raw material monomer for a resin for a chemically amplified resist composition can be used. A raw material monomer used for the polymer of the present invention is arbitrarily selected depending on light source used in lithography.

For example, when a KrF excimer laser or an electron beam is used as a light source, considering its high etching resistance, a polymer obtained by copolymerizing the monomer of the present invention with p-hydroxystyrene or a derivative thereof is preferably used. In this case, the proportion of the constitutional unit derived from the monomer of the present invention in the polymer is preferably 5% or more and is preferably 60% or less.

When an ArF excimer laser is used as a light source, a polymer obtained by copolymerizing the monomer of the present invention with a monomer having a cyclic hydrocarbon group is preferably used. Copolymerization with a monomer having a cyclic hydrocarbon group enables high etching resistance.

Among them, a polymer obtained by copolymerizing the monomer of the present invention, a monomer having a cyclic hydrocarbon group, a monomer having a hydrophilic functional group and/or a monomer having a lactone structure is preferable.

As described in the first polymer of the present invention, it is known that an acrylic copolymer obtained by copolymerizing a monomer having a cyclic hydrocarbon group and a monomer having a hydrophilic functional group, or an acrylic copolymer obtained by copolymerizing a monomer having a cyclic hydrocarbon group and a monomer having a lactone structure, is preferable as a resin for the ArF excimer laser lithography. Introduction of the monomer unit of the present invention into these polymers enables improvement of solubility in an organic solvent and heat resistance without impairing the resist performance such as high sensitivity, high resolution or high dry etching resistance, thereby providing an excellent resist pattern with only a little line edge roughness.

A monomer unit having a cyclic hydrocarbon group imparts high dry etching resistance to a polymer comprising the same. In particular, a monomer unit having a protecting group that is eliminated by an acid (a cyclic hydrocarbon group may also be a protecting group by itself) imparts also high sensitivity to the polymer comprising the same in photolithography using an ArF excimer laser with a wavelength of 193 nm. The monomer units having a cyclic hydrocarbon group may be of either a single type, or two or more types, if necessary.

Examples of the monomer unit having a cyclic hydrocarbon group may be the same as those described in the first polymer of the present invention, preferred examples being also the same.

A monomer unit having a hydrophilic functional group imparts adhesion to a substrate to a polymer comprising the same. In particular, a monomer unit having a protecting group that is eliminated by an acid imparts also high sensitivity to the polymer comprising the same in photolithography using an ArF excimer laser with a wavelength of 193 nm. Examples of a hydrophilic functional group may include a terminal hydroxy group, an alkyl-substituted ether group, a δ-valerolactonyl group, and a γ-butyrolactonyl group. It should be noted that some of the above listed hydrophilic functional groups are generally included in hydrophobic groups. However, since even such functional groups have hydrophilicity that is needed in the present invention, they are herein defined as a hydrophilic functional group. The monomer units having a hydrophilic functional group may be of either a single type, or two or more types, if necessary.

Examples of the monomer unit having a hydrophilic functional group may be the same as those described in the first polymer of the present invention, preferred examples being also the same.

A monomer unit having a lactone structure imparts high dry etching resistance and adhesion to a substrate to a polymer comprising the same. The monomer units having a lactone structure may be of either a single type, or two or more types, if necessary.

Examples of the monomer unit having a lactone structure may be the same as those described in the first polymer of the present invention, preferred examples being also the same.

The mass-average molecular weight of the seventh polymer of the present invention is not particularly limited. However, the mass-average molecular weight of the seventh polymer of the present invention is preferably 1,000 or more because the dry etching resistance is improved at the above range, thereby bettering the form of the resist. In addition, it is preferably 100,000 or less because the solubility in a resist solution is improved at the above range, thereby bettering the resolution.

7. Method of Producing Polymer of the Present Invention

The polymer of the present invention (resin for a resist composition) can be produced by a known polymerization method. In terms of the simple and easy production method, the polymer is preferably produced by the so-called drop polymerization method, in which a monomer solution obtained by previously dissolving a monomer and a polymerization initiator in an organic solvent is added by drops into an organic solvent that is maintained at a certain temperature.

The organic solvent used in the drop polymerization method is not particularly limited. However, a solvent that can dissolve both a monomer and the obtained copolymer is preferable. Examples of such a solvent may include 1,4-dioxane, isopropyl alcohol, acetone, tetrahydrofuran and ethyl lactate. The use amount of an organic solvent is not particularly limited, and it may be determined as appropriate.

The polymerization initiator used in the drop polymerization method is not particularly limited. Examples of the polymerization initiator may include an azo compound such as azobisisobutyronitrile or 2,2'-azobis(2,4-dimethylvaleronitrile), and an organic peroxide such as benzoyl peroxide. Moreover, a mercaptan such as n-butyl mercaptan, n-octyl mercaptan or 2-mercaptoethanol may be used as a chain transfer agent. The use amount of a polymerization initiator and the use amount of a chain transfer agent are not particularly limited, and they may be determined as appropriate.

In the drop polymerization method, polymerization temperature is not particularly limited, but in general, it is preferably within a range of 50° C. to 150° C.

A polymer solution produced by the drop polymerization method is diluted with a good solvent such as tetrahydrofuran or 1,4-dioxane (a mixture consisting of two or more solvents may also be used) to a suitable solution viscosity, if necessary. Then, the polymer solution is added by drops into a large amount of poor solvent such as heptane, methanol or water (a mixture consisting of two or more solvents may also be used), so as to deposit polymers. Thereafter, the obtained deposition is filtered, and is fully dried, so as to obtain the polymer of the present invention.

The step of depositing polymers by dropping a polymer solution into a large amount of poor solvent is called reprecipitation, and it is extremely effective to remove unreacted monomers, polymerization initiators and others that remain in the polymer solution. If these unreacted monomers and others remain in the polymer solution, they are likely to adversely affect the resist performance. Accordingly, it is preferable to remove them, if possible. This reprecipitation process may be omitted in some cases.

8. The Mixture of Polymers of the Present Invention

The above-described polymer of the present invention can be mixed with other polymers, if necessary. Mixed method is not particularly limited, and a known method can be used. The polymer of the present invention may be used singly or in combination of two or more types. Moreover, other polymers that are mixed with the polymer of the present invention may also be used singly or in combination of two or more types.

The polymer of the present invention is preferably used as a material for a resist composition, and particularly as a material for a chemically amplified resist composition. By using a polymer mixture comprising the polymer of the present invention and other polymers, the excellent performance as a resist composition, such as high solubility in an organic solvent, improved line edge roughness or improved dry etching resistance, can be obtained, and at the same time, it becomes possible to control the properties within the optimum range.

The polymer to be mixed with the polymer of the present invention is not particularly limited, but a polymer for a resist composition is preferable. Examples of such a polymer may include those that are conventionally known as a positive resist, a negative resist, an anti-reflection coat material or an insulating film-forming material. For example, the polymer may include those obtained by (co) polymerizing monomers such as an acrylic acid derivative and a methacrylic acid derivative, which have a dry etching resistance-improving group or a soluble group involving acid dissociation, a carboxylic acid (including a derivative thereof) having an ethylene double bond causing alkali solubility, and known monomers used in the production of an acrylic resin.

Examples of such an acrylic acid derivative may include an acryl ester in which the hydroxyl group of the carboxy group is protected with an acid-dissociating substituent, such as tert-butyl acrylate, tetrahydropyranyl acrylate, tetrahydrofuranyl acrylate, 1-methylcyclohexyl acrylate, 1-methyladamantyl acrylate, ethoxyethyl acrylate, ethoxypropyl acrylate, and the ester of acrylic acid and 2-hydroxy-3-pinanone; or an acryl ester in which the hydroxyl group of the carboxy group is protected with an non-acid-dissociating substituent, such as adamantyl acrylate, cyclohexyl acrylate, naphthyl acrylate, benzyl acrylate, 3-oxocyclohexyl acrylate, bicyclo[2.2.1]heptyl acrylate, tricyclodecanyl acrylate, the ester of acrylic acid and terpineol, and the ester of acrylic acid and 3-bromoacetone.

Examples of such a methacrylic acid derivative may include methacrylic acid derivatives corresponding to the above listed acrylic acid derivatives.

In addition, examples of such a carboxylic acid having an ethylene double bond may include acrylic acid; methacrylic acid; maleic acid; fumaric acid; norbornene or a norbornene derivative having an alkyl group, an alkyloxy group, a hydroxyl group, a hydroxyalkyl group, a carboxy group, an alkyloxycarbonyl group, or the like as a substituent; a vinyl ether derivative such as ethyl vinyl ether, cyclohexyl vinyl ether, and hydroxyethyl vinyl ether; a styrene derivative such as styrene, p-hydroxystyrene, p-methoxystyrene, and p-tert-butoxystyrene; and maleic anhydride.

Examples of a known monomer used in the production of an acrylic resin may include acrylic acid; methacrylic acid; or an acrylic acid derivative or an methacrylic acid derivative in which the hydrogen atom of these carboxylic acids is substituted with a group such as a methyl group, an ethyl group, a n-propyl group, an isopropyl group, a n-butyl group, a tert-butyl group, a n-hexyl group, an octyl group, a 2-ethylhexyl group, a lauryl group, a 2-hydroxyethyl group, a 2-hydroxypropyl group, a cyclopentyl group, a cyclohexyl group, a 2-hydroxyethyl group, a norbornyl group, a tricyclodecanyl group, an adamantyl group, a 2-methyl-2-adamantyl group, a tetrahydropyranyl group, a tetrahydrofuranyl group, or the like.

In addition to these acrylic resins, a polyhydroxystyrene resin, a cycloolefin resin, and the like may also be mixed with the polymer of the present invention.

Among them, a polymer comprising at least one of constitutional units represented by the above formula (8), (9) or (10) is preferable as a polymer to be mixed with the polymer of the present invention. The polymer comprising at least one of constitutional units represented by the above formula (8), (9) or (10) may be used singly or in combination of two or more types.

The content (the total content) of the polymer of the present invention in a polymer mixture is not particularly limited, but it is preferably 1% or more by mass, more preferably 10% or more by mass, and particularly preferably 20% or more by mass. Moreover, the content (the total content) of the polymer of the present invention in a polymer mixture is preferably 99% or less by mass, more preferably 90% or less by mass, and particularly preferably 80% or less by mass.

9. Resist Composition of the Present Invention

The resist composition of the present invention is obtained by dissolving the above-described polymer of the present invention and a photoacid generator in a solvent. The polymer of the present invention may be used singly or in combination of two or more types. When the above-described polymer mixture comprising the polymer of the present invention and a polymer other than those is used, the excellent performance as a resist composition, such as high solubility in an organic solvent, improved line edge roughness or improved dry etching resistance, can be obtained, and at the same time, it becomes possible to control the properties within the optimum range.

In terms of obtaining the sufficiently high effect of the present invention, the total content of the polymer of the present invention or the polymer mixture of the present invention is preferably 1% or more by mass, and more preferably 5% or more by mass in a resist composition (including a solvent). Moreover, in terms of handling, the total content of the polymer of the present invention or the polymer mixture of the present invention is preferably 80% or less by mass, and more preferably 50% or less by mass in a resist composition (including a solvent).

A photoacid generator used for the resist composition of the present invention can appropriately be selected from among acid generators that can be used for a resist composition. The photoacid generator can be used singly or in combination of two or more types.

Examples of such a photoacid generator may include an onium salt compound, a sulfone imide compound, a sulfone compound, a sulfonate compound, a quinone diazide compound, and a diazo methane compound. Of these, onium salt compounds such as a sulfonium salt, iodonium salt, phosphonium salt, diazonium salt and pyridinium salt are preferably used.

Specific examples of a photoacid generator may include triphenyl sulfonium triflate, triphenyl sulfonium hexafluoro antimonate, triphenylsulfonium naphthalene sulfonate, (hydroxy phenyl)benzyl methyl sulfonium toluene sulfonate, diphenyl iodonium triflate, diphenyl iodonium pyrene sulfonate, diphenyl iodonium dodecyl benzene sulfonate, and diphenyl iodonium hexafluoro antimonate.

The use amount of a photoacid generator is appropriately determined depending on the type of a photoacid generator used or other conditions, but in general, the amount is preferably within a range of 0.1 to 20 parts by mass based on 100 parts by mass of a polymer for resist (the polymer of the present invention or the polymer mixture of the present invention). By setting the use amount of a photoacid generator at 0.1 part or more by mass based on 100 parts by mass of a polymer for resist, a chemical reaction due to the catalytic action of an acid generated as a result of exposure can sufficiently take place. Moreover, by setting the use amount of a photoacid generator at 20 parts or less by mass based on 100 parts by mass of a polymer for resist, the stability of a resist composition is improved, and unevenness generated when the composition is applied, or scum or the like generated in a developing process is significantly reduced.

A solvent used for the resist composition of the present invention is arbitrarily selected depending on a purpose. However, the selection of the solvent may be subject to some constraints other than solubility of a resin, such as the ones regarding the homogeneity and appearance of a coating film, and safety.

Examples of a solvent usually used in the present invention may include linear ketones such as methyl ethyl ketone, 2-pentanone, and 2-hexanone; cyclic ketones such as cyclopentanone, and cyclohexanone; propylene glycol monoalkyl acetates such as propylene glycol monomethyl ether acetate, and propylene glycol monoethyl ether acetate; ethylene glycol monoalkyl ether acetates such as ethylene glycol monomethyl ether acetate, and ethylene glycol monoethyl ether acetate; propylene glycol monoalkyl ethers such as propylene glycol monomethyl ether, and propylene glycol monoethyl ether; ethylene glycol monoalkyl ethers such as ethylene glycol monomethyl ether, ethylene glycol monoethyl ether, and ethylene glycol monoisopropyl ether; diethylene glycol alkyl ethers such as diethylene glycol dimethyl ether, diethylene glycol monomethyl ether, and diethylene glycol diethyl ether; esters such as ethyl acetate, and ethyl lactate; alcohols such as n-propyl alcohol, isopropyl alcohol, n-butyl alcohol, tert-butyl alcohol, cyclohexanol, and 1-octanol; 1,4-dioxane; ethylene carbonate; and γ-butyrolactone. These solvents may be used singly or in combination of two or more types.

The use amount of a solvent is generally 200 parts or more by mass, and more preferably 300 parts or more by mass based on 100 parts by mass of a polymer for resist (the polymer of the present invention or the polymer mixture of the present invention). Moreover, the use amount of a solvent is generally 5000 parts or less by mass, and more preferably 2000 parts or less by mass based on 100 parts by mass of a polymer for resist (the polymer of the present invention or the polymer mixture of the present invention).

In addition, the resist composition of the present invention can further comprise various additives such as a surfactant, a quencher, a sensitizer, an antihalation agent, a storage stabilizer or an antifoaming agent, if necessary. Any additives that are known in the art can be used herein. The mixing amount of these additives is not particularly limited, and it may be determined as appropriate.

10. Pattern Formation Method of the Present Invention

Next, an example of the pattern formation method of the present invention will be explained.

First, the resist composition of the present invention is coated by spin-coating or the like on the surface of a substrate to be processed such as a silicon wafer, on which a pattern is to be formed. Then, the substrate, on which the resist composition is coated, is dried by the baking treatment (pre-bake), so that a resist film is formed on the substrate.

Next, a light with a wavelength of 250 nm or shorter, or an electron beam, is applied to the thus obtained resist film using a photomask (exposure). The light used in the exposure is preferably a KrF excimer laser or an ArF excimer laser, and particularly preferably an ArF excimer laser.

After the light irradiation (exposure), the baking treatment (PEB) is carried out as appropriate, and thereafter, the substrate is immersed in an alkaline developing solution, so as to eliminate the exposed portion by dissolving it therein (development). Any known alkaline developing solution can be used herein. After the development, the substrate is rinsed with pure water or the like, as appropriate. Thus, a resist pattern is formed on the substrate to be processed.

In general, a substrate on which a resist pattern is formed is appropriately subjected to the baking treatment (post exposure bake) so that the resist is reinforced. Portions having no resists are selectively etched. After the etching, the resist is generally eliminated using a release agent.

11. Other Uses of the Polymer of the Present Invention

I. Anti-Reflection Coat

The polymer of the present invention can also be used as an anti-reflection coat (cover film) material. In the pattern formation method, when a light source with a single and short wavelength is used for exposure, an incident light, a reflected light from a resist/substrate interface, and a re-reflected light from a resist/air interface of the reflected light from the resist/substrate interface, interfere with one another in the resist film, and, as a result, the substantial exposure amount in the film changes, and it causes a problem that the form of the resist pattern to be formed or the like is affected (phenomena of standing wave or multiple reflection). Consequently, there may be a case where the line width of the resist pattern becomes uneven or a case where notching (local distortion) is generated. So as to solve such a problem, a process of forming an anti-reflection coat on a resist film is employed. The polymer of the present invention is preferable also as an anti-reflection coat (cover film) material.

An anti-reflection coat composition, which is used for forming an anti-reflection coat, comprises the above-described polymer of the present invention and an organic solvent or water, and, if necessary, it further comprises a cross-linking agent, an acid generator or the like. The polymer of the present invention may be used singly or in combination of two or more types.

So as to increase solubility of a polymer compound in a solvent or to increase adhesion, acrylic acid alkyl ester, acrylonitrile, maleic anhydride, maleimide, N-methylmaleimide, itaconic anhydride, vinyl pyrrolidone, vinyl acetate, or the like may be copolymerized, and constitutional units derived from these compounds may also be introduced into the polymer of the present invention.

In terms of obtaining the sufficient effect by introduction of the constitutional units, the proportion of the constitutional unit is preferably 5 mol % or more, and particularly preferably 10 mol % or more in the polymer. In addition, in terms of obtaining the good film-forming property, the proportion of the constitutional unit is preferably 50 mol % or less, and particularly preferably 40 mol % or less in the polymer.

Furthermore, a constitutional unit having absorbance may be introduced into the polymer of the present invention, so as to impart absorbance to the polymer. Examples of a monomer copolymerized with the polymer of the present invention to introduce a constitutional unit having absorbance may include a salicylate compound, a benzophenone compound, a benzotriazole compound, a cyanoacrylate compound, an azo compound, a polyene compound, an anthraquinone compound, a bisphenyl sulfone compound, a bisphenyl sulfoxide compound, an anthracene compound, a diphenyl sulfone compound, a melamine compound, an urea compound, a guanamine compound, an acetoguanamine compound, a benzoguanamine compound, a glycol uryl compound, a succinyl amide compound, and an ethylene urea compound.

In terms of obtaining the sufficient effect by introduction of the constitutional units having absorbance, the proportion of the constitutional unit is preferably 5 mol % or more, and particularly preferably 10 mol % or more in the polymer. In addition, in terms of obtaining the good film-forming property, the proportion of the constitutional unit having absorbance is preferably 50 mol % or less, and particularly preferably 40 mol % or less in the polymer.

Also, in addition to the polymer of the present invention, a resin having absorbance may be mixed, so as to impart absorbance to the polymer composition. Examples of a resin having absorbance may include a resin binder comprising a quinolinyl group, a phenanthrenyl group, an acridinyl group or an alkylene anthryl group; a resin obtained by polymerizing an epoxy resin with a dye having a substituent having an anthracene ring, a naphthalene ring or the like; a melamine resin; an urea resin; a benzoguanamine resin; and a glycol uryl resin.

In terms of obtaining the sufficient effect by mixing the above resins, the mixing amount of the resin is preferably 5 parts by mass or more, and particularly preferably 10 parts by mass or more based on 100 parts by mass of the total resins. In addition, in terms of obtaining the good film-forming property, the mixing amount of the resin is preferably 50 parts by mass or less, and particularly preferably 40 parts by mass or less based on 100 parts by mass of the total resins.

Furthermore, in addition to the polymer of the present invention, various water-soluble polymers such as a polyvinyl alcohol, a polyacrylic acid, a polymethacrylic acid, a polyvinyl pyrrolidone, a polyethylene oxide, an amylose, a dextran, a cellulose, a pullulan, and a functional fluorocarbon compound such as a perfluoroalkyl carboxylic acid polymer may be mixed, so as to improve film-forming property.

In terms of obtaining the sufficient effect by mixing the above resins, the mixing amount of the resin is preferably 5 parts by mass or more, and particularly preferably 10 parts by mass or more based on 100 parts by mass of the total resins. In addition, in terms of obtaining the good adhesion to a substrate, the mixing amount of the resin is preferably 50 parts by mass or less, and particularly preferably 40 parts by mass or less based on 100 parts by mass of the total resins.

No diffusion of a low molecular weight component into a resist layer is one of the properties required for an anti-reflection coat. Accordingly, there is generally applied a method in which thermal cross-linking is conducted by the bake after the spin coating of an anti-reflection coat composition. In this case, a cross-linking substituent is introduced into the polymer to be used, and a cross-linking agent is added to the anti-reflection coat composition.

Examples of a cross-linking agent may include a melamine compound, a guanamine compound, a glycol uryl compound or an urea compound, which have at least one substituent selected from a group consisting of a methylol group, an alkoxymethyl group and an acyloxymethyl group, an epoxy compound, a thioepoxy compound, an isocyanate compound, an azide compound, and a compound having a double bond such as an alkenyl ether group. In addition, these compounds may be used as an additive, but they may also be introduced into the side chain of the polymer as a pendant group.

In terms of sufficient prevention of mixing with a resist, the mixing amount of a cross-linking agent is preferably 5 parts by mass or more, and particularly preferably 10 parts by mass or more based on 100 parts by mass of the total resins comprising the polymer of the present invention. In addition, in terms of sufficient prevention of decrease in antireflection effect and generation of crack of the film after cross-linking, the mixing amount of a cross-linking agent is preferably 50 parts by mass or less, and particularly preferably 40 parts by mass or less based on 100 parts by mass of the total resins comprising the polymer of the present invention.

And, so as to further promote a thermal cross-linking reaction, an acid generator may be added to the anti-reflection coat composition. Some acid generators generate acid by thermal decomposition, and others generate acid by exposure to light. Any acid generator can be used herein.

An organic solvent used in the anti-reflection coat composition is not particularly limited, as long as a polymer, a cross-linking agent, an acid generator and other additives can be dissolved therein. Examples of such an organic solvent may include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol monomethyl ether acetate, and propylene glycol mono-tert-butyl ether acetate. These solvents may be used singly or in combination of two or more types.

In addition, a water-soluble organic solvent can be used with water. Examples of such a water-soluble organic solvent may include alcohols such as methylalcohol, ethylalcohol, and isopropylalcohol; ketones such as acetone and methyl ethyl ketone; esters such as methyl acetate and ethyl acetate; and polar solvent such as dimethylformamide, dimethylsulfoxide, methyl cellosolve, cellosolve, butyl cellosolve, cellosolve acetate, butyl carbitol, and carbitol acetate. These organic solvents may be used singly or in combination of two or more types.

The mixing amount of a solvent is preferably 500 parts by mass or more, and more preferably 5,000 parts by mass or more based on 100 parts by mass of the total resins comprising the polymer of the present invention. In addition, the mixing amount of a solvent is preferably 10,000 parts by mass or less, and more preferably 5,000 parts by mass or less based on 100 parts by mass of the total resins comprising the polymer of the present invention.

Next, an example of the anti-reflection coat formation methods and an example of the pattern formation methods will be explained.

First, the above-described anti-reflection coat composition is coated on a substrate by spin-coating using a spinner or the like. Then, the substrate, on which the anti-reflection coat composition is coated, is subjected to a heat treatment at a temperature within a range of 100° C. to 300° C., so that an anti-reflection coat with thickness within a range of 0.03 to 0.5 µm is formed. The heat treatment causes a cross-linking reaction of a resin component in the anti-reflection coat composition, and the anti-reflection coat to be formed becomes insoluble in an alkaline solution.

After forming an anti-reflection coat as described above, a resist composition is coated thereon by spin-coating using a spinner or the like, and then it is dried, so as to form a resist layer. Thereafter, a radiation such as a KrF excimer laser or an ArF excimer laser is applied to the thus obtained resist layer through a desired mask pattern, for example, by using a reduced projection exposure apparatus. After the light irradiation, a heat treatment is carried out as appropriate, and then, a development is carried out using a developing solution, for example, an alkaline aqueous solution such as 1% to 10% by mass of a tetramethylammonium hydroxide aqueous solution. If the resist is a positive type, the exposed portion is selectively dissolved and eliminated to form a photoresist pattern, which is faithful to the mask pattern. On the other hand, if the resist is a negative type, the unexposed portion is selectively dissolved and eliminated to form a photoresist pattern, which is faithful to the mask pattern.

A resist to which the above-described anti-reflection coat composition comprising the polymer of the present invention is applied, is not particularly limited, but a chemically amplified resist is preferable. Moreover, the anti-reflection coat may be formed either on a resist film, or under the resist film.

II. Radiation-Sensitive Composition

The polymer of the present invention can also be used as a radiation-sensitive composition, which is used for a negative resist such as a mask for the formation and lithography of a insulating film of a liquid crystal display device, a semiconductor integrated circuit device, a magnetic head device, a solid-state image pickup device, an organic EL device, and the like. The term "radiation" is used herein to mean an ultraviolet ray, a far ultraviolet ray, an X-ray, an electron beam, a molecular beam, a γ-ray, a synchrotron radiation ray, a proton beam, or the like.

A radiation-sensitive composition comprises the above-described polymer of the present invention, a radiation-sensitive acid generator, a cross-linking agent which cross-links by the action of an acid, and an organic solvent or water, and, if necessary, it further comprises an alkali-soluble resin or the like. The polymer of the present invention may be used singly or in combination of two or more types.

In this case, in terms of the high heat resistance, the mass-average molecular weight of the polymer of the present invention is preferably 1000 or more, more preferably 2000 or more, and particularly preferably 3000 or more. In addition, in terms of the fast developing rate, the mass-average molecular weight of the polymer of the present invention is preferably 100000 or less, more preferably 40000 or less, and particularly preferably 30000 or less.

A radiation-sensitive acid generator is not particularly limited, as long as the dissolution rate of the polymer of the present invention in an alkaline aqueous solution increases by an acid generated therefrom. Examples of such a radiation-sensitive acid generator may include the photoacid generators used in the above-described resist composition of the present invention, and known acid generators such as an onium salt, a halogen-containing compound, a diazoketone compound, a diazomethane compound, a sulfone compound, a sulfonate compound and a sulfoneimide compound. These radiation-sensitive acid generators may be used singly or in combination of two or more types.

In terms of forming a good pattern, the additive amount of a radiation-sensitive acid generator is preferably 0.01 part by mass or more, and more preferably 0.1 part by mass or more based on 100 parts by mass of the polymer. Moreover, in terms of maintaining sufficient affinity for a developing solution and preventing generation of defective development or the like, the additive amount of a radiation-sensitive acid generator is preferably 50 parts by mass or less, and more preferably 10 parts by mass or less based on 100 parts by mass of the polymer.

Examples of a cross-linking agent which cross-links by the action of an acid may include a bisphenol A-based epoxy compound, a bisphenol F-based epoxy compound, a bisphenol S-based epoxy compound, a novolac resin-based epoxy compound, a resol resin-based epoxy compound, a poly (hydroxystyrene)-based epoxy compound, a methylol group-containing melamine compound, a methylol group-containing benzoguanamine compound, a methylol group-containing urea compound, a methylol group-containing phenol compound, an alkoxyalkyl group-containing melamine compound, an alkoxyalkyl group-containing benzoguanamine compound, an alkoxyalkyl group-containing urea compound, an alkoxyalkyl group-containing phenol compound, a carboxymethyl group-containing melamine resin, a carboxymethyl group-containing benzoguanamine resin, a carboxymethyl group-containing urea resin, a carboxymethyl group-containing phenol resin, a carboxymethyl group-containing melamine compound, a carboxymethyl group-containing benzoguanamine compound, a carboxymethyl group-containing urea compound, and a carboxymethyl group-containing phenol compound. Such a cross-linking agent may be used singly or in combination of two or more types.

In terms of prevention of decrease in residual ratio of the film, distortion or swelling of a pattern, and the like, the introduction ratio of a cross-linking functional group is preferably 5 mol % or more, more preferably 10 mol % or more, and particularly preferably 15 mol % or more based on the total acid functional groups of the polymer of the present invention that are generated by a radiation-sensitive acid generator. Moreover, in terms of obtaining the good development property of the exposed portion, the introduction ratio of a cross-linking functional group is preferably 60 mol % or less, more preferably 50 mol % or less, and particularly preferably 40 mol % or less based on the total acid functional groups of the polymer of the present invention that are generated by a radiation-sensitive acid generator.

Examples of an organic solvent used for the radiation-sensitive composition may include esters such as ethyl acetate, butyl acetate, amyl acetate, ethyl propionate, methyl butyrate, methyl benzoate, methyl lactate, ethyl lactate, ethyl pyruvate, methyl β-isobutyrate, methyl 3-methoxypropionate, ethyl 3-ethoxypropionate, and γ-butyrolactone; cellosolves such as methyl cellosolve, ethyl cellosolve, and butyl cellosolve; cellosolve esters such as methyl cellosolve acetate, ethyl cellosolve acetate, and butyl cellosolve acetate; propylene glycol esters such as propylene glycol monomethyl ether acetate and propylene glycol monoethyl ether acetate; ethers such as 1,2-dimethoxyethane, 1,2-diethoxyethane, tetrahydrofuran, and anisole; ketones such as methyl ethyl ketone, methyl isobutyl ketone, methyl n-amyl ketone, cyclohexanone, and isophorone; aprotic polar solvent such as dimethylformamide, dimethylacetoamide, N-methylpyrrolidone, dimethyl sulfoxide, sulfolane; alcohols such as methanol and ethanol; and aromatic hydrocarbons such as toluene and xylene. These solvents may be used singly or in combination of two or more types.

To the radiation-sensitive composition, an alkali-soluble resin may further be added. Examples of such an alkali-soluble resin may include a novolac resin, a hydrogenated novolac resin, an acetone-pyrogallol resin, a poly-o-hydroxystyrene, a poly-m-hydroxystyrene, a poly-p-hydroxystyrene, a hydrogenated polyhydroxystyrene, a halogen- or alkyl-substituted polyhydroxystyrene, a hydroxystyrene-N-substituted maleimide copolymer, an o/p- and m/p-hydroxystyrene copolymer, a styrene-maleic anhydride copolymer, a styrene-hydroxystyrene copolymer, an α-methylstyrene-hydroxystyrene copolymer, a carboxyl group-containing methacrylic resin, and derivatives thereof. These alkali-soluble resins may be used singly or in combination of two or more types.

In terms of obtaining the sufficient effects that a pattern becomes sharper during the development, or the like, the additive amount of an alkali-soluble resin is preferably 5 mol % or more, and particularly preferably 10 mol % or more. Moreover, in terms of stability of the mixture, it is preferably 50 mol % or less, and particularly preferably 40 mol % or less.

An additive such as a surfactant, a sensitizer, a stabilizer, an antifoaming agent or an acid-diffusion inhibitor can be mixed in the radiation-sensitive composition, if necessary.

The total solid content of the radiation-sensitive composition is preferably 5% by mass or more, and more preferably 10% by mass or more. Moreover, the total solid content of the radiation-sensitive composition is preferably 50% by mass or less, and more preferably 40% by mass or less.

The radiation-sensitive composition is prepared by uniformly dissolving the polymer of the present invention, and the like in a solvent so that the total solid content is within the above range, and then filtrating the obtained solution using, for example, a filter with a pore size of approximately 0.2 μm.

Next, an example of methods of forming an insulating film using the radiation-sensitive resin composition comprising the polymer of the present invention will be explained.

First, the above-described radiation-sensitive resin composition is coated on the surface of a substrate. Examples of a coating method may include a spray coating method, a roll coating method, a spin coating method, and a bar coating method. Then, the solvent is removed by pre-bake, so that a coating film is formed on the substrate. The conditions for pre-bake vary according to the type and the content of each component, and the like, but in general, the preferable conditions are that the treating temperature is within a range of 70° C. to 90° C. and the treating time is within a range of 1 to 15 minutes.

Thereafter, a radiation such as an ultraviolet ray is applied to the thus obtained coating film through a predetermined pattern mask. After the irradiation, a development is carried out using a developing solution so as to eliminate the unnecessary portion, so that a predetermined pattern is formed. Any development methods, including a liquid-putting method, a dipping method and a shower method, may be employed. The developing time is generally within a range of 30 to 180 seconds.

As a developing solution, an alkaline aqueous solution such as an aqueous solution of an inorganic alkali such as sodium hydroxide, potassium hydroxide, sodium carbonate, sodium silicate, sodium metasilicate, and ammonia; an aqueous solution of a primary amine such as ethylamine and n-propylamine; an aqueous solution of a secondary amine such as diethylamine and di-n-propylamine; an aqueous solution of a tertiary amine such as trimethylamine, methyldiethylamine, dimethylethylamine, and triethylamine; an aqueous solution of a tertiary amine such as dimethylethanolamine, methyldiethanolamine, and triethanolamine; an aqueous solution of a tertiary amine such as pyrrole, piperidine, N-methylpiperidine, N-methylpyrrolidine, 1,8-diazabicyclo[5.4.0]-7-undecene, and 1,5-diazabicyclo[4.3.0]-5-nonene; an aqueous solution of an aromatic tertiary amine such as pyridine, collidine, lutidine, and quinoline; and an aqueous solution of a quaternary ammonium salt such as tetramethylammonium hydroxide and tetraethylammonium hydroxide can be used. Moreover, an aqueous solution obtained by adding an appropriate amount of a water-soluble organic solvent such as methanol or ethanol, and a surfactant to the above alkaline aqueous solution, can also be used as a developing solution.

After the development, the unnecessary portion is eliminated by washing with running water for 30 to 90 seconds, followed by air-drying with compressed air or compressed nitrogen, to form a pattern. A radiation such as an ultraviolet ray is applied to the thus formed pattern, and thereafter, a heat treatment is carried out, using a heating apparatus such as a hot plate or an oven, at a predetermined temperature, for example, within a range of 180° C. to 250° C., for a predetermined time, for example, for 5 to 60 minutes on a hot plate, or for 30 to 90 minutes in an oven, so that an insulating film of interest can be obtained.

EXAMPLES

Next, the present invention will be explained further in detail by the following examples. However, the examples are not intended to limit the scope of the present invention.

The term "part" is herein used to mean "part by mass", unless otherwise specified.

The measurement of properties of the produced copolymer was carried out by the following methods.

<Mass-Average Molecular Weight>

The mass-average molecular weight of the copolymer was determined by gel permeation chromatography (hereinafter referred to as GPC) and expressed in terms of polystyrene standards. Chloroform or tetrahydrofuran was used as a solvent.

<Average Copolymerization Composition of Copolymers (mol %)>

The average copolymerization composition of copolymers was determined by $^1$H-NMR measurement. Deuterated Chloroform, deuterated dimethyl sulfoxide, or deuterated acetone was used as a solvent.

<Production of Monomers>

Example 1

25.0 g (0.1 mol) of 2,5-dimethyl-2-(1-adamantyl)-1,3-dioxolan-4-one, 19.6 g (0.11 mol) of N-bromosuccinimide and 240 g of heptane were placed in a 500 ml egg-plant type flask equipped with a reflux condenser, and while the mixture was in a slurry state, the temperature was increased to the reaction temperature, 60° C. under stirring.

When the mixture was stirred at 60° C. for about 2 hours, the reaction solution became brown. When the reaction solution was further stirred for 2 hours, it became transparent. After the reaction solution was cooled in an ice bath, it was filtered to remove succinimide, and then, the solvent was removed. The obtained transparent liquid was purified with a column, so as to obtain 28.6 g of 5-bromo-2,5-dimethyl-2-(1-adamantyl)-1,3-dioxolan-4-one (Formula (18), yield: 87%).

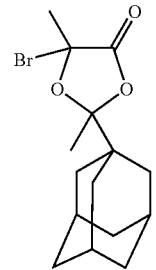

(18)

Elementary analysis: C 54.56%, H 6.64%, N 0%, O 14.73% (Theoretical value: C 54.72%, H 6.43%, N 0%, O 14.58%)

Bromine content (by flask combustion/ion chromatography): 24.2% (Theoretical value: 24.27%)

$^1$H-NMR (270 MHz, Internal standard: CDCl$_3$, δppm): 1.40 to 1.72 (m, adamantyl group), 1.73 (s, 3H), 2.20 (s, 3H)

Infrared absorption spectrum (KBr tablet, cm$^{-1}$): 2908, 2851, 1809, 1452, 1385, 1282, 1223, 1195, 1167, 1063, 943, 928

16.5 g (0.05 mol) of the obtained 5-bromo-2,5-dimethyl-2-(1-adamantyl)-1,3-dioxolan-4-one was placed in a 100 ml egg-plant type flask, and 73.1 g (1.0 mol) of N,N-dimethylformamide was added thereto, followed by intensively stirring at 40° C. for 2 hours. After completion of the stirring, the mixture was transferred into a 500 ml separatory funnel, and 200 g of isopropyl ether was added thereto, followed by fully shaking. Thereafter, the obtained mixture was left at rest, so as to separate the mixture into two layers. And then, the N,N-dimethylformamide phase that was a lower layer was removed. The isopropyl ether phase that was a upper layer washed with water to remove N,N-dimethylformamide dissolved therein. Thereafter, isopropyl ether was removed, so as to obtain white crystals. The obtained white crystals were recrystallized from hexane, so as to obtain 10.9 g of 5-methylene-2-(1-adamantyl)-2-methyl-1,3-dioxolan-4-one at a purity of 99.8% (Formula (19), yield: 88%).

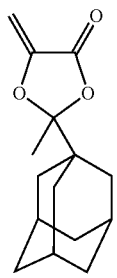

(19)

Elementary analysis: C 70.40%, H 8.14%, N 0%, O 19.38% (Theoretical value: C 72.55%, H 8.12%, N 0%, O 19.33%)

Figure 2:
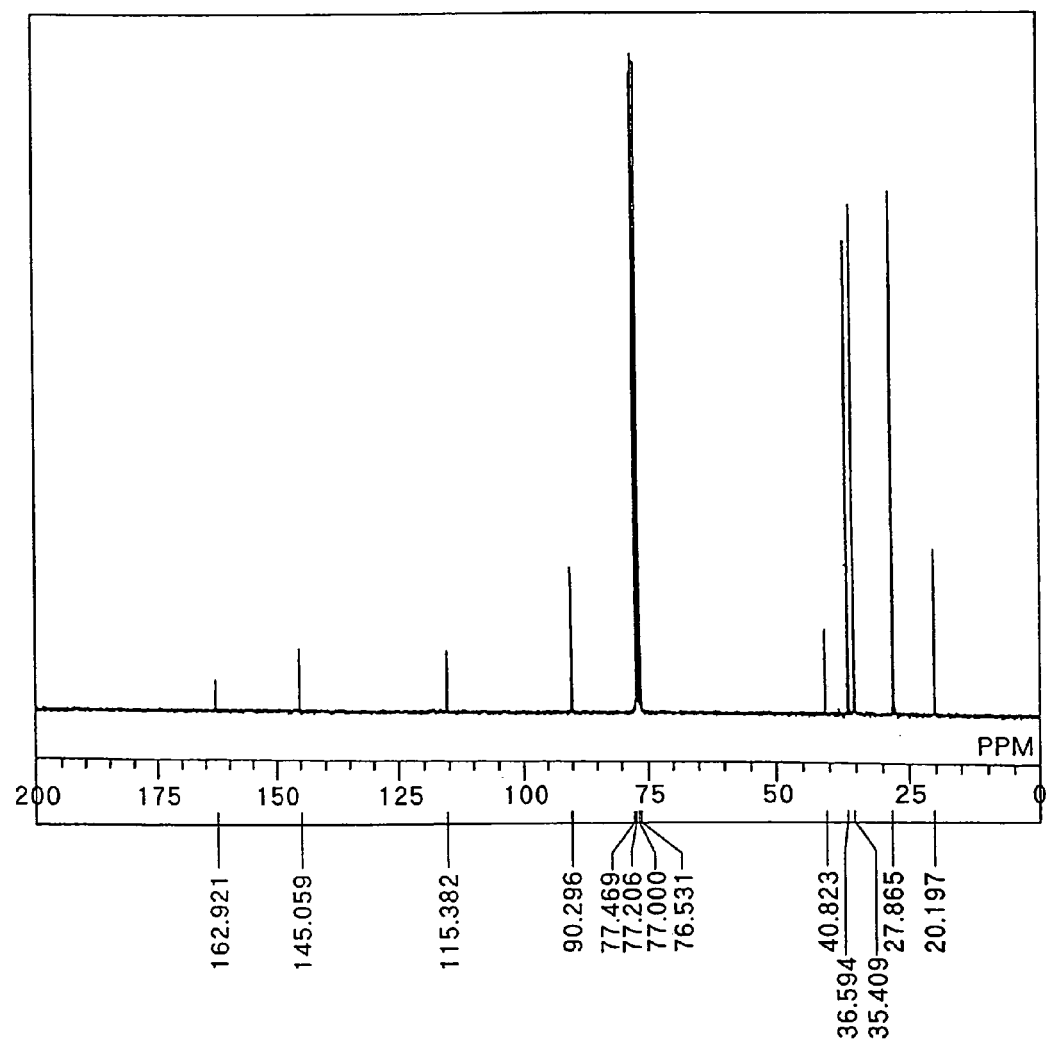
FIG. 2 is a $^{13}$C-NMR spectrum of the compound represented by the formula (19), which was obtained in Example 1.

The $^1$H-NMR spectrum (270 MHz, Internal standard: CDCl$_3$) of the compound of formula (19) is shown in FIG. 1, and the $^{13}$C-NMR spectrum (270 MHz, Internal standard: CDCl$_3$) of the same compound is shown in FIG. 2.

Example 2

22.2 g (0.1 mol) of spiro[adamantan-2,2'-(5'-methyl-1',3'-dioxolan-4'-one)], 21.4 g (0.12 mol) of N-bromosuccinimide and 200 g of cyclohexane were placed in a 500 ml egg-plant type flask equipped with a reflux condenser, and while the mixture was in a slurry state, the temperature was increased to the reaction temperature, 60° C. under stirring.

When the mixture was stirred at 60° C. for about 2 hours, the reaction solution became brown. When the reaction solution was further stirred for 2 hours, it became transparent. After the reaction solution was cooled in an ice bath, it was filtered to remove succinimide, and then, the solvent was removed. The deposited crystals were recrystallized from hexane, so as to obtain 25.6 g of spiro[adamantan-2,2'-(5'-bromo-5'-methyl-1',3'-dioxolan-4'-one)] (Formula (20), yield: 85%).

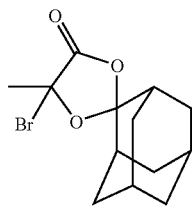

(20)

Elementary analysis: C 51.70%, H 5.82%, N 0%, O 16.19% (Theoretical value: C 51.84%, H 5.69%, N 0%, O 15.94%)

Bromine content (by flask combustion/ion chromatography): 26.4% (Theoretical value: 26.53%)

$^1$H-NMR (270 MHz, Internal standard: CDCl$_3$, δppm): 1.66 to 2.07 (m, adamantyl group), 2.20 (s, 3H)

Infrared absorption spectrum (KBr tablet, cm$^{-1}$): 2917, 2860, 1804, 1455, 1388, 1290, 1179, 1111, 1091, 1065, 1022, 988, 929

15.1 g (0.05 mol) of the obtained spiro[adamantan-2,2'-(5'-bromo-5'-methyl-1',3'-dioxolan-4'-one)] was placed in a 500 ml egg-plant type flask, and 200 g of cyclohexane was added thereto and dissolved therein. Thereafter, 36.5 g (0.5 mol) of N,N-dimethylformamide was added thereto, followed by intensively stirring at room temperature for 2 hours. After completion of the stirring, the mixture was transferred into a 500 ml separatory funnel and was left at rest, so as to separate the mixture into two layers. And then, the lower N,N-dimethylformamide layer was removed. The upper cyclohexane layer washed with water to remove N,N-dimethylformamide dissolved therein. Thereafter, cyclohexane was removed, so as to obtain white crystals. The obtained white crystals were recrystallized from hexane, so as to obtain 9.3 g of spiro[adamantan-2,2'-(5'-methylene-1',3'-dioxolan-4'-one)] at a purity of 99.6% (Formula (21), yield: 85%).

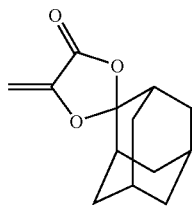

(21)

Elementary analysis: C 70.69%, H 7.35%, N 0%, O 21.84% (Theoretical value: C 70.89%, H 7.32%, N 0%, O 21.79%)

Figure 3:
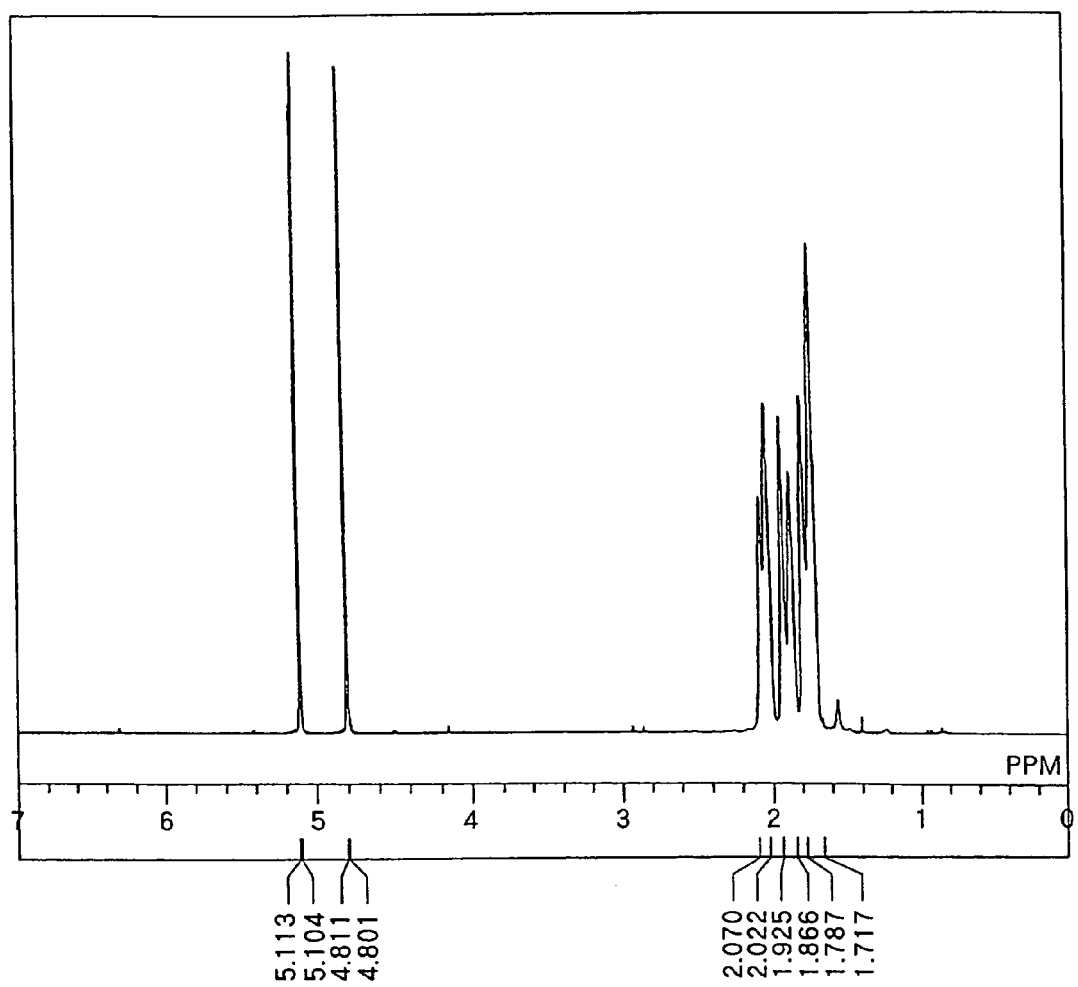
FIG. 3 is a $^1$H-NMR spectrum of the compound represented by a formula (21), which was obtained in Example 2.
Figure 4:
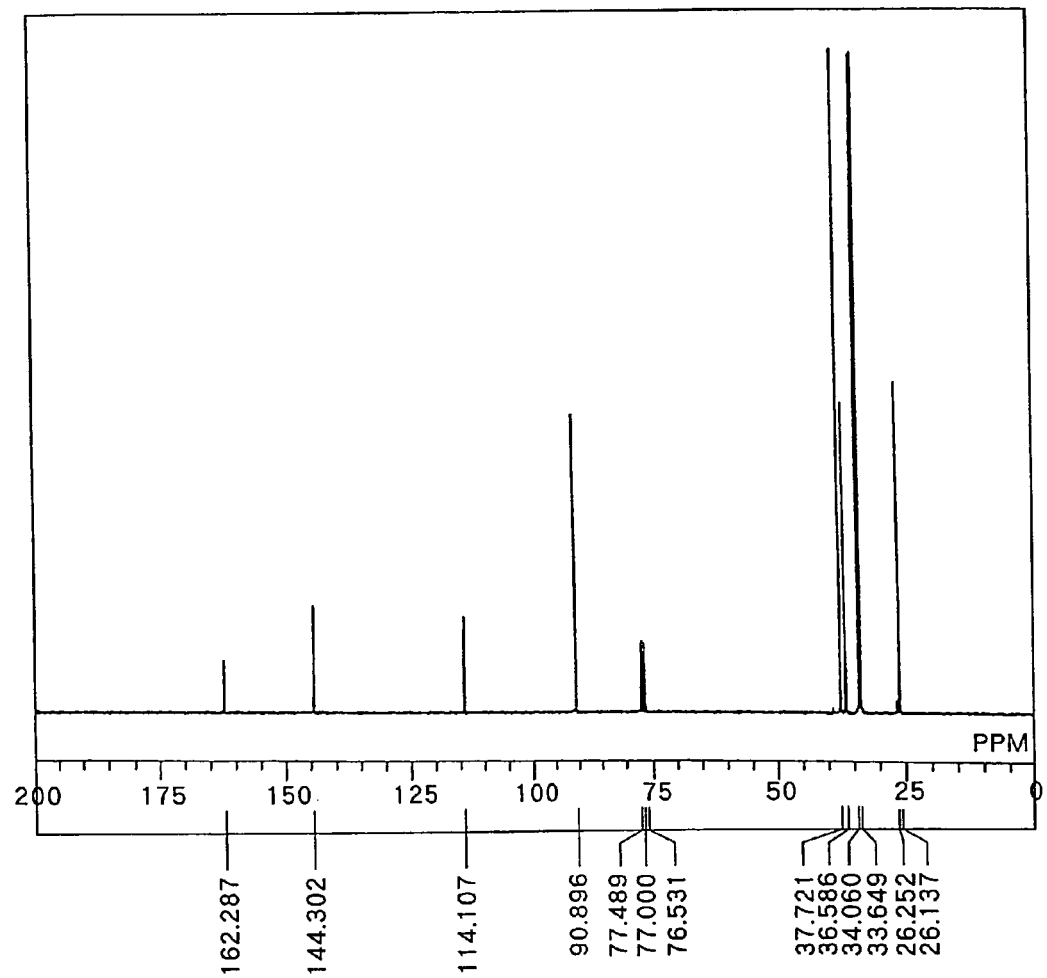
FIG. 4 is a $^{13}$C-NMR spectrum of the compound represented by the formula (21), which was obtained in Example 2.

The $^1$H-NMR spectrum (270 MHz, Internal standard: CDCl$_3$) of the compound of formula (21) is shown in FIG. 3, and the $^{13}$C-NMR spectrum (270 MHz, Internal standard: CDCl$_3$) of the same compound is shown in FIG. 4.

Example 3

18.2 g (0.1 mol) of spiro[norbornan-2,2'-(5'-methyl-1',3'-dioxolan-4'-one)], 19.6 g (0.11 mol) of N-bromosuccinimide and 280 g of cyclohexane were placed in a 500 ml egg-plant type flask equipped with a reflux condenser, and while the mixture was in a slurry state, the temperature was increased to the reaction temperature, 60° C. under stirring.

When the mixture was stirred at 60° C. for about 2 hours, the reaction solution became brown. When the reaction solution was further stirred for 2 hours, it became transparent. After the reaction solution was cooled in an ice bath, it was analyzed. As a result, it was found that 25.1 g of spiro[norbornan-2,2'-(5'-bromo-5'-methyl-1',3'-dioxolan-4'-one)] was contained in the reaction solution (Formula (22), yield: 96%).

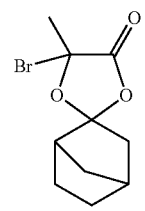

(22)

The obtained reaction solution was transferred into a 500 ml egg-plant type flask, and 73.0 g (1.0 mol) of N,N-dimethylformamide was added thereto, followed by intensively stirring at room temperature for 2 hours. Succinimide generated as a by-product in the previous step was dissolved in N,N-dimethylformamide during the stirring. After completion of the stirring, insoluble products were removed from the reaction solution by filtration, and the obtained filtrate was transferred into a 500 ml separatory funnel. The solution was left at rest, so as to separate it into two layers. And then, the lower N,N-dimethylformamide layer was removed. The upper cyclohexane layer washed with water to remove N,N-dimethylformamide dissolved therein. Thereafter, cyclohexane was removed, so as to obtain white crystals. The obtained white crystals were recrystallized from hexane, so as to obtain 15.5 g of spiro[norbornan-2,2'-(5'-methylene-1,1',3'-dioxolan-4'-one)] at a purity of 99.5% (Formula (23), yield: 86%).

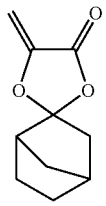

(23)

Elementary analysis: C 66.39%, H 6.84%, N 0%, O 27.03% (Theoretical value: C 66.65%, H 6.71%, N 0%, O 26.64%)

Figure 5:
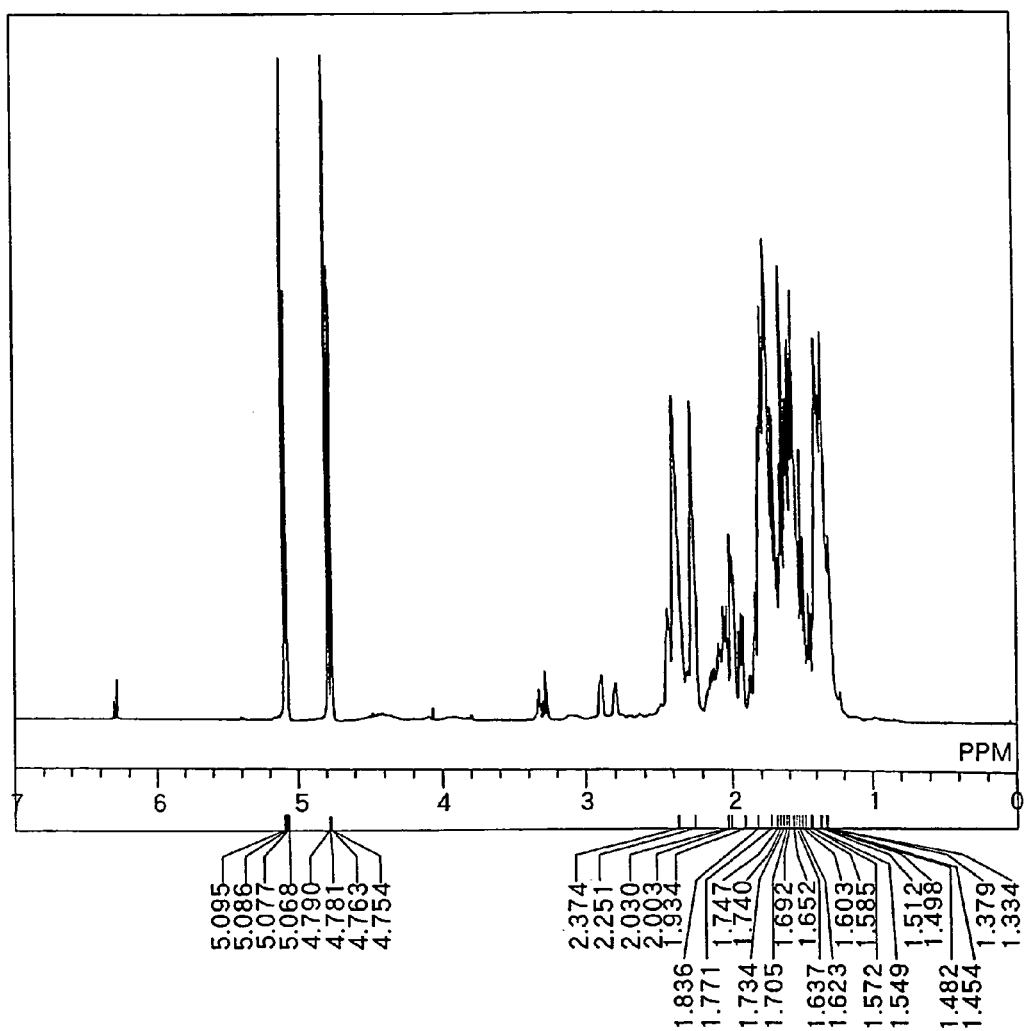
FIG. 5 is a $^1$H-NMR spectrum of the compound represented by a formula (23), which was obtained in Example 3.
Figure 6:
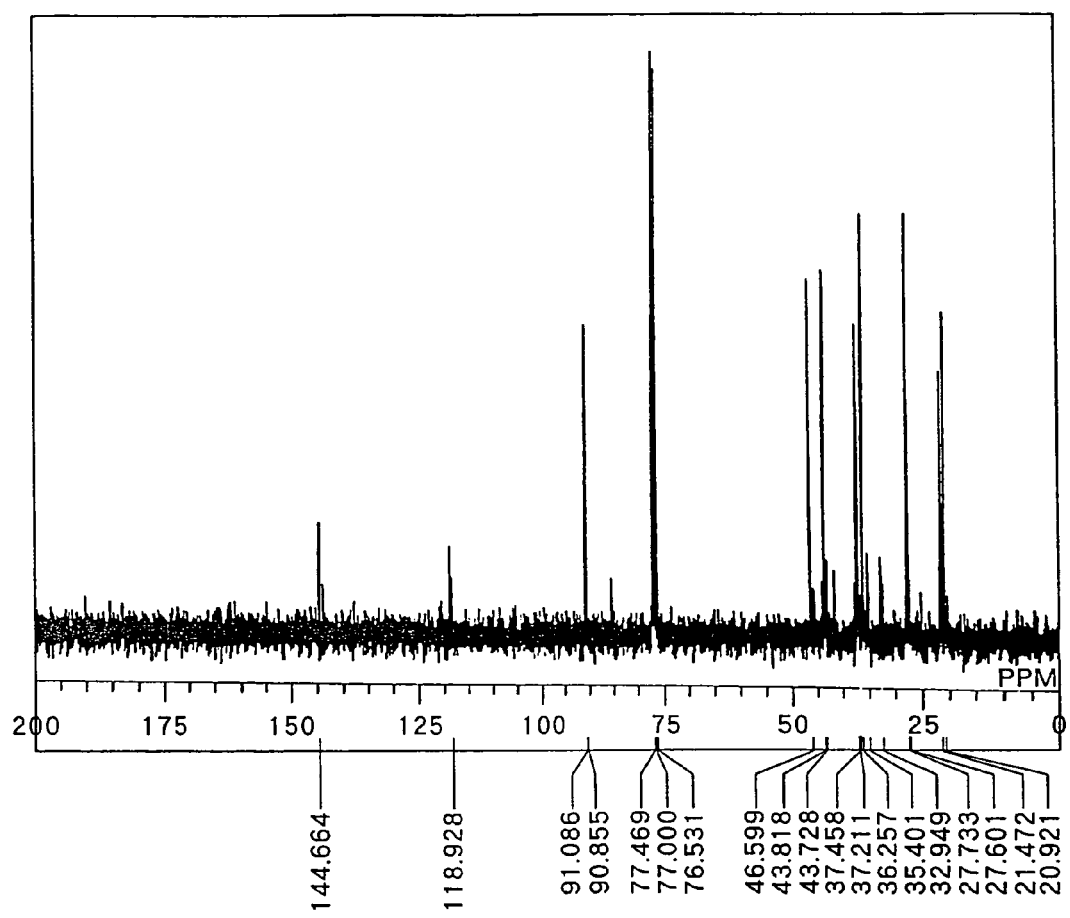
FIG. 6 is a $^{13}$C-NMR spectrum of the compound represented by the formula (23), which was obtained in Example 3.

The $^1$H-NMR spectrum (270 MHz, Internal standard: CDCl$_3$) of the compound of formula (23) is shown in FIG. 5, and the $^{13}$C-NMR spectrum (270 MHz, Internal standard: CDCl$_3$) of the same compound is shown in FIG. 6.

Example 4

A mixture obtained by dissolving 16.4 g (0.05 mol) of 5-bromomethyl-2-(1-adamantyl)-2-methyl-1,3-dioxolan-4-one in 58 g of isopropyl ether was placed in a flask equipped with an agitator, a thermometer, a condenser and a dropping funnel. 36.5 g (0.5 mol) of N,N-dimethylformamide was added by drops thereto, followed by intensively stirring at room temperature for 4 hours. After completion of the stirring, insoluble products were removed from the reaction solution by filtration, and the obtained filtrate was transferred into a 500 ml separatory funnel. The solution was left at rest, so as to separate it into two layers, and the lower N,N-dimethylformamide layer was removed. The upper isopropyl ether layer washed with water to remove N,N-dimethylformamide dissolved therein. Thereafter, isopropyl ether was removed, so as to obtain white crystals. The obtained white crystals were recrystallized from hexane, so as to obtain 6.6 g of 5-methylene-2-(1-adamantyl)-2-methyl-1,3-dioxolan-4-one (hereinafter referred to as AdMDO) (yield: 53%).

Comparative Example 1

25.0 g (0.1 mol) of 2,5-dimethyl-2-(1-adamantyl)-1,3-dioxolan-4-one, 19.6 g (0.11 mol) of N-bromosuccinimide and 240 g of heptane were placed in a 500 ml egg-plant type flask equipped with a reflux condenser, and while the mixture was in a slurry state, the temperature was increased to the reaction temperature, 80° C. under stirring.

When the mixture was stirred at 80° C. for about 1 hour, the reaction solution became brown. As a result of analyzing the reaction solution immediately before it became brown, it was found that the reaction solution contained 5-bromo-2,5-dimethyl-2-(1-adamantyl)-1,3-dioxolan-4-one corresponding to 3% of the raw materials and adamantyl methyl ketone corresponding to 4% of the raw materials. When the reaction solution was further stirred for 2 hours, it became transparent. After the reaction solution was cooled in an ice bath, it was filtered to remove succinimide. As a result of analyzing the reaction solution, it was found that the reaction solution contained only 3.6 g of 5-bromo-2,5-dimethyl-2-(1-adamantyl)-1,3-dioxolan-4-one (yield: 11%) and that 82% of the raw materials was decomposed into adamantyl methyl ketone.

Comparative Example 2

22.2 g (0.1 mol) of spiro[adamantan-2,2'-(5'-methyl-1',3'-dioxolan-4'-one)], 21.4 g (0.12 mol) of N-bromosuccinimide and 200 g of cyclohexane were placed in a 500 ml egg-plant type flask equipped with a reflux condenser, and while the mixture was in a slurry state, the temperature was increased to the reaction temperature, 80° C. under stirring.

When the mixture was stirred at 80° C. for about 1 hour, the reaction solution became brown. As a result of analyzing the reaction solution immediately before it became brown, it was found that the reaction solution contained spiro[adamantan-2,2'-(5'-bromo-5'-methyl-1',3'-dioxolan-4'-one)] corresponding to 2% of the raw materials and 2-adamantanone corresponding to 6% of the raw materials. When the reaction solution was further stirred for 2 hours, it became transparent. After the reaction solution was cooled in an ice bath, it was filtered to remove succinimide. As a result of analyzing the reaction solution, it was found that the reaction solution contained only 2.4 g of spiro[adamantan-2,2'-(5'-bromo-5'-methyl-1',3'-dioxolan-4'-one)] (yield: 8%) and that 85% of the raw materials was decomposed into 2-adamantanone.

Comparative Example 3

18.2 g (0.1 mol) of spiro[norbornan-2,2'-(5'-methyl-1',3'-dioxolan-4'-one)], 19.6 g (0.11 mol) of N-bromosuccinimide and 280 g of cyclohexane were placed in a 500 ml egg-plant type flask equipped with a reflux condenser, and while the mixture was in a slurry state, the temperature was increased to the reaction temperature, 80° C. under stirring.

When the mixture was stirred at 80° C. for about 1 hour, the reaction solution became brown. As a result of analyzing the reaction solution immediately before it became brown, it was found that the reaction solution contained spiro[norbornan-2,2'-(5'-bromo-5'-methyl-1',3'-dioxolan-4'-one)] corresponding to 5% of the raw materials and 2-norbornanone corresponding to 6% of the raw materials. When the reaction solution was further stirred for 2 hours, it became transparent. After the reaction solution was cooled in an ice bath, it was filtered to remove succinimide. As a result of analyzing the reaction solution, it was found that the reaction solution contained only 3.4 g of spiro[norbornan-2,2'-(5'-bromo-5'-methyl-1',3'-dioxolan-4'-one)] (yield: 13%) and that 82% of the raw materials was decomposed into 2-norbornanone.

Comparative Example 4

18.2 g (0.1 mol) of spiro[norbornan-2,2'-(5'-methyl-1',3'-dioxolan-4'-one)], 19.6 g (0.11 mol) of N-bromosuccinimide and 280 g of cyclohexane were placed in a 500 ml egg-plant type flask equipped with a reflux condenser, and while the mixture was in a slurry state, the temperature was increased to the reaction temperature, 45° C. under stirring.

When the mixture was stirred at 45° C. for about 6 hours, no change in the color of the reaction solution was observed. After the reaction solution was cooled in an ice bath, it was filtered to remove N-bromosuccinimide. As a result of analyzing the reaction solution, it was found that the reaction solution contained no spiro[norbornan-2,2'-(5'-bromo-5'-methyl-1',3'-dioxolan-4'-one)] and that most of spiro[norbornan-2,2'-(5'-methyl-1',3'-dioxolan-4'-one)] as a raw material was unreacted.

Comparative Example 5

16.5 g (0.05 mol) of 5-bromo-2,5-dimethyl-2-(1-adamantyl)-1,3-dioxolan-4-one was placed in a 500 ml egg-plant type flask, and 200 g of isopropyl ether was added thereto and dissolved therein. While cooling with a refrigerant of −10° C., 9.1 g (0.06 mol) of 1,8-diazabicyclo[5.4.0]-7-undecene diluted with 20 g of isopropyl ether was added by drops into the solution over 1 hour, followed by stirring at room temperature for 2 hours. After completion of the stirring, the reaction solution was analyzed. As a result, it was found that the reaction solution contained only 1.7 g of 5-methylene-2-(1-adamantyl)-2-methyl-1,3-dioxolan-4-one (yield: 14%) and that 80% of the raw materials was decomposed into adamantyl methyl ketone.

Comparative Example 6

15.0 g (0.05 mol) of spiro[adamantan-2,2'-(5'-bromo-5'-methyl-1',3'-dioxolan-4'-one)] was placed in a 500 ml egg-plant type flask, and 200 g of cyclohexane was added thereto and dissolved therein. While cooling in an ice bath, 6.1 g (0.06 mol) of triethylamine diluted with 20 g of cyclohexane was added by drops into the solution over 1 hour, followed by stirring at room temperature for 2 hours. After completion of the stirring, the reaction solution was analyzed. As a result, it was found that the reaction solution contained only 1.2 g of spiro[adamantan-2,2'-(5'-methylene-1',3'-dioxolan-4'-one)] (yield: 11%) and that 83% of the raw materials was decomposed into 2-adamantanone.

Comparative Example 7

13.1 g (0.05 mol) of spiro[norbornan-2,2'-(5'-bromo-5'-methyl-1',3'-dioxolan-4'-one)] was placed in a 500 ml egg-plant type flask, and 200 g of isopropyl ether was added thereto and dissolved therein. While cooling with a refrigerant of −10° C., 6.1 g (0.06 mol) of triethylamine diluted with 20 g of isopropyl ether was added by drops into the solution over 1 hour, followed by stirring at room temperature for 2 hours. After completion of the stirring, the reaction solution was analyzed. As a result, it was found that the reaction solution contained only 1.3 g of spiro[norbornan-2,2'-(5'-methylene-1',3'-dioxolan-4'-one)] (yield: 14%) and that 81% of the raw materials was decomposed into adamantanone Comparative Example 8

A mixture obtained by dissolving 16.4 g of 5-bromomethyl-2-(1-adamantyl)-2-methyl-1,3-dioxolan-4-one in 80 ml of isopropyl ether was placed in a flask equipped with an agitator, a thermometer, a condenser and a dropping funnel. While cooling in an ice bath, 9.1 g (0.06 mol) of 1,8-diazabicyclo[5.4.0]-7-undecene diluted with 20 ml of isopropyl ether was added by drops into the solution over 1 hour, followed by stirring at room temperature for 2 hours. After completion of the stirring, the reaction solution was analyzed. As a result, it was found that the reaction solution contained only 1.8 g of 5-methylene-2-(1-adamantyl)-2-methyl-1,3-dioxolan-4-one (yield: 15%) and that 81% of the raw materials was decomposed into adamantyl methyl ketone.

<Production of Polymers>

Example 5

Production of the polymer represented by the following formula (24)

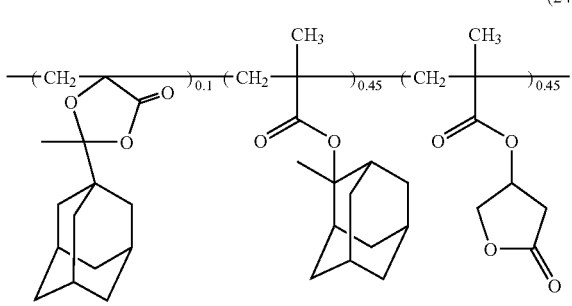

(24)

30.0 parts of ethyl lactate was placed in a separable flask equipped with a nitrogen introduction port, an agitator, a condenser and a thermometer, in a nitrogen atmosphere, and while stirring, the temperature of a hot-water bath was raised to 80° C. A monomer solution obtained by mixing 1.98 parts of AdMDO, 13.22 parts of 2-methacryloyloxy-2-methyladamantane (hereinafter referred to as MAdMA), 8.50 parts of β-methacryloyloxy-γ-butyrolactone (hereinafter referred to as HGBMA), 30.0 parts of ethyl lactate and 0.21 parts of azobisisobutyronitrile, was added by drops into the flask at a certain rate over 6 hours, and then, the temperature of 80° C. was kept for 2 hours. Thereafter, while stirring, the obtained reaction solution was added by drops into 800 parts of methanol, so as to obtain a white precipitate. The obtained precipitate was filtered, and dried under a reduced pressure at 60° C. for approximately 10 hours. Thereafter, the precipitate was dissolved in 45 parts of tetrahydrofuran, and while stirring, the obtained solution was added by drops into 800 parts of methanol. The obtained precipitate was filtered, and dried under a reduced pressure at 60° C. for approximately 40 hours.

Subsequently, the properties of the obtained copolymer were measured. According to GPC analysis, mass-average molecular weight (hereinafter referred to as Mw) was 7,200, molecular weight distribution (hereinafter referred to as Mw/Mn) was 1.45, and copolymerization ratio was AdMDO: MAdMA: HGBMA=10:45:45 according to the integration ratio of $^1$H-NMR.

Example 6

Production of the Polymer Represented by the Following Formula (25)

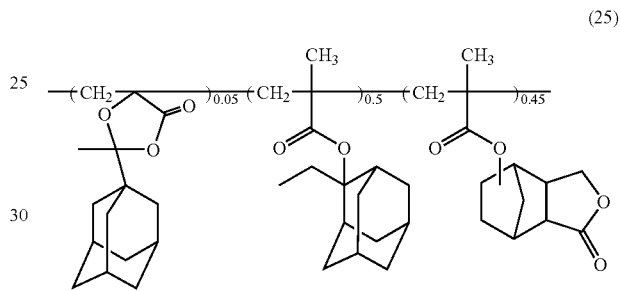

(25)

Synthesis was carried out in the same manner as in Example 5 with the exception that 1.98 parts of AdMDO was changed into 0.99 parts of the same compound, 13.22 parts of MAdMA was changed into 14.01 parts of 2-methacryloyloxy-2-ethyladamantane (hereinafter referred to as EAdMA), 8.50 parts of HGBMA was changed into 11.80 parts of a mixture consisting of 7-methacryloyloxy-3-oxatricyclo[5.2.1.0$^{2,6}$]decan-2-one and 8-methacryloyloxy-3-oxatricyclo[5.2.1.0$^{2,6}$]decan-2-one (hereinafter referred to as OTDMA), so as to obtain a copolymer.

Subsequently, the properties of the obtained copolymer were measured. According to GPC analysis, Mw was 8,000, Mw/Mn was 1.43, and copolymerization ratio was AdMDO: EAdMA: OTDMA=5:50:45 according to the integration ratio of $^1$H-NMR.

Example 7

Production of the Polymer Represented by the Following Formula (26)

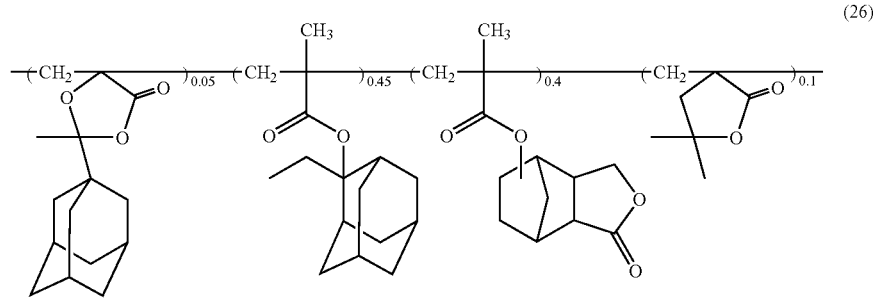

(26)

Synthesis was carried out in the same manner as in Example 5 with the exception that 0.99 parts of AdMDO, 14.01 parts of EAdMA, 11.80 parts of OTDMA and 1.26 parts of 4,4-dimethyl-2-methylene-4-butanolide (hereinafter referred to as DMMB) were copolymerized, so as to obtain a copolymer.

Subsequently, the properties of the obtained copolymer were measured. According to GPC analysis, Mw was 9,200, Mw/Mn was 1.51, and copolymerization ratio was AdMDO: EAdMA: OTDMA: DMMB=5: 45:40:10 according to the integration ratio of $^1$H-NMR.

Example 8

Production of the Polymer Represented by the Following Formula (27)

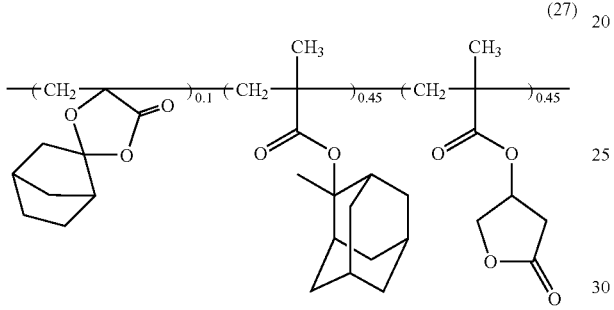

(27)

Synthesis was carried out in the same manner as in Example 5 with the exception that 1.98 parts of AdMDO was changed into 1.44 parts of NrMDO, so as to obtain a copolymer.

Subsequently, the properties of the obtained copolymer were measured. According to GPC analysis, Mw was 7,600, Mw/Mn was 1.49, and copolymerization ratio was NrMDO: MAdMA: HGBMA=10:45:45 according to the integration ratio of $^1$H-NMR.

Example 9

Production of the Polymer Represented by the Following Formula (28)

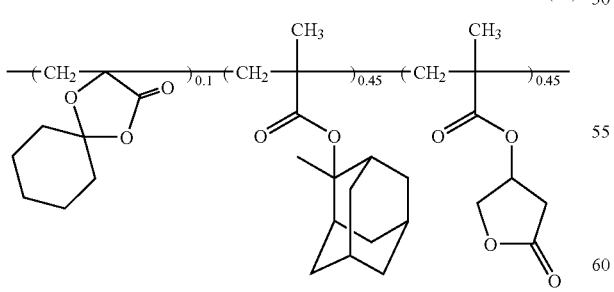

(28)

Synthesis was carried out in the same manner as in Example 5 with the exception that 1.98 parts of AdMDO was changed into 1.28 parts of spiro[cyclohexan-2'-(5'-methylene-1',3'-dioxolan-4'-one)] (hereinafter referred to as CyMDO), so as to obtain a copolymer.

Subsequently, the properties of the obtained copolymer were measured. According to GPC analysis, Mw was 8,300, Mw/Mn was 1.55, and copolymerization ratio was CyMDO: MAdMA: HGBMA=10:45:45 according to the integration ratio of $^1$H-NMR.

Comparative Example 9

Production of the Polymer Represented by the Following Formula (29)

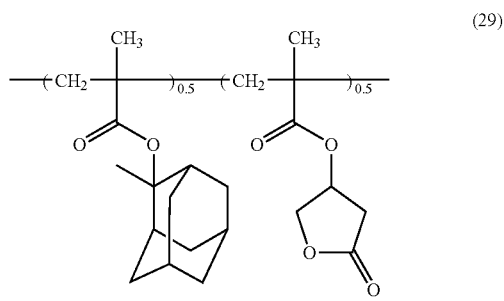

(29)

Synthesis was carried out in the same manner as in Example 5 with the exception that 13.22 parts of MAdMA and 8.50 parts of HGBMA were copolymerized, so as to obtain a copolymer.

Subsequently, the properties of the obtained copolymer were measured. According to GPC analysis, Mw was 7,400, Mw/Mn was 1.35, and copolymerization ratio was MAdMA: HGBMA=50:50 according to the integration ratio of $^1$H-NMR.

Comparative Example 10

Production of the Polymer Represented by the Following Formula (30)

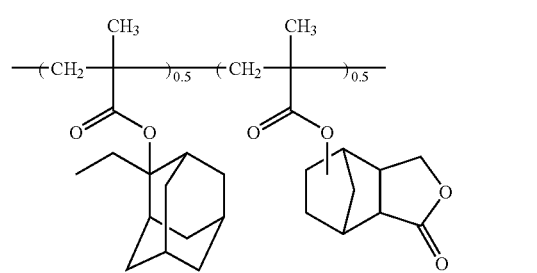

(30)

Synthesis was carried out in the same manner as in Example 5 with the exception that 14.01 parts of EAdMA and 11.80 parts of HGBMA were copolymerized, so as to obtain a copolymer.

Subsequently, the properties of the obtained copolymer were measured. According to GPC analysis, Mw was 9,600, Mw/Mn was 1.41, and copolymerization ratio was EAdMA: OTDMA=50:50 according to the integration ratio of $^1$H-NMR.

Comparative Example 11

Production of the Polymer Represented by the Following Formula (31)

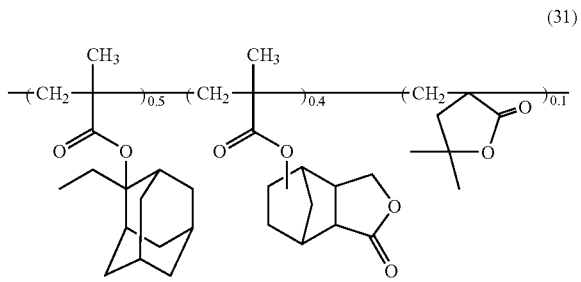

(31)

Synthesis was carried out in the same manner as in Example 5 with the exception that 14.01 parts of EAdMA, 11.80 parts of OTDMA and 1.26 parts of DMMB were copolymerized, so as to obtain a copolymer.

Subsequently, the properties of the obtained copolymer were measured. According to GPC analysis, Mw was 10,500, Mw/Mn was 1.45, and copolymerization ratio was EAdMA: OTDMA: DMMB=50:40:10 according to the integration ratio of $^1$H-NMR.

With regard to the polymers obtained in Examples 5 to 8 and Comparative examples 9 to 11, the solubility in a resist solvent, and the sensitivity, the resolution, the dry etching resistance (etching rate) and the line edge roughness of the obtained resist patterns were measured and evaluated as follows. The results are shown in Table 1.

<Solubility in a Resist Solvent>

Each copolymer was dissolved in a certain amount of resist solvent (propylene glycol monomethyl ether acetate) at room temperature while stirring, so that the solid content became 20% by mass, and the time required for the copolymer to be completely dissolved was measured. The results are shown in Table 1.

Symbols in the table mean as follows:

⊚: The time required for the copolymer to be completely dissolved is less than 1 hour;

○: The time required for the copolymer to be completely dissolved is 1 hour or more, and less than 6 hours;

Δ: The time required for the copolymer to be completely dissolved is 6 hours or more, and less than 24 hours;

x: The time required for the copolymer to be completely dissolved is 24 hours or more, or the copolymer is insoluble.

<Formation of a Resist Pattern>

100 parts of each of the copolymers obtained in Examples 5 to 8 and Comparative examples 9 to 11, and 2 parts of triphenylsulfonium triflate were dissolved in 500 parts of propylene glycol monomethyl ether acetate, so as to obtain a homogeneous solution. Thereafter, the solution was filtered with a fluorocarbon resin filter, so as to prepare a resist composition solution. And then, each of the prepared composition solutions was spin-coated on a 3-inch silicon wafer, and using a hot plate, pre-bake was carried out at 120° C. for 60 seconds to form a thin film having a film thickness of 0.5 μm. Subsequently, the thin film was exposed using a light exposure system with a wavelength of 193 nm (SP193 manufactured by Nikon Corporation), and then, using a hot plate, baking was carried out at 120° C. for 60 seconds. Thereafter, development was carried out at room temperature using a 2.38% by mass tetramethylammonium hydroxide aqueous solution, followed by washing with pure water and drying, so as to form a resist pattern.

The sensitivity, the resolution, the dry etching resistance (etching rate) and the line edge roughness of each of the obtained resist patterns were measured and evaluated as follows. The results are shown in Table 1.

<Sensitivity>

Sensitivity was defined as a light exposure (mJ/cm$^2$), which forms a line-and-space pattern (line/space=1/1) at a line width of 1/1.

<Resolution>

Resolution was defined as the minimal dimension (μm) of a resist pattern, which was resolved when exposure was carried out at the above-described light exposure.

<Etching Rate>

The resist film formed on a silicon wafer was subjected to a dry etching treatment using an etching machine manufactured by Tokyo Electron Ltd. The dry etching treatment was carried out using $C_4F_8/Ar/O_2$ mixed gas, under etching conditions at 2,000 W, at 50 mTorr, for 50 seconds. The film thickness of the resist film was measured before and after the dry etching treatment, using a Lambda Ace VM-8000J light-interference type thickness measurement system manufactured by Dainippon Screen MFG Co., Ltd. Etching rate of the resist was defined as the reduced amount of the film thickness per unit time. Moreover, the etching rate was normalized by setting the etching rate of a novolac resin as 1.

<Line Edge Roughness>

The minimum line width of the line of the formed line-and-space pattern (line/space=1/1) was subtracted from the maximum line width thereof, and the obtained value was divided by the half-value width of the maximum line width of the line. The thus obtained value was defined as line edge roughness.

TABLE 1

| | Sensitivity (mJ/cm$^2$) | Resolution (μm) | Etching rate | Line edge roughness | Solubility in resist solvent |
|---|---|---|---|---|---|
| Polymer of Example 5 | 5.0 | 0.18 | 1.03 | 0.05 | ⊚ |
| Polymer of Example 6 | 4.9 | 0.17 | 1.02 | 0.07 | ○ |
| Polymer of Example 7 | 4.9 | 0.17 | 1.03 | 0.07 | ○ |
| Polymer of Example 8 | 5.0 | 0.18 | 1.04 | 0.10 | ○ |
| Polymer of Example 9 | 5.0 | 0.18 | 1.06 | 0.10 | ⊚ |
| Polymer of Comparative example 9 | 5.0 | 0.18 | 1.05 | 0.14 | Δ |
| Polymer of Comparative example 10 | 4.9 | 0.19 | 1.03 | 0.13 | X |
| Polymer of Comparative example 11 | 4.9 | 0.18 | 1.05 | 0.13 | X |

The polymers of the present invention (Examples 5 to 8) were more excellent in solubility in a resist solvent than the polymers of Comparative examples 9 to 11. Moreover, the chemically amplified resist compositions comprising the polymers of the present invention (Examples 5 to 8) had sufficient sensitivity, resolution and etching resistance, and at the same time, the chemically amplified resist compositions had less line edge roughness than that of the chemically amplified resist compositions comprising the polymers of Comparative examples 9 to 11.

Example 10

Synthesis of the Polymer P-1 Represented by the Following Formula (32)

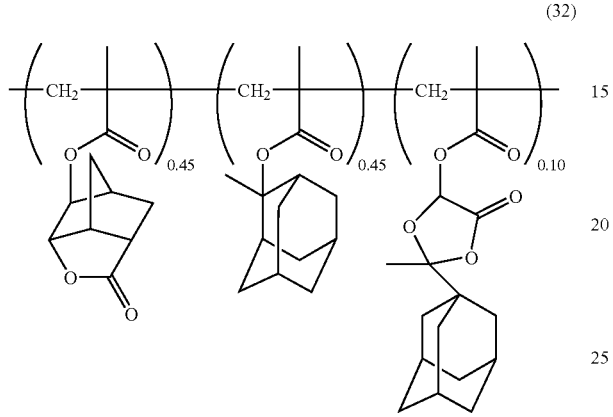

(32)

15.8 parts of propylene glycol monomethyl ethyl acetate (hereinafter referred to as PGMEA) and 4.0 parts of γ-butyrolactone (hereinafter referred to as γBL) were placed in a separable flask equipped with a nitrogen introduction port, an agitator, a condenser and a thermometer, in a nitrogen atmosphere, and while stirring, the temperature of a hot-water bath was raised to 80° C. A monomer solution obtained by mixing 10.0 parts of 2-exo-methacryloyloxy-4-oxatricyclo[4.2.1.0$^{3,7}$]nonan-5-one (hereinafter referred to as OTNMA), 10.5 parts of 2-methacryloyloxy-2-methyladamantane (hereinafter referred to as MAdMA), 3.2 parts of 5-methacryloyloxy-2-methyl-2-(1-adamantyl)-1,3-dioxolan-4-one (hereinafter referred to as M-1 monomer), 35.6 parts of PGMEA and 0.82 parts of azobisisobutyronitrile, was added by drops into the flask at a certain rate over 7 hours, and then, the temperature of 80° C. was kept for 2 hours. Thereafter, while stirring, the obtained reaction solution was added by drops into 800 parts of methanol, so as to obtain a white precipitate (polymer P-1). The obtained precipitate was filtered, and dried under a reduced pressure at 60° C. for approximately 10 hours. Thereafter, the dried precipitate was dissolved in 45 parts of tetrahydrofuran, and while stirring, the obtained solution was added by drops into 800 parts of methanol. The obtained precipitate was filtered, and dried under a reduced pressure at 60° C. for approximately 40 hours.

The properties of the obtained polymer were measured, and the results are shown in Table 2.

Example 11

Synthesis of the Polymers P-2 to P-7

The polymers P-2 to P-7 having the compositions as shown in Table 2 were synthesized in the same manner as in Example 10 (synthesis of the polymer P-1).

The properties of the obtained polymers P-2 to P-7 were measured, and the results are shown in Table 2.

Comparative Example 12

Synthesis of the Polymers P-8 and P-9

The polymers P-8 and P-9 having the compositions as shown in Table 2 were synthesized in the same manner as in Example 10 (synthesis of the polymer P-1).

The properties of the obtained polymers P-8 and P-9 were measured, and the results are shown in Table 2.

The names and the structural formulas of the raw material monomers used in Example 11 and Comparative example 12 are as follows:

OTNMA: 2-exo-methacryloyloxy-4-oxatricyclo [4.2.1.0$^{3,7}$]nonan-5-one

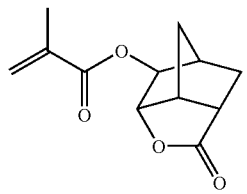

OTNA: 2-exo-acryloyloxy-4-oxatricyclo[4.2.1.0$^{3,7}$] nonan-5-one

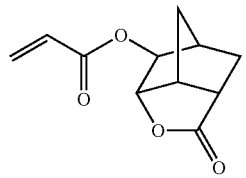

OTDMA: 8- or 9-methacryloyloxy-4-oxatricyclo [5.2.1.0$^{2,6}$]decan-3-one

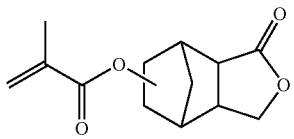

OTDA: 8- or 9-acryloyloxy-4-oxatricyclo[5.2.1.0$^{2,6}$]decan-3-one

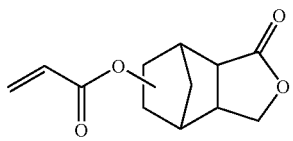

MAdMA: 2-methacryloyloxy-2-methyladamantane

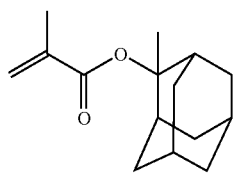

MAdA: 2-acryloyloxy-2-methyladamantane

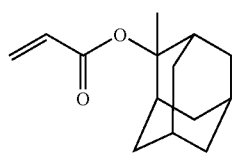

EAdMA: 2-methacryloyloxy-2-ethyladamantane

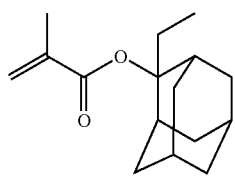

EAdA: 2-acryloyloxy-2-ethyladamantane

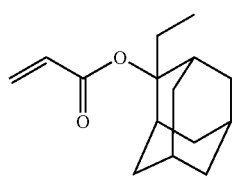

HAdMA: 1-methacryloyloxy-3-hydroxyadamantane

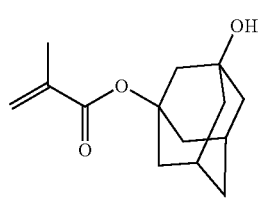

HAdA: 1-acryloyloxy-3-hydroxyadamantane

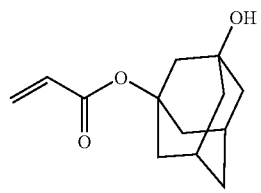

DMMB: 4,4-dimethyl-2-methylene-4-butanolide

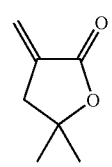

M-1: 5-methacryloyloxy-2-methyl-2-(1-adamantyl)-1,3-dioxolan-4-one

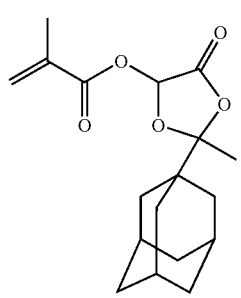

M-2: spiro[adamantane-2,2'-(4'-methacryloyloxypropyleneglycol-1,3'-dioxolane)

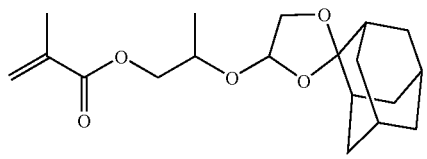

M-3: spiro[adamantane-2,2'-(4'-acryloyloxymethyl-1',3'-dioxolane)

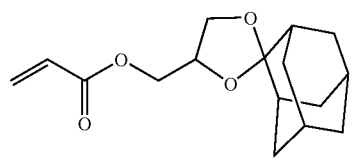

M4: spiro[norbornan-2,2'-(4'-acryloyloxymethyl-1',3'-dioxolan-5-one)

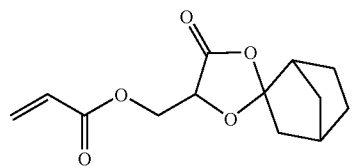

M-5:
2-methyl-2-ethyl-4-methacryloyl-1,3-dioxolan-5-one

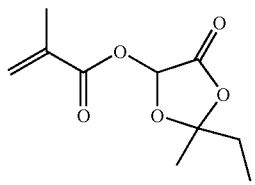

M-6:
4-acryloyloxymethyl-2-cyclohexyl-1,3-dioxolane

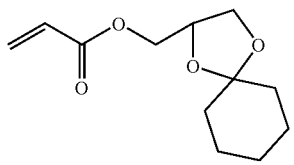

With regard to the polymers P-1 to P-9, the solubility in a resist solvent, and the sensitivity, the dry etching resistance (etching rate) and the line edge roughness of the obtained resist patterns were measured and evaluated as follows. The results are shown in Table 2.

<Solubility in a Resist Solvent>

Each copolymer was dissolved in a certain amount of resist solvent (propylene glycol monomethyl ether acetate or ethyl lactate) at room temperature while stirring, so that the solid content became 20% by mass, and the time required for the copolymer to be completely dissolved was measured. The results are shown in Table 2.

Symbols in the table mean as follows:

⊚: The time required for the copolymer to be completely dissolved is less than 1 hour;

○: The time required for the copolymer to be completely dissolved is 1 hour or more, and less than 6 hours;

Δ: The time required for the copolymer to be completely dissolved is 6 hours or more, and less than 24 hours;

x: The time required for the copolymer to be completely dissolved is 24 hours or more, or the copolymer is insoluble.

<Formation of a Resist Pattern>

100 parts of each of the copolymers P-1 to P-9, and 2 parts of triphenylsulfonium triflate were dissolved in a mixed solution of 630 parts of propylene glycol monomethyl ether acetate and 70 parts of γ-butyrolactone, so as to obtain a homogeneous solution. Thereafter, the solution was filtered with a fluorocarbon resin filter, so as to prepare a resist composition solution. And then, each of the prepared composition solutions was spin-coated on a 3-inch silicon wafer, and using a hot plate, pre-bake was carried out at 120° C. for 60 seconds to form a thin film having a film thickness of 0.4 μm. Subsequently, the thin film was exposed using a light exposure system with a wavelength of 193 nm (SP193 manufactured by Nikon Corporation), and then, using a hot plate, baking was carried out at 120° C. for 60 seconds. Thereafter, development was carried out at room temperature for 60 seconds using a 2.38% by mass tetramethylammonium hydroxide aqueous solution, followed by washing with pure water and drying, so as to form a resist pattern.

The sensitivity, the dry etching resistance (etching rate) and the line edge roughness of each of the obtained resist patterns were measured and evaluated as follows. The results are shown in Table 2.

<Sensitivity>

Sensitivity was defined as a light exposure (mJ/cm$^2$), which forms a line-and-space pattern (line/space=1/1) at a line width of 1/1.

<Etching Rate>

The resist film formed on a silicon wafer was subjected to a dry etching treatment using a SPE-220T dry etching machine manufactured by Showa Shinku Co., Ltd. The dry etching treatment was carried out using $CF_4/O_2$ mixed gas, for 2 minutes. The film thickness of the resist film was measured before and after the dry etching treatment, using a Lambda Ace VM-8000J light-interference type thickness measurement system manufactured by Dainippon Screen MFG Co., Ltd. Etching rate of the resist was defined as the reduced amount of the film thickness per unit time. Moreover, the etching rate was normalized by setting the etching rate of a novolac resin as 1.

<Line Edge Roughness>

The minimum line width of the line of the formed line-and-space pattern (line/space=1/1) was subtracted from the maximum line width thereof, and the obtained value was divided by the half-value width of the maximum line width of the line. The thus obtained value was defined as line edge roughness.

TABLE 2

| | | Examples 10 and 11 | | | | | | | Comparative example 12 | |
|---|---|---|---|---|---|---|---|---|---|---|
| Polymer | | P-1 | P-2 | P-3 | P-4 | P-5 | P-6 | P-7 | P-8 | P-9 |
| Mass-average molecular weight (Mw) | | 11,000 | 12,500 | 12,000 | 14,500 | 16,000 | 13,500 | 14,500 | 11,500 | 15,500 |
| Molecular weight distribution (Mw/Mn) | | 1.69 | 1.72 | 1.85 | 1.85 | 1.82 | 1.78 | 1.81 | 1.79 | 1.89 |
| Copolymerization composition ratio (mol %) | OTNMA | 45 | | 40 | | | | | 50 | |
| | OTNA | | | | | 35 | | | | 40 |
| | OTDMA | | 45 | | | | 40 | | | |
| | OTDA | | | | 40 | | | 45 | | |
| | MAdMA | 45 | | | | | | | 50 | |
| | MAdA | | | | 40 | | | | | |
| | EAdMA | | 45 | 40 | | | 40 | | | |
| | EAdA | | | | | 40 | | 40 | | 40 |
| | HAdMA | | | 10 | | | 10 | | | |
| | HAdA | | | | 10 | 15 | | 5 | | 20 |
| | M-1 | 10 | | | | | | | | |
| | M-2 | | | | 10 | | | | | |
| | M-3 | | 10 | | | | | | | |

TABLE 2-continued

| Polymer | | Examples 10 and 11 | | | | | | | Comparative example 12 | |
|---|---|---|---|---|---|---|---|---|---|---|
| | | P-1 | P-2 | P-3 | P-4 | P-5 | P-6 | P-7 | P-8 | P-9 |
| | M-4 | | | 10 | | 10 | | | | |
| | M-5 | | | | | | 10 | | | |
| | M-6 | | | | | | | 10 | | |
| Sensitivity (mJ/cm$^2$) | | 4.2 | 3.7 | 3.6 | 7.5 | 6.7 | 3.9 | 7.0 | 4.1 | 6.6 |
| Etching rate | | 1.02 | 1.01 | 1.04 | 1.04 | 1.03 | 1.06 | 1.07 | 0.99 | 1.01 |
| Solubility | PGMEA | ○ | ○ | ⊚ | ○ | ○ | ⊚ | ○ | X | X |
| | Ethyl lactate | ⊚ | ○ | ⊚ | ⊚ | ⊚ | ⊚ | ⊚ | Δ | Δ |
| Line edge roughness | | 0.04 | 0.06 | 0.05 | 0.05 | 0.06 | 0.05 | 0.06 | 0.16 | 0.23 |

The polymers P-1 to P-7 of Examples 10 and 11, which were the polymers of the present invention, were more excellent in solubility in a resist solvent than the polymers P-8 and P-9 of Comparative example 12. Moreover, the chemically amplified resist compositions of the present invention comprising the polymers P-1 to P-7 had sufficient sensitivity and etching resistance, and at the same time, the chemically amplified resist compositions had less line edge roughness than that of the chemically amplified resist compositions comprising the polymers P-8 and P-9.

INDUSTRIAL APPLICABILITY

The 5-methylene-1,3-dioxolan-4-one derivative of the present invention, which has, at position 2, a bridged cyclic hydrocarbon group or an alkyl group having a bridged cyclic hydrocarbon group as a substituent, has polymerization properties that are suitable for copolymerization with other monomers, and the obtained homopolymer and copolymer are excellent in light transparency and heat stability. Moreover, according to the production method of the present invention, the 5-methylene-1,3-dioxolan-4-one derivative can be easily produced at a high yield and a high purity.

The polymer of the present invention is excellent both in solubility in an organic solvent (resist solvent) and in heat resistance, and thus, it is preferable as a resist composition resin. The resist composition of the present invention comprising this polymer has sufficient sensitivity, resolution and dry etching resistance, and also has little line edge roughness. The resist composition of the present invention is preferably used in deep ultraviolet excimer laser lithography and electron beam lithography, and particularly in lithography using an ArF excimer laser.

According to the pattern formation method of the present invention using the resist composition, a high-precision fine resist pattern can be stably formed.

The invention claimed is:

1. A 5-methylene-1,3-dioxolan-4-one derivative represented by the following formula (1):

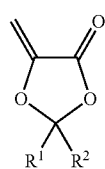

(1)

wherein R$^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R$^2$ represents a hydrogen atom, or a linear or branched alkyl group containing 1 to 6 carbon atoms; or R$^1$ and R$^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

2. A 5-halo-5-methyl-1,3-dioxolan-4-one derivative represented by the following formula (2):

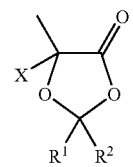

(2)

wherein X represents a chlorine atom or a bromine atom; R$^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R$^2$ represents a hydrogen atom, or a linear or branched alkyl group containing 1 to 6 carbon atoms; or R$^1$ and R$^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

3. A method of producing a 5-halo-5-methyl-1,3-dioxolan-4-one derivative represented by the following formula (2):

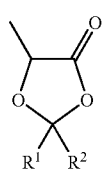

(2)

wherein X represents a chlorine atom or a bromine atom; R¹ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R² represents a hydrogen atom, or a linear or branched alkyl group containing 1 to 6 carbon atoms; or R¹ and R² represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, which comprises the step of:

reacting a 5-methyl-1,3-dioxolan-4-one derivative represented by the following formula (3) with a halogenating agent at a reaction temperature within a range of 50° C. to 65° C.:

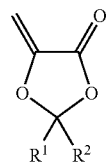

(3)

wherein R¹ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R² represents a hydrogen atom, or a linear or branched alkyl group containing 1 to 6 carbon atoms; or R¹ and R² represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

4. A method of producing a 5-methylene-1,3-dioxolan-4-one derivative represented by the following formula (1):

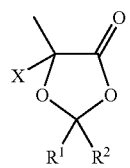

(1)

wherein R¹ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R² represents a hydrogen atom, or a linear or branched alkyl group containing 1 to 6 carbon atoms; or R¹ and R² represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, which comprises the step of:

reacting the 5-halo-5-methyl-1,3-dioxolan-4-one derivative represented by the below formula (2) with an amide compound represented by the following formula (5) to carry out a dehydrohalogenation reaction:

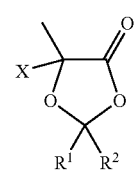

(2)

wherein X represents a chlorine atom or a bromine atom; R¹ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R² represents a hydrogen atom, or a linear or branched alkyl group containing 1 to 6 carbon atoms; or R¹ and R² represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms,

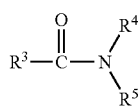

wherein each of $R^3$, $R^4$ and $R^5$ independently represents a hydrogen atom, or a linear or branched alkyl group containing 1 to 4 carbon atoms.

5. A method of producing a 5-methylene-1,3-dioxolan-4-one derivative represented by the following formula (1):

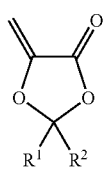

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms, which comprises the step of:

reacting a 5-halomethyl-1,3-dioxolan-4-one derivative represented by the following formula (4) with an amide compound represented by the following formula (5) to carry out a dehydrohalogenation reaction:

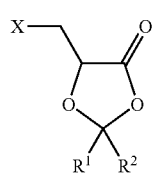

wherein X represents a chlorine atom or a bromine atom; $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms; and

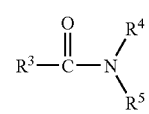

wherein each of $R^3$, $R^4$ and $R^5$ independently represents a hydrogen atom, or a linear or branched alkyl group containing 1 to 4 carbon atoms.

6. A polymer obtained by (co)polymerizing a monomer composition comprising a monomer represented by the following formula (1):

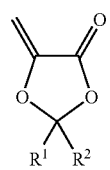

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

7. A polymer comprising at least one of constitutional units represented by the following formula (6):

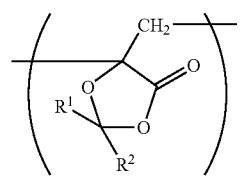

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; R² represents a hydrogen atom, or a linear or branched alkyl group containing 1 to 6 carbon atoms; or R¹ and R² represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

8. A polymer comprising at least one of constitutional units represented by the following formula (7) and at least one of constitutional units represented by the following formula (81), (91) or (10):

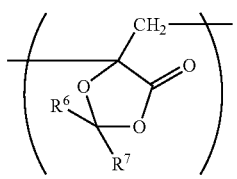

(7)

wherein each of R⁶ and R⁷ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or R⁶ and R⁷ represent a cyclic hydrocarbon group containing 4 to 16 carbon atoms together with the carbon atom to which they are bound, provided that the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms;

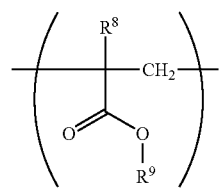

(81)

wherein R⁸ represents a hydrogen atom or a methyl group, and R⁹ represents a branched alkyl group containing 3 to 6 carbon atoms, a cyclic hydrocarbon group containing 4 to 8 carbon atoms, or a bridged cyclic hydrocarbon group containing 4 to 16 carbon atoms, provided that the alkyl group, the cyclic hydrocarbon group and the bridged cyclic hydrocarbon group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms;

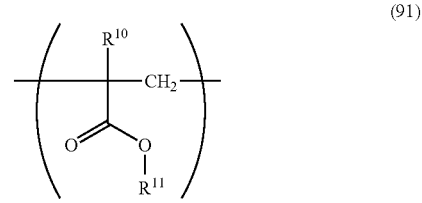

(91)

wherein R¹⁰ represents a hydrogen atom or a methyl group, and R¹¹ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group, wherein said hydrophilic functional group is selected from the group consisting of hydroxyl, carboxy, amino, ketone, acid anhydride, ester, ether, lactone, imino and amide groups; provided that the alkyl group, the cyclic hydrocarbon group, the bridged cyclic hydrocarbon group and the hydrophilic functional group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms; and

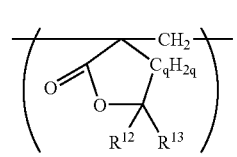

(10)

wherein each of R¹² and R¹³ independently represents a hydrogen atom, a methyl group or an ethyl group, and q represents an integer of 1 to 4.

9. The polymer according to claim 8, comprising reacted units of the monomer unit (91) having a hydroxyl hydrophilic functional group.

10. The polymer according to claim 8, comprising reacted units of the monomer unit (91) having a carboxy hydrophilic functional group.

11. The polymer according to claim 8, comprising reacted units of the monomer unit (91) having an amino hydrophilic functional group.

12. The polymer according to claim 8, comprising reacted units of the monomer unit (91) having a ketone hydrophilic functional group.

13. The polymer according to claim 8, comprising reacted units of the monomer unit (91) having an acid anhydride functional group.

14. The polymer according to claim 8, comprising reacted units of the monomer unit (91) having a lactone hydrophilic functional group.

15. The polymer according to claim 8, comprising reacted units of the monomer unit (91) having an imino hydrophilic functional group.

16. The polymer according to claim 8, comprising reacted units of the monomer unit (91) having an imide hydrophilic functional group.

17. The polymer according to claim 8, comprising reacted units of the monomer unit (91) having an ester hydrophilic functional group.

18. A polymer comprising at least one constitutional units represented by the following formula (6) and at least one constitutional units represented by the following formula (8), (9) or (10):

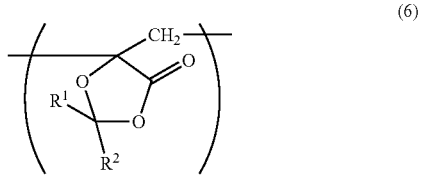
(6)

wherein $R^1$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent; $R^2$ represents a hydrogen atom, or a linear or branched alkyl group containing 1 to 6 carbon atoms; or $R^1$ and $R^2$ represent a bridged cyclic hydrocarbon group containing 4 to 16 carbon atoms together with the carbon atom to which they are bound, provided that the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms;

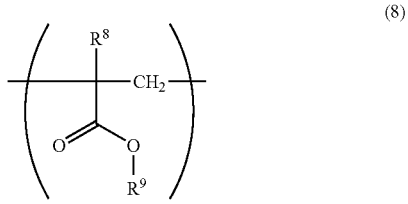
(8)

wherein $R^8$ represents a hydrogen atom or a methyl group, and $R^9$ represents a linear or branched alkyl group containing 1 to 6 carbon atoms, a cyclic hydrocarbon group containing 4 to 8 carbon atoms, or a bridged cyclic hydrocarbon group containing 4 to 16 carbon atoms, provided that the alkyl group, the cyclic hydrocarbon group and the bridged cyclic hydrocarbon group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms;

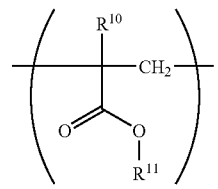
(9)

wherein $R^{10}$ represents a hydrogen atom or a methyl group, and $R^{11}$ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group, provided that the alkyl group, the cyclic hydrocarbon group, the bridged cyclic hydrocarbon group and the hydrophilic functional group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms; and

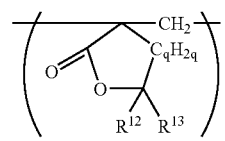
(10)

wherein each of $R^{12}$ and $R^{13}$ independently represents a hydrogen atom, a methyl group or an ethyl group, and q represents an integer of 1 to 4.

19. A polymer comprising at least one of constitutional units represented by the following formula (11):

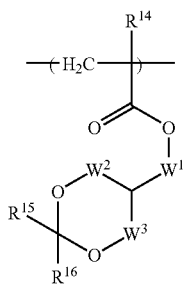
(11)

wherein $W^1$ represents a direct bond or a methylene chain containing 1 to 6 carbon atoms [—$(CH_2)_k$— (wherein k represents an integer of 0 to 6)], $W^2$ represents a direct bond or a methylene chain containing 1 to 3 carbon atoms [—$(CH_2)_l$— (wherein l represents an integer of 0 to 3)], $W^3$ represents a methylene chain containing 1 to 3 carbon atoms [—$(CH_2)_m$— (wherein m represents an integer of 1 to 3)], $R^{14}$ represents a hydrogen atom or a methyl group, $R^{15}$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent, $R^{16}$ represents a hydrogen atom, or a linear or branched alkyl group containing 1 to 6 carbon atoms; or $R^{15}$ and $R^{16}$ represent a bridged cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, the methylene chain containing 1 to 3 carbon atoms may have a carbonyl group therein, and the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

20. A polymer comprising at least one of constitutional units represented by the following formula (12):

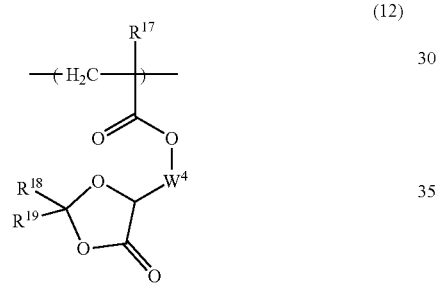

(12)

wherein $W^4$ represents a direct bond or a methylene chain containing 1 to 6 carbon atoms [—$(CH_2)_n$— (wherein n represents an integer of 0 to 6)], $R^{17}$ represents a hydrogen atom or a methyl group, each of $R^{18}$ and $R^{19}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{18}$ and $R^{19}$ represent a cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, and the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms.

21. A polymer comprising at least one of constitutional units represented by the following formula (13), and at least one of constitutional units selected from a constitutional unit derived from a monomer of 2-(meth)acryloyloxy-2-methyladamantane, 2-(meth)acryloyloxy-2-ethyladamantane, or derivatives having an alkyl group on the cyclic hydrocarbon group of these monomers or a constitutional units represented by the following formula (10):

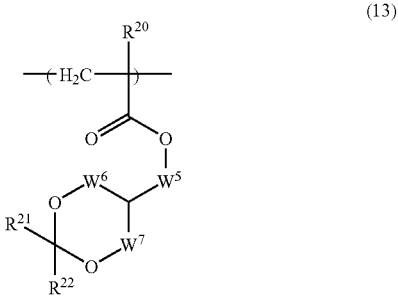

(13)

wherein $W^5$ represents a direct bond or a methylene chain containing 1 to 6 carbon atoms [—$(CH_2)_x$— (wherein x represents an integer of 0 to 6)], $W^6$ represents a direct bond or a methylene chain containing 1 to 3 carbon atoms [—$(CH_2)_y$— (wherein y represents an integer of 0 to 3)], $W^7$ represents a methylene chain containing 1 to 3 carbon atoms [—$(CH_2)_n$— (wherein z represents an integer of 1 to 3)], $R^{20}$ represents a hydrogen atom or a methyl group, each of $R^{21}$ and $R^{22}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{21}$ and $R^{22}$ represent a cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, the methylene chain containing 1 to 3 carbon atoms may have a carbonyl group therein, and the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms; and

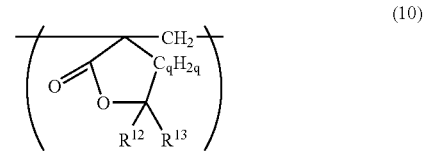

(10)

wherein each $R^{12}$ and $R^{13}$ independently represents a hydrogen atom, a methyl group or an ethyl group, and q represents an integer of 1 to 4.

22. A polymer comprising at least one constitutional units represented by the following formula (11) or (12) and at least one of constitutional units represented by the formula (8), (9) or (10):

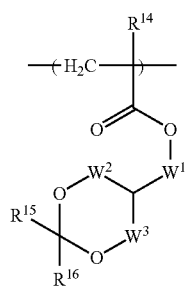

(11)

wherein $W^1$ represents a direct bond or a methylene chain containing 1 to 6 carbon atoms [—$(CH_2)_k$— (wherein k represents an integer of 0 to 6)], $W^2$ represents a direct bond or a methylene chain containing 1 to 3 carbon atoms [—$(CH_2)_l$— (wherein l represents an integer of 0 to 3)], $W^3$ represents a methylene chain containing 1 to 3 carbon atoms [—$(CH_2)_m$— (wherein m represents an integer of 1 to 3)], $R^{14}$ represents a hydrogen atom or a methyl group, $R^{15}$ represents a bridged cyclic hydrocarbon group containing 4 to 16 carbon atoms, or a linear or branched alkyl group containing 1 to 6 carbon atoms which has a bridged cyclic hydrocarbon group containing 4 to 16 carbon atoms as a substituent, $R^{16}$ represents a hydrogen atom, or a linear or branched alkyl group containing 1 to 6 carbon atoms; or $R^{15}$ and $R^{16}$ represent a bridged cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, the methylene chain containing 1 to 3 carbon atoms may have a carbonyl group therein, and the alkyl group and the bridged cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms;

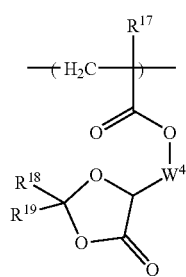

(12)

wherein $W^4$ represents a direct bond or a methylene chain containing 1 to 6 carbon atoms [—$(CH_2)_n$— (wherein n represents an integer of 0 to 6)], $R^{17}$ represents a hydrogen atom or a methyl group, each of $R^{18}$ and $R^{19}$ independently represents a hydrogen atom, a linear or branched alkyl group containing 1 to 6 carbon atoms, a cyclic hydrocarbon group containing 4 to 16 carbon atoms, or a linear or branched alkyl group containing 1 to 6 carbon atoms which has a cyclic hydrocarbon group containing 4 to 16 carbon atoms as a substituent; or $R^{18}$ and $R^{19}$ represent a cyclic hydrocarbon group containing 4 to 16 carbon atoms together with the carbon atom to which they are bound, provided that the methylene chain containing 1 to 6 carbon atoms may be optionally substituted by an optionally substituted alkyl group containing 1 to 3 carbon atoms, and may optionally have at least one ether bond therein, and the alkyl group and the cyclic hydrocarbon group may have at least one substituent selected from a group consisting of a linear or branched alkyl group containing 1 to 6 carbon atoms which may be optionally substituted, a hydroxy group, a carboxy group, an acyl group containing 2 to 6 carbon atoms, an alkoxy group containing 1 to 6 carbon atoms, and a carboxy group esterified with an alcohol containing 1 to 6 carbon atoms;

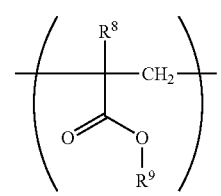

(8)

wherein $R^8$ represents a hydrogen atom or a methyl group, and $R^9$ represents a linear or branched alkyl group containing 1 to 6 carbon atoms, a cyclic hydrocarbon group containing 4 to 8 carbon atoms, or a bridged cyclic hydrocarbon group containing 4 to 16 carbon atoms, provided that the alkyl group, the cyclic hydrocarbon group and the bridged cyclic hydrocarbon group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms;

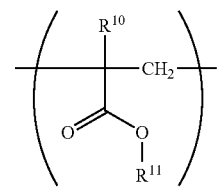

(9)

wherein $R^{10}$ represents a hydrogen atom or a methyl group, and $R^{11}$ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group, provided that the alkyl group, the cyclic hydrocarbon group, the bridged cyclic hydrocarbon group and the hydrophilic functional group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms; and

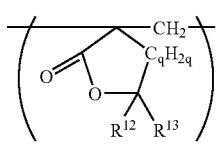

(10)

wherein each of $R^{12}$ and $R^{13}$ independently represents a hydrogen atom, a methyl group or an ethyl group, and q represents an integer of 1 to 4.

23. The polymer according to any one of claims 6 to 22, wherein its mass-average molecular weight is within a range of 1,000 to 100,000.

24. A polymer mixture comprising at least one polymer according to any one of claims 6 to 22, and at least one polymer comprising at least one of constitutional units represented by formula (8), (9) or (10):

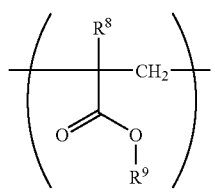

(8)

wherein $R^8$ represents a hydrogen atom or a methyl group, and $R^9$ represents a linear or branched alkyl group containing 1 to 6 carbon atoms, a cyclic hydrocarbon group containing 4 to 8 carbon atoms, or a bridged cyclic hydrocarbon group containing 4 to 16 carbon atoms, provided that the alkyl group, the cyclic hydrocarbon group and the bridged cyclic hydrocarbon group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms;

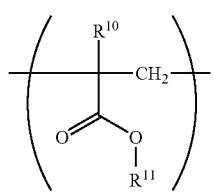

(9)

wherein $R^{10}$ represents a hydrogen atom or a methyl group, and $R^{11}$ represents a hydrogen atom, a hydrophilic functional group, a linear or branched alkyl group containing 1 to 6 carbon atoms which has a hydrophilic functional group, a cyclic hydrocarbon group containing 4 to 8 carbon atoms which has a hydrophilic functional group, or a bridged cyclic hydrocarbon group containing 4 to 16 carbon atoms which has a hydrophilic functional group, provided that the alkyl group, the cyclic hydrocarbon group, the bridged cyclic hydrocarbon group and the hydrophilic functional group may have at least one substituent selected from a group consisting of a linear or branched alkyl group containing 1 to 6 carbon atoms which may be optionally substituted, a hydroxy group, a carboxy group, and a carboxy group esterified with an alcohol containing 1 to 6 carbon atoms; and

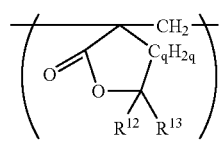

(10)

wherein each of $R^{12}$ and $R^{13}$ independently represents a hydrogen atom, a methyl group or an ethyl group, and q represents an integer of 1 to 4.

25. A resist composition, which comprises the polymer mixture according to claim 24.

26. A method of forming a pattern, which comprises the steps of:
coating the resist composition according to claim 25 onto a substrate to be processed;
exposing the substrate to a light with a wavelength of 250 nm or shorter or an electron beam; and
development.

27. The method of forming a pattern according to claim 26, wherein the light used for exposure is an ArF excimer laser.

28. A method of forming a pattern, which comprises the steps of:
coating the resist composition according to 25 onto a substrate to be processed;
exposing the substrate to a light with a wavelength of 250 nm or shorter or an electron beam; and
developing it with a developing solution after subjecting it to a heat treatment, if necessary.

29. The method of forming a pattern according to claim 28, wherein the light used for exposure is an ArF excimer laser.

30. A resist composition, which comprises the polymer mixture according to claim 24 and a photoacid generator.

31. A method of forming a pattern, which comprises the steps of:
coating the resist composition according to claim 30 onto a substrate to be processed;
exposing the substrate to a light with a wavelength of 250 nm or shorter or an electron beam; and
development.

32. The method of forming a pattern according to claim 31, wherein the light used for exposure is an ArF excimer laser.

33. A method of forming a pattern, which comprises the steps of:

coating the resist composition according to 30 onto a substrate to be processed;

exposing the substrate to a light with a wavelength of 250 nm or shorter or an electron beam; and developing it with a developing solution after subjecting it to a heat treatment, if necessary.

34. The method of forming a pattern according to claim 33, wherein the light used for exposure is an ArF excimer laser.

35. A resist composition, which comprises at least one polymer according to any one of claims 6 to 22.

36. A method of forming a pattern, which comprises the steps of:

coating the resist composition according to claim 35 onto a substrate to be processed;

exposing the substrate to a light with a wavelength of 250 nm or shorter or an electron beam; and development.

37. The method of forming a pattern according to claim 36, wherein the light used for exposure is an ArF excimer laser.

38. A method of forming a pattern, which comprises the steps of:

coating the resist composition according to 35 onto a substrate to be processed;

exposing the substrate to a light with a wavelength of 250 nm or shorter or an electron beam; and developing it with a developing solution after subjecting it to a heat treatment, if necessary.

39. The method of forming a pattern according to claim 38, wherein the light used for exposure is an ArF excimer laser.

40. A resist composition, which comprises at least one polymer according to any one of claims 6 to 22 and a photoacid generator.

41. A method of forming a pattern, which comprises the steps of:

coating the resist composition according to claim 40, onto a substrate to be processed;

exposing the substrate to a light with a wavelength of 250 nm or shorter or an electron beam; and development.

42. The method of forming a pattern according to claim 41, wherein the light used for exposure is an ArF excimer laser.

43. A method of forming a pattern, which comprises the steps of:

coating the resist composition according to 40 onto a substrate to be processed;

exposing the substrate to a light with a wavelength of 250 nm or shorter or an electron beam; and developing it with a developing solution after subjecting it to a heat treatment, if necessary.

44. The method of forming a pattern according to claim 43, wherein the light used for exposure is an ArF excimer laser.

* * * * *